(12) United States Patent
Bankaitis-Davis et al.

(10) Patent No.: US 7,935,482 B2
(45) Date of Patent: May 3, 2011

(54) GENE EXPRESSION PROFILING FOR IDENTIFICATION MONITORING AND TREATMENT OF RHEUMATOID ARTHRITIS

(75) Inventors: Danute Bankaitis-Davis, Longmont, CO (US); Kathy Storm, Longmont, CO (US); Lisa Siconolfi, Westminster, CO (US); David B. Trollinger, Boulder, CO (US); Karl Wassmann, Dover, MA (US)

(73) Assignee: Source Precision Medicine, Inc., Boulder, CO (US)

( * ) Notice: Subject to any disclaimer, the term of this patent is extended or adjusted under 35 U.S.C. 154(b) by 260 days.

(21) Appl. No.: 11/529,010

(22) Filed: Sep. 27, 2006

(65) Prior Publication Data

US 2007/0196835 A1 Aug. 23, 2007

Related U.S. Application Data

(60) Provisional application No. 60/721,052, filed on Sep. 27, 2005.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS 5,744,305 A 4/1998 Fodor et al. ................... 435/6

FOREIGN PATENT DOCUMENTS

| WO | WO 98/24935 | 6/1998 |
| WO | WO 01/25473 | 4/2001 |
| WO | WO-03/060465 A2 | 7/2003 |
| WO | WO 03/072827 A1 | 9/2003 |
| WO | WO 2004/057034 A1 | 7/2004 |
| WO | WO 2004/110244 A2 | 12/2004 |

OTHER PUBLICATIONS

Lucentini et al. (The Scientist (2004) vol. 18).*
Wu et al. (BMC Genomics. Sep. 16, 2008).*
Heller et al. (Proc Natl Acad Sci U S A. Mar. 18, 1997;94(6):2150-5).*
Information Hyperlinked Over Proteins (http://www.ihop-net.org/UniPub/iHOP/gismo/90144.html?ORGANISM_ID=1; retrieved Jan. 25, 2009).*
Information Hyperlinked Over Proteins ( http://www.ihop-net.org/UniPub/iHOP/gismo/91466.html?ORGANISM_ID=1; retrieved Jan. 25, 2009).*
Seibl et al. (Am J Pathol. Apr. 2003;162(4):1221-7).*
Cha et al. (Rheumatol Int. Jul. 2004;24(4):207-11. Epub Jul. 26, 2003).*
Lucentini et al. (The Scientist (2004) vol. 18) titled his article Gene Association Studies Typically Wrong.*
Bovin et al., "Blood cell gene expression profiling in rheumatoid arthritis; Discriminative genes and effect of rheumatoid factor", *Immunol. Lett.* 93: 217-226 (2004).
International Search Report for PCT/US2006/038170, mailed May 22, 2007.
Hirayama et al., "Concentrations of thrombopoietin in bone marrow in normal subjects and in patients with idiopathic thrombocytopenic purpura, aplastic anemia, and essential thrombocythemia correlate with its mRNA expression of bone marrow stromal cells", *Blood*, 92:46-52 (1998).
Lie et al., "Advances in quantitative PCR technology: 5' nuclease assays", *Curr. Opin. Biotechnol.*, 9:43-48 (1998).
Magidson, "Maximum likelihood assessment of clinical trials based on an ordered categorical response", *Drug Information Journal*, 30(1):143-170 (1996).
Vermunt et al., "Latent Class Cluster Analysis", *Applied Latent Class Analysis*, p. 89-106 (2002).
Seibl et al., "Expression and Regulation of Toll-Like Receptor 2 in Rheumatoid Arthritis Synovium" *Am. J. Pathol.* 162(4):1221-1227 (2003).
Radstake et al., "Expression of Toll-Like Receptors 2 and 4 in Rheumatoid Synovial Tissue and Regulation by Proinflammatory Cytokines Interleukin-12 and Interleukin-18 Via Interferon-γ" *Arthritis & Rheumatism*, 50(12):3856-3865 (2004).

* cited by examiner

*Primary Examiner* — Christopher M. Babic
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

A method is provided in various embodiments for determining a profile data set for a subject with rheumatoid arthritis or inflammatory conditions related to rheumatoid arthritis based on a sample from the subject, wherein the sample provides a source of RNAs. The method includes using amplification for measuring the amount of RNA corresponding to at least 2 constituents from Tables 1-2 and Tables 4-10. The profile data set comprises the measure of each constituent, and amplification is performed under measurement conditions that are substantially repeatable.

9 Claims, 45 Drawing Sheets

| Gene or index | RA mean dCt (n=23) | Normals mean dCt (n=69) | Relative Expression (fold change from normals) | t test P value |
|---|---|---|---|---|
| MMP9 | 14.48 | 16.24 | 3.37 | <.0001 |
| HSPA1A | 13.24 | 14.60 | 2.56 | <.0001 |
| IL1RN | 14.96 | 16.30 | 2.52 | <.0001 |
| TGFB1 | 12.10 | 13.41 | 2.49 | <.0001 |
| C1QA | 20.08 | 21.29 | 2.31 | <.0001 |
| CD14 | 13.58 | 14.77 | 2.27 | <.0001 |
| VEGF | 22.15 | 22.69 | 1.45 | 0.0002 |
| TNFSF6 | 19.93 | 20.62 | 1.61 | 0.0004 |
| CD3Z | 15.02 | 15.09 | 1.05 | 0.6181 |
| IL8 | 20.72 | 20.80 | 1.05 | 0.807 |
| PLA2G7 | 19.47 | 19.63 | 1.12 | 0.4295 |
| CD19 | 19.00 | 18.50 | 0.71 | 0.0232 |

Fig. 12

Identify Molecular Markers in RA

| Gene name | Normal mean ΔCT (n=69) | Relative Expression (fold change from normals) | | | t-test p value | | |
|---|---|---|---|---|---|---|---|
| | | Unstable on DMARD (n=24) | Stable on DMARD (n=19) | Stable on TNF blockers (n=20) | Unstable on DMARD (n=24) | Stable on DMARD (n=19) | Stable on TNF blockers (n=20) |
| MMP9 | 16.44 | 3.45 | 2.75 | 1.16 | <.0001 | <.0001 | 0.4275 |
| CD14 | 14.87 | 2.25 | 1.71 | 1.11 | <.0001 | <.0001 | 0.3185 |
| TIMP1 | 15.08 | 2.02 | 1.64 | 1.07 | <.0001 | <.0001 | 0.4372 |
| HSPA1A | 14.73 | 2.62 | 2.15 | 1.14 | <.0001 | <.0001 | 0.271 |
| TGFB1 | 13.53 | 2.52 | 1.95 | 0.96 | <.0001 | <.0001 | 0.5605 |
| IL10 | 22.97 | 1.34 | 1.29 | 0.66 | 0.0206 | 0.0288 | 0.0006 |
| IL1RN | 16.5 | 2.48 | 2.14 | 0.67 | <.0001 | <.0001 | 0.0004 |
| CXCL1 | 19.86 | 1.89 | 1.78 | 0.73 | <.0001 | <.0001 | 0.0119 |
| IL1B | 16.23 | 2.24 | 2.03 | 0.92 | <.0001 | <.0001 | 0.4396 |
| PTGS2 | 17.95 | 2.23 | 1.56 | 0.77 | <.0001 | 0.0001 | 0.0091 |
| CD19 | 18.66 | 0.64 | 0.68 | 0.69 | 0.014 | 0.014 | 0.0156 |

Fig. 13

**Active RA\* Reveals Significant Over-expression of Pro-Inflammatory Genes (in SD units vs. Normal)**

| Subject | TGFB1 | TIMP1 | PTGS2 | IL1B | IL1RN | TNF | IL1A | IL6 | IR-105 |
|---|---|---|---|---|---|---|---|---|---|
| 01B | 5.67 | 3.73 | 1.85 | 3.21 | 2.89 | 2.87 | 0.33 | | 8.96 |
| 07J | 5.05 | 2.46 | 3.64 | 3.24 | 2.27 | 2.19 | | | 6.15 |
| 09J | 4.79 | 2.54 | 2.99 | 2.91 | 3.26 | 1.53 | | | 4.87 |
| 03J | 4.73 | 2.31 | 3.20 | 2.18 | 3.63 | 0.39 | 0.77 | 0.78 | 5.86 |
| 06B | 4.36 | 3.94 | 2.53 | 2.41 | 2.64 | 1.97 | 0.59 | | 6.04 |
| 14B | 4.27 | 2.03 | 2.79 | 3.23 | 3.30 | 2.93 | | | 6.02 |
| 05B | 3.80 | 0.72 | 1.77 | 2.45 | 1.51 | 1.92 | | | 2.16 |
| 06J | 3.77 | 2.62 | 1.69 | 2.70 | 4.48 | 2.20 | 0.67 | | 4.37 |
| 13J | 3.55 | 1.69 | 0.95 | 1.47 | 2.41 | 1.92 | | | 3 |
| 12J | 3.44 | 1.90 | 1.16 | 3.33 | 3.18 | 1.19 | | | 4.4 |
| 19B | 3.25 | 3.63 | 2.90 | 2.27 | 2.74 | 0.58 | | | 6.34 |
| 08B | 3.17 | 0.98 | 1.40 | 4.12 | 3.24 | -1.04 | | | 2.93 |
| 20J | 3.14 | 2.25 | 2.21 | 1.72 | 3.16 | 1.10 | | | 2.89 |
| 11B | 3.03 | 2.29 | 1.80 | 0.81 | 1.44 | 1.58 | | | 1.98 |
| 15J | 2.97 | 2.74 | 5.61 | 1.73 | 2.41 | 0.39 | 1.21 | 1.05 | 2.8 |
| 15B | 2.94 | 1.21 | 0.83 | 1.87 | 1.48 | 1.39 | | | 2.85 |
| 14J | 2.67 | 1.96 | 1.33 | 0.05 | 0.38 | 0.99 | | | 1.04 |
| 17B | 1.96 | 0.72 | 0.24 | 0.48 | 1.13 | -0.38 | | | 2.04 |

*Active RA=6 or more swollen joints, 9 or more tender joints, CRP>2 mg/dL and may require introduction of more aggressive therapy*

*Blank cells represent measurements below detection limits*

Fig. 14

Client Study of Active RA* Also Reveals Over-expression of Pro-Inflammatory Genes (in SD units vs Normal)

| Subject | TGFB1 | TIMP1 | PTGS2 | IL1B | IL1RN | TNF | IL1A | IL6 |
|---|---|---|---|---|---|---|---|---|
| 13 | 5.21 | 4.87 | 3.36 | 1.43 | 1.85 | 2.21 | | 0.30 |
| 16 | 4.61 | 4.61 | 2.69 | 2.45 | 2.37 | 1.90 | | 0.30 |
| 3 | 4.26 | 3.94 | 1.59 | 1.14 | 1.55 | -0.20 | | 0.50 |
| 15 | 4.23 | 4.74 | 3.10 | 2.00 | 2.58 | 0.80 | | |
| 14 | 4.15 | 4.79 | 1.18 | 1.79 | 1.45 | -0.79 | | |
| 21 | 3.82 | 4.19 | 3.07 | 2.31 | 2.42 | 0.05 | | |
| 17 | 3.82 | 3.97 | 3.14 | 2.58 | 2.08 | 2.47 | | |
| 22 | 3.42 | 4.06 | 1.24 | 1.04 | 1.31 | 0.65 | | |
| 8 | 3.25 | 3.30 | 1.85 | 0.85 | 2.13 | 0.74 | | |
| 18 | 3.09 | 5.11 | 2.77 | 0.48 | 1.02 | -0.11 | | |
| 6 | 2.99 | 2.65 | 1.05 | 1.97 | 2.52 | -0.41 | | |
| 20 | 2.99 | 4.09 | 2.20 | 3.25 | 1.89 | 0.25 | | |
| 5 | 2.91 | 3.04 | 0.45 | 0.89 | 1.12 | 0.56 | 0.18 | 0.10 |
| 7 | 2.86 | 2.92 | 2.06 | 1.54 | 0.83 | 1.83 | | |
| 4 | 2.51 | 0.11 | 1.16 | 0.50 | 1.07 | 1.47 | | |
| 19 | 2.43 | 2.98 | 2.34 | 2.09 | 1.05 | -0.21 | | |
| 1 | 2.17 | 1.94 | 1.40 | 0.87 | 1.81 | -1.60 | | |
| 2 | 2.09 | 2.56 | 2.08 | 1.48 | 2.19 | 1.26 | | |
| 11 | 2.03 | 3.19 | 2.24 | 1.13 | 1.45 | 0.15 | | |
| 9 | 1.96 | 1.04 | 1.41 | 1.68 | 0.54 | 0.27 | | 0.14 |
| 10 | 1.47 | 0.82 | 1.26 | 2.99 | 2.75 | 1.08 | | 0.37 |
| 12 | 1.39 | 2.73 | 1.06 | 1.74 | 0.69 | 0.53 | | 0.24 |

*Active RA=6 or more swollen joints, 9 or more tender joints, CRP>1.5 mg/dL with a 6 week DMARD washout Blank cells represent measurements below detection limits

Fig. 15

Well Controlled RA* Subjects on TNF Inhibitors
Reveal Normal Gene Expression (in SD units vs Normal)

| Subject | TGFB1 | TIMP1 | PTGS2 | IL1B | IL1RN | TNF | IL1A | IL6 | X-1-IR-105 |
|---|---|---|---|---|---|---|---|---|---|
| 01a | 3.51 | 2.26 | 1.08 | 1.13 | 2.31 | 0.61 | | | 5.44 |
| 20 | 1.29 | 0.15 | -0.02 | -0.18 | -0.98 | -0.15 | | | -0.04 |
| 8 | 0.91 | 1.46 | -0.11 | 0.71 | -0.12 | -0.57 | | | 1.48 |
| 11 | 0.90 | 0.91 | -0.86 | 0.31 | -0.96 | 0.53 | | | 0.19 |
| 9 | 0.71 | 2.67 | -0.29 | -0.50 | -0.49 | -2.18 | | | 1.17 |
| 7 | 0.69 | 1.50 | -0.72 | -0.45 | -0.87 | -0.26 | | | 0.34 |
| 16 | 0.48 | 1.30 | 0.74 | -0.47 | -1.86 | -0.79 | | | -0.05 |
| 2 | 0.32 | -0.22 | 0.26 | 0.80 | -1.38 | 1.28 | | 0.95 | 0.24 |
| 19 | -0.01 | -0.39 | -0.24 | -0.07 | -0.70 | -0.05 | | | -0.57 |
| 12a | -0.02 | 1.00 | -0.65 | -1.10 | -1.35 | -1.85 | 0.54 | 0.17 | -0.95 |
| 14 | -0.16 | -0.23 | -1.84 | 0.13 | -0.21 | 0.66 | | | -0.36 |
| 5 | -0.41 | -0.64 | -1.13 | -0.35 | -1.30 | 0.13 | | | |
| 17 | -0.48 | 0.55 | -1.15 | -0.53 | -0.49 | -0.21 | | | -0.4 |
| 15 | -0.55 | -0.38 | -0.44 | 0.68 | -0.99 | -1.46 | | | -0.87 |
| 10 | -1.31 | -0.17 | -1.52 | -0.77 | -1.67 | -0.02 | | 1.28 | -1.56 |
| 6 | -1.39 | -0.14 | -0.44 | 1.12 | -0.41 | -0.89 | | | -0.39 |
| 18 | -1.47 | -0.97 | -1.01 | -2.39 | -2.64 | -1.49 | | | -2.69 |
| 13 | -1.77 | -1.94 | -2.72 | -2.90 | -3.41 | -1.49 | | | -3.32 |
| 4 | -1.90 | -1.62 | -1.37 | 0.37 | -0.82 | -0.05 | | 0.33 | |

*Well-controlled RA=stable therapeutic regimen including TNF inhibitors for at least 3 months; Subject 01a flared within a week of sample collection
Blank cells represent measurements below detection limits

Fig. 16

Source RA Biomarkers Track Effective Therapy

| Gene | Baseline | | Week 4 | | Terminal | |
|---|---|---|---|---|---|---|
| | Relative Expression | t test P value | Relative Expression | t test P value | Relative Expression | t test P value |
| MMP9 | 5.2 | <.0001 | 3.2 | <.0001 | 1.7 | 0.0038 |
| IL1R1 | 3.0 | <.0001 | 1.6 | 0.0011 | 1.4 | 0.0408 |
| CD14 | 1.9 | <.0001 | 1.7 | <.0001 | 1.4 | 0.0085 |
| TIMP1 | 1.9 | <.0001 | 1.5 | <.0001 | 1.3 | 0.0193 |
| HSPA1A | 1.7 | <.0001 | 1.3 | 0.0292 | 1.1 | 0.6009 |
| TGFB1 | 1.7 | <.0001 | 1.5 | <.0001 | 1.2 | 0.009 |
| IL10 | 1.7 | <.0001 | 1.3 | 0.006 | 1.4 | 0.0014 |
| IL1RN | 1.6 | <.0001 | 1.1 | 0.1636 | 1.0 | 0.7194 |
| CXCL1 | 1.5 | 0.0001 | 1.0 | 0.6622 | 0.8 | 0.0273 |
| IL1B | 1.5 | 0.0003 | 1.1 | 0.2935 | 0.9 | 0.329 |
| PTGS2 | 1.4 | 0.0042 | 1.3 | 0.0473 | 0.9 | 0.6604 |
| CD19 | 0.5 | <.0001 | 0.6 | <.0001 | 0.6 | 0.0002 |

N=22 on Kineret or Kineret + sTNF-R1

Fig. 17

Determine Associations with Clinical Endpoints -- Running Clear Clinical Trials

- SPECTRA Longitudinal Study
- AMGEN - B. Bresnihan, Dublin, IE
- Kineret or sTNF-R1 + Kineret
- 22 RA Subjects; 3 Time-points
- Clear Clinical Response

|      | Baseline | 4 Weeks | Terminal |
|------|----------|---------|----------|
| DAS  | 6.51     | 5.35    | 4.88     |
| SJC  | 21       | 12      | 11       |
| TJC  | 24       | 14      | 12       |
| MDAD | 66       | 42      | 34       |
| HAQ  | 1.68     | 1.22    | 1.07     |

Fig. 23

Determine Associations with Clinical Endpoints -- Simple Correlations

Table 3. Pearson Correlation Coefficients
Prob > [r] under H0: Rho=0
Number of Observations

|  | DAS | Swollen Joints | Tender Joints | HAQ | Physicians Assess Disease | Subject Assess Disease | Subject Assess Pain | ESR | CRP |
|---|---|---|---|---|---|---|---|---|---|
| CD14 | -0.335 / 0.0101 / 58 | -0.1502 / 0.2604 / 58 | -0.1916 / 0.1497 / 58 | -0.1296 / 0.3366 / 57 | -0.2751 / 0.0366 / 58 | -0.1359 / 0.3134 / 57 | -0.1996 / 0.1366 / 57 | -0.3629 / 0.0051 / 58 | -0.3891 / 0.0028 / 57 |
| CD19 | 0.19144 / 0.1394 / 61 | -0.0079 / 0.9521 / 61 | -0.0857 / 0.5115 / 61 | 0.1211 / 0.3567 / 59 | 0.04963 / 0.7041 / 60 | 0.27331 / 0.0346 / 60 | 0.22693 / 0.0812 / 60 | 0.43543 / 0.0005 / 61 | 0.23859 / 0.0664 / 60 |
| CXCL1 | -0.329 / 0.0103 / 60 | -0.1302 / 0.3214 / 60 | -0.1309 / 0.3188 / 60 | -0.0926 / 0.4854 / 59 | -0.287 / 0.0262 / 60 | -0.1519 / 0.2509 / 59 | -0.0822 / 0.5361 / 59 | -0.3017 / 0.0191 / 60 | -0.4224 / 0.0009 / 59 |
| HSPA1A | -0.3358 / 0.0087 / 60 | -0.2488 / 0.0553 / 60 | -0.2972 / 0.0211 / 60 | -0.2571 / 0.0493 / 59 | -0.3299 / 0.01 / 60 | -0.2675 / 0.0406 / 59 | -0.2654 / 0.0422 / 59 | -0.2765 / 0.0325 / 60 | -0.4309 / 0.0007 / 59 |
| IL10 | -0.3044 / 0.0171 / 61 | -0.0643 / 0.6225 / 61 | -0.1964 / 0.1293 / 61 | -0.1793 / 0.1705 / 60 | -0.2759 / 0.0314 / 61 | -0.19 / 0.1458 / 60 | -0.2214 / 0.0891 / 60 | -0.4316 / 0.0005 / 61 | -0.383 / 0.0025 / 60 |
| IL1B | 0.00075 / 0.9954 / 61 | 0.13837 / 0.2876 / 61 | -0.0058 / 0.9645 / 61 | -0.0102 / 0.9387 / 60 | 0.01098 / 0.9331 / 61 | -0.0736 / 0.5764 / 60 | -0.1182 / 0.3685 / 60 | -0.0114 / 0.9307 / 61 | -0.1063 / 0.4188 / 60 |
| IL1R1 | -0.3597 / 0.0044 / 61 | -0.2859 / 0.0255 / 61 | -0.3451 / 0.0065 / 61 | -0.2826 / 0.0287 / 60 | -0.3228 / 0.0112 / 61 | -0.3092 / 0.0162 / 60 | -0.329 / 0.0103 / 60 | -0.2544 / 0.0479 / 61 | -0.3884 / 0.0022 / 60 |
| IL1RN | -0.2328 / 0.071 / 61 | -0.1358 / 0.2969 / 61 | -0.2536 / 0.0486 / 61 | -0.0245 / 0.8523 / 60 | -0.2664 / 0.0379 / 61 | -0.1691 / 0.1964 / 60 | -0.1964 / 0.1326 / 60 | -0.1986 / 0.1249 / 61 | -0.2165 / 0.0967 / 60 |
| MMP9 | -0.5504 / <.0001 / 61 | -0.426 / 0.0006 / 61 | -0.3798 / 0.0025 / 61 | -0.3157 / 0.014 / 60 | -0.543 / <.0001 / 61 | -0.3387 / 0.0081 / 60 | -0.2402 / 0.0645 / 60 | -0.4828 / <.0001 / 61 | -0.601 / <.0001 / 60 |
| PTGS2 | -0.1113 / 0.3972 / 60 | -0.0036 / 0.9783 / 60 | -0.0482 / 0.7147 / 60 | 0.03264 / 0.8061 / 59 | -0.0587 / 0.6558 / 60 | 0.04282 / 0.7474 / 59 | 0.03393 / 0.7986 / 59 | -0.1242 / 0.3443 / 60 | -0.2728 / 0.0366 / 59 |
| TGFB1 | -0.2823 / 0.0275 / 61 | -0.2609 / 0.0423 / 61 | -0.1868 / 0.1494 / 61 | -0.0615 / 0.6409 / 60 | -0.2834 / 0.0269 / 61 | -0.1012 / 0.4415 / 60 | -0.1064 / 0.4183 / 60 | -0.2138 / 0.098 / 61 | -0.3841 / 0.0024 / 60 |
| TIMP1 | -0.396 / 0.0016 / 61 | -0.2744 / 0.0324 / 61 | -0.2818 / 0.0278 / 61 | -0.1066 / 0.4174 / 60 | -0.3031 / 0.0176 / 61 | -0.1405 / 0.2844 / 60 | -0.1524 / 0.2452 / 60 | -0.3295 / 0.0095 / 61 | -0.4551 / 0.0003 / 60 |

Fig. 24

Individual Biomarkers Are Associated with DAS -- Mixed Model Analysis

| Gene | Mixed Model | |
|---|---|---|
| | Slope | p-value |
| MMP9 | -0.4750 | 0.0005 |
| IL1R1 | -0.6058 | 0.0002 |
| CD14 | -0.6064 | 0.0322 |
| TIMP1 | -0.7679 | 0.0050 |
| HSPA1A | -0.7506 | 0.0110 |
| TGFB1 | -0.5236 | 0.1035 |
| IL10 | -0.3780 | 0.0270 |
| IL1RN | -0.4563 | 0.0464 |
| CXCL1 | -0.6578 | 0.0132 |
| IL1B | -0.3397 | 0.1416 |
| PTGS2 | -0.5314 | 0.0393 |
| CD19 | 0.1624 | 0.3041 |

Fig. 25

Unstable on Methotrexate - Relationship of Gene Expression (dCt) to
Physicians Assessment of Disease (Correlation and Mixed Model)

|  | Correlation Method | | Mixed Model | |
|---|---|---|---|---|
|  | Correlation Method | | Mixed Model | |
| Gene | Correlation (r) | p-value | slope | p-value |
| ADAM17 | -0.35015 | 0.093467 | -19.5959 | 0.060036 |
| B7 | 0.053122 | 0.761833 | 1.913337 | 0.795449 |
| C1QA | -0.19666 | 0.257496 | -3.68344 | 0.262627 |
| CCL2 | -0.24215 | 0.254282 | -5.54224 | 0.264592 |
| CD14 | -0.18539 | 0.286309 | -9.4166 | 0.293239 |
| CD19 | 0.149429 | 0.39158 | 3.884658 | 0.292855 |
| CD3Z | 0.244166 | 0.157496 | 9.344345 | 0.164282 |
| CD4 | 0.233964 | 0.176138 | 11.31798 | 0.158185 |
| CD8A | -0.07848 | 0.654069 | -1.21027 | 0.711584 |
| CRP | 0.270776 | 0.200622 | 10.2905 | 0.002288 |
| CSF2 | 0.560404 | 0.000463 | 36.67816 | 0.000338 |
| CSF3 | 0.032774 | 0.851736 | 0.561504 | 0.898613 |
| CTLA4 | -0.18741 | 0.380528 | -4.80123 | 0.389239 |
| CXCL1 | -0.47077 | 0.004315 | -21.5215 | 0.005177 |
| CXCL2 | -0.07251 | 0.678907 | -11.1295 | 0.390473 |
| CYBB | -0.25026 | 0.238227 | -10.4597 | 0.249184 |
| DPP4 | -0.21514 | 0.312695 | -5.71648 | 0.323808 |
| EGR1 | 0.045667 | 0.832193 | 1.525175 | 0.853063 |
| ELA2 | 0.305192 | 0.147009 | 6.597999 | 0.076783 |
| F3 | 0.537135 | 0.000878 | 42.31838 | 0.000904 |
| GCLC | 0.061057 | 0.776861 | 2.331595 | 0.803605 |
| HLA-DRB1 | 0.067809 | 0.698728 | 0.549957 | 0.657853 |
| HMGB1 | -0.39847 | 0.053776 | -18.1717 | 0.047339 |
| HMOX1 | 0.135643 | 0.437197 | 5.871976 | 0.436379 |
| HSPA1A | -0.11322 | 0.517273 | -6.81662 | 0.497903 |
| ICAM1 | -0.07731 | 0.658895 | -4.04804 | 0.672131 |
| ICOS | -0.21551 | 0.311847 | -5.49586 | 0.316737 |
| IFI16 | -0.35123 | 0.092386 | -14.4526 | 0.065852 |
| IFNA2 | 0.026501 | 0.879884 | 0.31491 | 0.92991 |
| IFNG | -0.2123 | 0.220811 | -10.8002 | 0.219335 |
| IL10 | -0.32905 | 0.053594 | -11.2548 | 0.021898 |
| IL12B | 0.270723 | 0.115722 | 22.1184 | 0.062449 |
| IL13 | 0.163122 | 0.349127 | 14.11438 | 0.256338 |
| IL15 | -0.02854 | 0.870728 | -1.30439 | 0.800278 |
| IL18 | -0.28444 | 0.097703 | -17.1458 | 0.057217 |
| IL18BP | 0.049762 | 0.776501 | 2.019016 | 0.808564 |
| IL1A | 0.21087 | 0.224005 | 16.07607 | 0.117035 |

Fig. 26

|  | Correlation Method | | Mixed Model | |
| --- | --- | --- | --- | --- |
| Gene | Correlation (r) | p-value | slope | p-value |
| IL1B | -0.43266 | 0.009435 | -15.9726 | 0.009357 |
| IL1R1 | -0.16915 | 0.429437 | -5.78732 | 0.350865 |
| IL1RN | -0.58206 | 0.000245 | -23.734 | 0.000113 |
| IL2 | 0.215282 | 0.214239 | 16.15896 | 0.102055 |
| IL4 | 0.235218 | 0.219337 | 19.82502 | 0.175906 |
| IL5 | 0.120975 | 0.488778 | 2.764972 | 0.491848 |
| IL6 | 0.162457 | 0.351121 | 13.61714 | 0.297423 |
| IL8 | 0.123571 | 0.479427 | 3.709097 | 0.473342 |
| LTA | -0.01299 | 0.951974 | -0.68408 | 0.914573 |
| MMP3 | 0.492916 | 0.002626 | 39.74483 | 0.001535 |
| MMP9 | -0.29631 | 0.083917 | -9.92486 | 0.024693 |
| MNDA | -0.44925 | 0.027646 | -19.1921 | 0.033147 |
| MPO | 0.318034 | 0.129898 | 8.758466 | 0.038587 |
| NOS2A | 0.565676 | 0.000398 | 43.28037 | 0.000155 |
| PLA2G7 | -0.00931 | 0.957681 | -0.50599 | 0.925743 |
| PLAU | -0.24284 | 0.159838 | -8.98256 | 0.16201 |
| PLAUR | -0.28809 | 0.172212 | -15.7662 | 0.163202 |
| PTGS2 | -0.45686 | 0.0058 | -20.1136 | 0.003664 |
| PTPRC | -0.34164 | 0.044574 | -15.1071 | 0.030615 |
| PTX3 | 0.04569 | 0.832112 | 1.549394 | 0.86852 |
| SERPINA1 | -0.45741 | 0.024619 | -21.8551 | 0.031422 |
| SERPINE1 | 0.009822 | 0.955345 | 0.588136 | 0.918111 |
| SERPING1 | -0.19948 | 0.350029 | -3.62416 | 0.259918 |
| TGFB1 | -0.21205 | 0.221362 | -13.6323 | 0.21299 |
| TIMP1 | -0.27521 | 0.109576 | -14.0638 | 0.105624 |
| TLR2 | -0.27661 | 0.19071 | -11.3528 | 0.202585 |
| TLR4 | -0.23789 | 0.262976 | -13.6789 | 0.221161 |
| TNF | -0.22721 | 0.189311 | -8.12763 | 0.192965 |
| TNFRSF13B | 0.239423 | 0.165977 | 7.702743 | 0.113009 |
| TNFSF13B | -0.52094 | 0.001334 | -26.3538 | 0.000173 |
| TNFSF5 | -0.0659 | 0.706811 | -2.41486 | 0.665397 |
| TNFSF6 | 0.154637 | 0.375093 | 4.915237 | 0.384256 |
| TOSO | -0.06905 | 0.748528 | -1.86273 | 0.763799 |
| TXNRD1 | -0.4684 | 0.02097 | -24.7582 | 0.027172 |
| VEGF | -0.22469 | 0.194401 | -10.1794 | 0.194434 |

GENE EXPRESSION PROFILING FOR IDENTIFICATION MONITORING AND TREATMENT OF RHEUMATOID ARTHRITIS

REFERENCE TO RELATED APPLICATIONS

This application claims the benefit of U.S. Ser. No. 60/721,052, filed Sep. 27, 2005, which is incorporated herein by reference in its entirety.

FIELD OF THE INVENTION

The present invention relates generally to the identification of biological markers associated with the identification of rheumatoid arthritis (RA). More specifically, the present invention relates to the use of gene expression data in the identification, monitoring and treatment of rheumatoid arthritis and in characterization and evaluation of inflammatory conditions induced or related to rheumatoid arthritis.

BACKGROUND OF THE INVENTION

Rheumatoid arthritis (RA) is an autoimmune disease which causes chronic inflammation of the joints, the tissue around the joints, as well as other organs in the body. Because it can affect multiple other organs of the body, rheumatoid arthritis is a systemic illness and is sometimes called rheumatoid disease. Rheumatoid arthritis is a chronic disease, mainly characterized by inflammation of the lining, or synovium, of the joints. It can lead to long-term joint damage, resulting in chronic pain, loss of function and disability.

RA can start in any joint, but it most commonly begins in the smaller joints of the fingers, hands and wrists. In general, more joint erosion indicates more severe disease activity. RA progresses in three stages. The first stage is the swelling of the synovial lining, causing pain, warmth, stiffness, redness and swelling around the joint. Other common physical symptoms include fatigue, weakness, pain associated with prolonged sitting, occurrence of flares of disease activity followed by remission, rheumatoid nodules (lumps of tissue under the skin, typically found on the elbows), and muscle pain. Second is the rapid division and growth of cells, or pannus, which causes the synovium to thicken. In the third stage, the inflamed cells release enzymes that may digest bone and cartilage, often causing the involved joint to lose its shape and alignment, more pain, and loss of movement.

Because it is a chronic disease, RA continues indefinitely and may not go away. Frequent flares in disease activity can occur. Early diagnosis and treatment of RA is critical to living a productive lifestyle. Studies have shown that early aggressive treatment of RA can limit joint damage, which in turn limits loss of movement, decreased ability to work, higher medical costs and potential surgery. Currently, the characterization of a disease condition related to RA (including diagnosis, staging, monitoring disease progression, monitoring treatment effects on disease activity) is imprecise. There is no one test which positively indicates a subject has RA. A diagnosis typically is made from a combination of the following procedures and tests: a medical history; a physical exam looking for common features reported in RA including but not limited to joint swelling, joint tenderness, loss of motion in the joints, and joint malalignment; signs of RA in other organs including but not limited to skin, lungs and eyes; lab tests, including but not limited to measuring blood cell count, erythrocyte sedimentation rate (ESR), C-Reactive Protein levels, Rheumatoid Factor, and Antinuclear Antibodies; and imaging studies, including but not limited to X-rays, magnetic resonance imaging (MRI), joint ultrasound, and bone densitometry (DEXA). Thus a need exists for better ways to diagnose and monitor the progression and treatment of rheumatoid arthritis.

Several therapeutic options exist for the treatment of RA. The major goals of therapy are to relieve pain, swelling, and fatigue, and to improve joint function, stop joint damage, and prevent disability and disease related morbidity. Treatment of the disease may involve a combination of two or more therapeutics compounds, including non-steroidal anti-inflammatory drugs, ("NSAIDs", e.g., ibuprofen), COX-2 inhibitors (e.g., celecoxib (Celebrex)), low dose corticosteroids, disease-modifying anti-rheumatic drugs ("DMARDs", e.g., methotrexate, leflunomide, gold thiomalate, aurothioglucose, or auranofin), Tumor necrosis factor ("TNF") inhibitors (e.g., etanercept (Enbrel), infliximab (Remicade), and adalimumab (Humira), interleukin-1 inhibitors (e.g., injectible anakinra (Kineret)), and other biologic response modifiers ("BRMs"). However, careful monitoring of DMARD and BRM is essential to treatment. Information on any condition of a particular patient and a patient's response to types and dosages of therapeutic or nutritional agents has become an important issue in clinical medicine today not only from the aspect of efficiency of medical practice for the health care industry but for improved outcomes and benefits for the patients. Thus, there is the need for tests which can aid in the diagnosis and monitor the progression and treatment of RA.

SUMMARY OF THE INVENTION

The invention is based in part upon the identification of gene expression profiles associated with rheumatoid arthritis (RA). Theses genes are referred to herein as RA-associated genes. More specifically, the invention is based upon the surprising discovery that detection of as few as two RA-associated genes is capable of identifying individuals with or without RA with at least 75% accuracy.

In various aspects the invention provides a method for determining a profile data set for characterizing a subject with rheumatoid arthritis or an inflammatory condition related to rheumatoid arthritis based on a sample from the subject, the sample providing a source of RNAs, by using amplification for measuring the amount of RNA in a panel of constituents including at least 2 constituents from any of Tables 1, 2, 3, 4, 5, 6, 7, 8, 9 or 10 and arriving at a measure of each constituent. The profile data set contains the measure of each constituent of the panel.

Also provided by the invention is a method of characterizing rheumatoid arthritis or inflammatory condition related to rheumatoid arthritis in a subject, based on a sample from the subject, the sample providing a source of RNAs, by assessing a profile data set of a plurality of members, each member being a quantitative measure of the amount of a distinct RNA constituent in a panel of constituents selected so that measurement of the constituents enables characterization of rheumatoid arthritis.

In yet another aspect the invention provides a method of characterizing rheumatoid arthritis or an inflammatory condition related to rheumatoid arthritis in a subject, based on a sample from the subject, the sample providing a source of RNAs, by determining a quantitative measure of the amount of at least one constituent from Table 4 and 7.

The panel of constituents are selected so as to distinguish from a normal and a RA-diagnosed subject. The RA-diagnosed subject is washed out from therapy. For example, the subject is washed out from therapy for at least 1 week, 2 weeks, 3 weeks, 1 month, two months, or up to three or more months. Alternatively, the panel of constituents is selected as to permit characterizing the severity of RA in relation to a normal subject over time so as to track movement toward normal as a result of successful therapy and away from normal in response to symptomatic flare. In other aspects of the invention, the panel of constituents are selected so as to distinguish, e.g., classify stable RA subjects from unstable RA subjects. By a stable RA subject it is meant that the subject was responsive to the therapeutic being administered. By an unstable RA subject is meant that the disease was not responding to the therapeutic being administered. Thus the methods of the invention are used to determine efficacy of treatment of a particular subject.

Preferably, the panel of constituents are selected so as to distinguish, e.g., classify between a normal and a RA-diagnosed subject or an stable and a unstable subject with at least 75%, 80%, 85%, 90%, 95%, 97%, 98%, 99% or greater accuracy. By "accuracy" is meant that the method has the ability to distinguish, e.g., classify, between subjects having rheumatoid arthritis, or an inflammatory condition associated with rheumatoid arthritis, and those that do not. When the method is used to determine whether the subject is stable or unstable, the term "accuracy" is meant that the method has the ability to distinguish, e.g., classify, between subjects that are responding to therapy and those that do not. Accuracy is determined for example by comparing the results of the Gene Expression Profiling to standard accepted clinical methods of diagnosing RA, e.g., one or more symptoms of RA such as tender and swollen joints, fatigue, pain and stiffness in the joints, inflammation, or increased serum CRP levels.

The panel contains 10, 8, 5, 4, 3 or fewer constituents. Optimally, the panel of constituents includes TLR2, MMP9, IFI16, TGFB1, NFKB1, TIMP1, ICAM1, STAT3, CSPG2 or HLADRA. The panel includes two or more constituents from Table 5. Preferably, the panel includes any 2, 3, 4, or 5 genes in the combination shown in Tables, 5, 6, 8, 9 and 10 respectively. For example the panel contains i) TLR2 and one or more or the following: CD4, PTGS2, IL18BP, HSPA1A, HMBG1, C1QA, MNDA, CD19, CD86, SERPING1, CD8A, PTPRC, MYC, NFKB1, TNFSF5, LTA, TGFB1, DPP4, EGR1, IL1R1, ICAM1, IL1RN, TIMP1, MNDA, MPO, GCLC, APAF1, MMP9, TNFSF6, PLA2G7, CYBB, CD14, SERPINE1, HLADRA, MEF2C, MMP9, CASP9 pr IL1B; ii) MMP9 and one or more of the following: SERPING1, PTGS2, IFI16, HSPA1A, CD4, C1QA, MNDA, IL18BP, IL1R1, MYC, APAF1, CD86, CD19, SERPINE1, HMGB1, MPO, NFKB1, TGFB1, EGR1, PLAUR, TNFSF5, SERPINA1, LTA, TIMP1, ICAM1, TNF, TLR2, IL1B, IL1RN, IL18, ADAM17, PTPRC, CD14, HMOX1, or CD8A.; iii) IFI16 and one or more of the following: HMGB1, SERPINE1, CD19, IL1R, NFKB1, MPO, MYC, TIMP1, IL18BP, SERPINE1, CD19, ELA2, TGFB1, IL10, C1QA, PTGS2, ADAM17, IL18, CD4, HMOX1, CD86, HSPA1A, MNDA, TLR2, or MMP9; iv) TGFB1 and one or more of the following CD4, IL18BP, PTGS2, NFKB1, TLR2, IFI16, IL1R1, IL10, SERPINA1, SERPING1, MMP9, HLADRA, HSPA1A or ICAM1; v) NFKB1 and one or more of the following: CD4, IL18BP, TLR2, MMP9, IL-10, IFI16, TIMP1, CD14, IL1R1, CYBB, SERPING1, PTGS2, MYC, SERPINA1, EGR1 or TNFSF5; vi) TIMP1 and one or more of the following: CD4, MYC, SERPING1, IFI16, SERPINA1, EGR1, or TNFSF5; vii) ICAM1 and one or more of the following: HLADRA, HSPA1A, CD14, TGFBR2, MMP9, TGFB1, CSPG2, STAT3, MEF2C, IL18, CD4 and NFB1B; viii) STAT3 and one or more of the following: HLADRA, HSPA1A, CD14, TGFBR2, MMP9, TGFB1, CSPG2, ICAM1 or EGR1; ix) CSPG2 and one or more of the following: HLADRA, IL18, CD14 HSPA1A, IL1B, EGR1, TGFB1, CASP9, ITGAL, STAT3, EGR1, ICAM1, CD4, or MEF2C; vi) HLADRA and one or more of the following: CASP9, MEF2C, ITGAL, IL18, NFKB1B, CD4, NFKB1, TGFBR2, SERPINE1, CD14, HSPA1A or TLR2.

Optionally, assessing may further include comparing the profile data set to a baseline profile data set for the panel. The baseline profile data set is related to the rheumatoid arthritis or an inflammatory condition related to rheumatoid arthritis to be characterized. The baseline profile data set is derived from one or more other samples from the same subject, taken when the subject is in a biological condition different from that in which the subject was at the time the first sample was taken, with respect to at least one of age, nutritional history, medical condition, clinical indicator, medication, physical activity, body mass, and environmental exposure, and the baseline profile data set may be derived from one or more other samples from one or more different subjects. In addition, the one or more different subjects may have in common with the subject at least one of age group, gender, ethnicity, geographic location, nutritional history, medical condition, clinical indicator, medication, physical activity, body mass, and environmental exposure. A clinical indicator may be used to assess rheumatoid arthritis or an inflammatory condition related to rheumatoid arthritis of the one or more different subjects, and may also include interpreting the calibrated profile data set in the context of at least one other clinical indicator, wherein the at least one other clinical indicator includes blood chemistry, X-ray or other radiological or metabolic imaging technique, other chemical assays, and physical findings.

The baseline profile data set may be derived from one or more other samples from the same subject taken under circumstances different from those of the first sample, and the circumstances may be selected from the group consisting of (i) the time at which the first sample is taken, (ii) the site from which the first sample is taken, (iii) the biological condition of the subject when the first sample is taken.

By rheumatoid arthritis or an inflammatory condition related to rheumatoid arthritis is meant that the condition is an autoimmune condition, an environmental condition, a viral infection, a bacterial infection, a eukaryotic parasitic infection, or a fungal infection.

The sample is any sample derived from a subject which contains RNA. For example the sample is blood, a blood fraction, body fluid, and a population of cells or tissue from the subject.

Optionally one or more other samples can be taken over an interval of time that is at least one month between the first sample and the one or more other samples, or taken over an interval of time that is at least twelve months between the first sample and the one or more samples, or they may be taken pre-therapy intervention or post-therapy intervention. In such embodiments, the first sample may be derived from blood and the baseline profile data set may be derived from tissue or body fluid of the subject other than blood. Alternatively, the first sample is derived from tissue or bodily fluid of the subject and the baseline profile data set is derived from blood.

All of the forgoing embodiments are carried out wherein the measurement conditions are substantially repeatable, particularly within a degree of repeatability of better than five percent or more particularly within a degree of repeatability of better than three percent, and/or wherein efficiencies of amplification for all constituents are substantially similar, more particularly wherein the efficiency of amplification is within two percent, and still more particularly wherein the efficiency of amplification for all constituents is less than one percent.

Additionally the invention includes storing the profile data set in a digital storage medium. Optionally, storing the profile data set includes storing it as a record in a database.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 12 illustrates application of a statistical T-test to identify potential members of a signature gene expression panel that is capable of distinguishing between normal subjects and subjects suffering from unstable rheumatoid arthritis.

FIG. 13 illustrates biomarkers identified with RA that illustrate increased gene expression values relative to normal gene expression values for patients unstable on DMARD therapy or stable on DMARD therapy, compared to patients on TNF inhibitor therapy who exhibit more normal gene expression values.

FIG. 14 illustrates how patients with active RA exhibit statistically significant gene expression values relative to normal gene expression values.

FIG. 15 illustrates another study with active RA patients exhibiting statistically significant increased gene expression relative to normal gene expression values.

FIG. 16 illustrates how RA subjects stable at least 3 months on TNF inhibitors exhibit normal gene expression.

FIG. 17 illustrates how biomarkers are effective at tracking effective therapy in RA patients.

FIG. 23 illustrates a determination of associations of clinical endpoints for RA therapy.

FIG. 24 illustrates a determination of associations of RA biomarkers and clinical endpoints using simple correlation analysis.

FIG. 25 illustrates a mixed model analysis used to compare individual biomarkers for predicting RA status relative to traditional physician determined DAS values.

FIG. 26 illustrates a study of RA patients unstable Methotrexate and the relationship between gene expression (ACt) to Physician's Assessment of Disease (DAS) using simple correlation or mixed model analyses.

DETAILED DESCRIPTION OF SPECIFIC EMBODIMENTS

Definitions

Figure 1A:
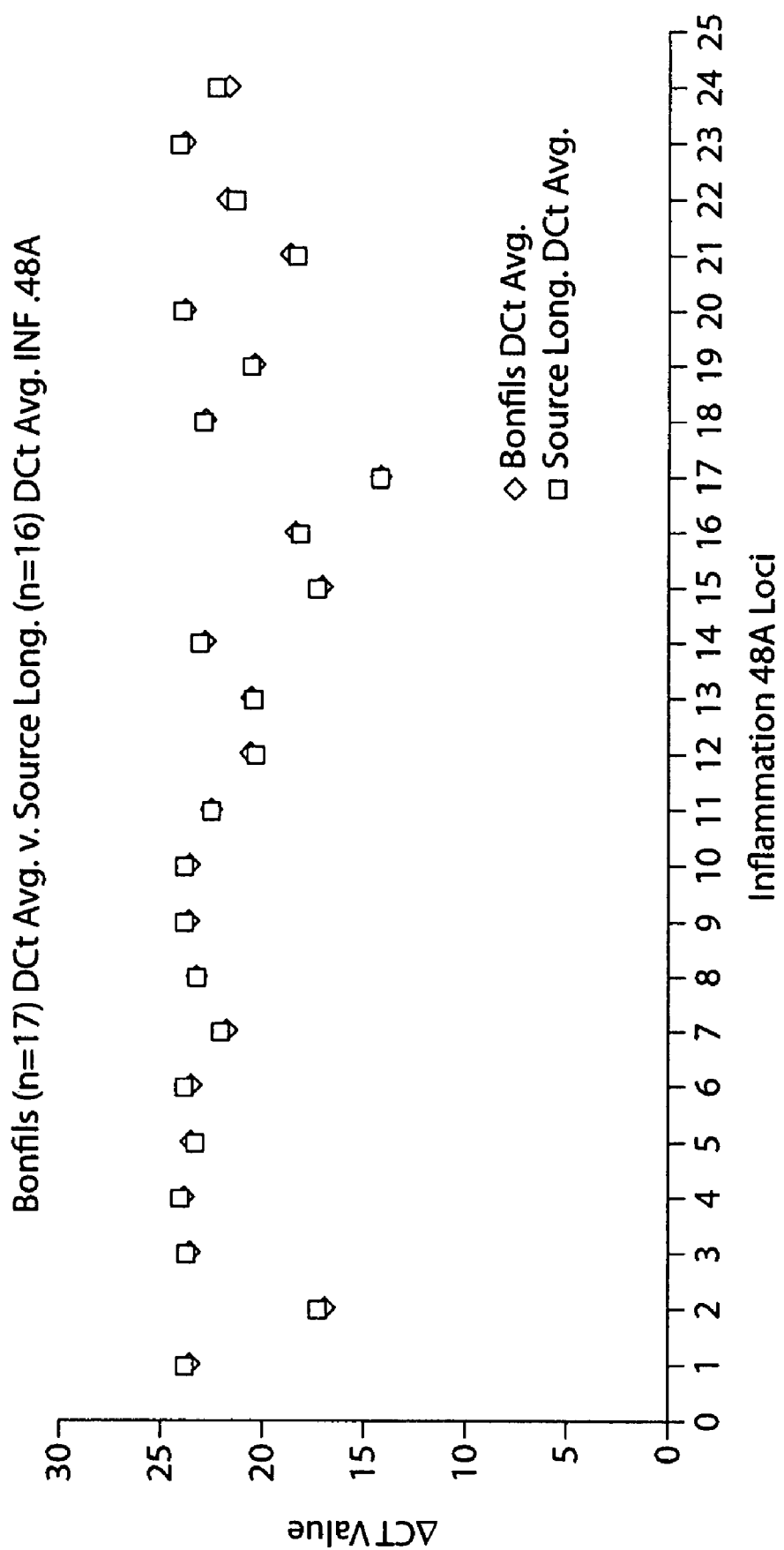
FIGS. 1A and 1B compare two different populations using Gene Expression Profiles (with respect to 48 loci of the Inflammation Gene Expression Panel included in Tables 1 and 2).

The following terms shall have the meanings indicated unless the context otherwise requires:

"Algorithm" is a set of rules for describing a biological condition. The rule set may be defined exclusively algebraically but may also include alternative or multiple decision points requiring domain-specific knowledge, expert interpretation or other clinical indicators.

An "agent" is a "composition" or a "stimulus", as those terms are defined herein, or a combination of a composition and a stimulus.

"Amplification" in the context of a quantitative RT-PCR assay is a function of the number of DNA replications that are tracked to provide a quantitative determination of its concentration. "Amplification" here refers to a degree of sensitivity and specificity of a quantitative assay technique. Accordingly, amplification provides a measurement of concentrations of constituents that is evaluated under conditions wherein the efficiency of amplification and therefore the degree of sensitivity and reproducibility for measuring all constituents is substantially similar.

A "baseline profile data set" is a set of values associated with constituents of a Gene Expression Panel resulting from evaluation of a biological sample (or population or set of samples) under a desired biological condition that is used for mathematically normative purposes. The desired biological condition may be, for example, the condition of a subject (or population or set of subjects) before exposure to an agent or in the presence of an untreated disease or in the absence of a disease. Alternatively, or in addition, the desired biological condition may be health of a subject or a population or set of subjects. Alternatively, or in addition, the desired biological condition may be that associated with a population or set of subjects selected on the basis of at least one of age group, gender, ethnicity, geographic location, nutritional history, medical condition, clinical indicator, medication, physical activity, body mass, and environmental exposure.

A "set" or "population" of samples or subjects refers to a defined or selected group of samples or subjects wherein there is an underlying commonality or relationship between the members included in the set or population of samples or subjects.

A "population of cells" refers to any group of cells wherein there is an underlying commonality or relationship between the members in the population of cells, including a group of cells taken from an organism or from a culture of cells or from a biopsy, for example, A "biological condition" of a subject is the condition of the subject in a pertinent realm that is under observation, and such realm may include any aspect of the subject capable of being monitored for change in condition, such as health; disease including cancer; trauma; aging; infection; tissue degeneration; developmental steps; physical fitness; obesity, and mood. As can be seen, a condition in this context may be chronic or acute or simply transient. Moreover, a targeted biological condition may be manifest throughout the organism or population of cells or may be restricted to a specific organ (such as skin, heart, eye or blood), but in either case, the condition may be monitored directly by a sample of the affected population of cells or indirectly by a sample derived elsewhere from the subject. The term "biological condition" includes a "physiological condition".

"Body fluid" of a subject includes blood, urine, spinal fluid, lymph, mucosal secretions, prostatic fluid, semen, haemolymph or any other body fluid known in the art for a subject.

"Calibrated profile data set" is a function of a member of a first profile data set and a corresponding member of a baseline profile data set for a given constituent in a panel.

A "clinical indicator" is any physiological datum used alone or in conjunction with other data in evaluating the physiological condition of a collection of cells or of an organism. This term includes pre-clinical indicators.

A "composition" includes a chemical compound, a nutriceutical, a pharmaceutical, a homeopathic formulation, an allopathic formulation, a naturopathic formulation, a combination of compounds, a toxin, a food, a food supplement, a mineral, and a complex mixture of substances, in any physical state or in a combination of physical states.

To "derive" a profile data set from a sample includes determining a set of values associated with constituents of a Gene Expression Panel either (i) by direct measurement of such constituents in a biological sample or (ii) by measurement of such constituents in a second biological sample that has been exposed to the original sample or to matter derived from the original sample.

"Distinct RNA or protein constituent" in a panel of constituents is a distinct expressed product of a gene, whether RNA or protein. An "expression" product of a gene includes the gene product whether RNA or protein resulting from translation of the messenger RNA.

A "Gene Expression Panel" is an experimentally verified set of constituents, each constituent being a distinct expressed product of a gene, whether RNA or protein, wherein constituents of the set are selected so that their measurement provides a measurement of a targeted biological condition.

A "Gene Expression Profile" is a set of values associated with constituents of a Gene Expression Panel resulting from evaluation of a biological sample (or population or set of samples).

A "Gene Expression Profile Inflammatory Index" is the value of an index function that provides a mapping from an instance of a Gene Expression Profile into a single-valued measure of inflammatory condition.

The "health" of a subject includes mental, emotional, physical, spiritual, allopathic, naturopathic and homeopathic condition of the subject.

"Index" is an arithmetically or mathematically derived numerical characteristic developed for aid in simplifying or disclosing or informing the analysis of more complex quantitative information. A disease or population index may be determined by the application of a specific algorithm to a plurality of subjects or samples with a common biological condition.

"Inflammation" is used herein in the general medical sense of the word and may be an acute or chronic; simple or suppurative; localized or disseminated; cellular and tissue response initiated or sustained by any number of chemical, physical or biological agents or combination of agents.

"Inflammatory state" is used to indicate the relative biological condition of a subject resulting from inflammation, or characterizing the degree of inflammation.

A "large number" of data sets based on a common panel of genes is a number of data sets sufficiently large to permit a statistically significant conclusion to be drawn with respect to an instance of a data set based on the same panel.

"Multiple sclerosis" (MS) is a debilitating wasting disease. The disease is associated with degeneration of the myelin sheaths surrounding nerve cells which leads to a loss of motor and sensory function.

A "normative" condition of a subject to whom a composition is to be administered means the condition of a subject before administration, even if the subject happens to be suffering from a disease.

A "panel" of genes is a set of genes including at least two constituents.

"Rheumatoid Arthritis" (RA) is a chronic (long-term) autoimmune disease that causes inflammation of the joints and surrounding tissues, causing joint damage and deformity. It can also affect other organs.

A "sample" from a subject may include a single cell or multiple cells or fragments of cells or an aliquot of body fluid, taken from the subject, by means including venipuncture, excretion, ejaculation, massage, biopsy, needle aspirate, lavage sample, scraping, surgical incision or intervention or other means known in the art.

A "Signature Profile" is an experimentally verified subset of a Gene Expression Profile selected to discriminate a biological condition, agent or physiological mechanism of action.

A "Signature Panel" is a subset of a Gene Expression Panel, the constituents of which are selected to permit discrimination of a biological condition, agent or physiological mechanism of action.

A "subject" is a cell, tissue, or organism, human or non-human, whether in vivo, ex vivo or in vitro, under observation. As used herein, reference to evaluating the biological condition of a subject based on a sample from the subject, includes using blood or other tissue sample from a human subject to evaluate the human subject's condition; it also includes, for example, using a blood sample itself as the subject to evaluate, for example, the effect of therapy or an agent upon the sample.

A "stimulus" includes (i) a monitored physical interaction with a subject, for example ultraviolet A or B, or light therapy for seasonal affective disorder, or treatment of psoriasis with psoralen or treatment of melanoma with embedded radioactive seeds, other radiation exposure, and (ii) any monitored physical, mental, emotional, or spiritual activity or inactivity of a subject.

"Therapy" includes all interventions whether biological, chemical, physical, metaphysical, or combination of the foregoing, intended to sustain or alter the monitored biological condition of a subject.

"Washed-out RA" is a subject diagnosed with RA and having undergone one or more forms of therapeutic treatment, whereby the therapeutic is discontinued for a specified period of time based upon the pharmacokinetic properties of the therapeutic treatment administered, and whereby the specified period of time comprises 1 week, 2 weeks, 3 weeks, 1 month, 2 months, or up to 3 or more months.

The PCT patent application publication number WO 01/25473, published Apr. 12, 2001, entitled "Systems and Methods for Characterizing a Biological Condition or Agent Using Calibrated Gene Expression Profiles," filed for an invention by inventors herein, and which is herein incorporated by reference, discloses the use of Gene Expression Panels for the evaluation of (i) biological condition (including with respect to health and disease) and (ii) the effect of one or more agents on biological condition (including with respect to health, toxicity, therapeutic treatment and drug interaction).

In particular, Gene Expression Panels may be used for measurement of therapeutic efficacy of natural or synthetic compositions or stimuli that may be formulated individually or in combinations or mixtures for a range of targeted biological conditions; prediction of toxicological effects and dose effectiveness of a composition or mixture of compositions for an individual or for a population or set of individuals or for a population of cells; determination of how two or more different agents administered in a single treatment might interact so as to detect any of synergistic, additive, negative, neutral or toxic activity; performing pre-clinical and clinical trials by providing new criteria for pre-selecting subjects according to informative profile data sets for revealing disease status; and conducting preliminary dosage studies for these patients prior to conducting phase 1 or 2 trials. These Gene Expression Panels may be employed with respect to samples derived from subjects in order to evaluate their biological condition.

The present invention provides Gene Expression Panels for the evaluation or characterization of rheumatoid arthritis and inflammatory condition related to rheumatoid arthritis in a subject. In addition, the Gene Expression Profiles described herein also provided the evaluation of the effect of one or more agents for the treatment of rheumatoid arthritis and inflammatory condition related to rheumatoid arthritis.

This Gene expression panel is referred to herein as "RA Expression Panel". A RA Expression panel includes one or more genes, e.g., constituent, listed in Tables 1-2, and Tables 4-10. Each gene of the RA Expression panel is referred to herein as an RA associated gene or an RA associated constituent.

By evaluating or characterizing rheumatoid arthritis is meant diagnosing rheumatoid arthritis, assessing the risk of developing rheumatoid arthritis or assessing the prognosis of a subject with rheumatoid arthritis. Similarly, by evaluating or characterizing an agent for treatment of rheumatoid arthritis is meant identifying agents suitable for the treatment of rheumatoid arthritis. The agents can be compounds known to treat RA or compounds that have not been shown to treat RA.

Rheumatoid arthritis and inflammatory condition related to rheumatoid arthritis is evaluated by determining the level of expression (e.g., a quantitative measure) of one or more RA genes. The level of expression is determined by any means known in the art, such as for example quantitative PCR. The measurement is obtained under conditions that are substantially repeatable. Optionally, the qualitative measure of the constituent is compared to a baseline level (e.g. baseline profile set). A baseline level is a level expression of the constituent in one or more subjects known not to be suffering from rheumatoid arthritis (e.g., a healthy individual). Alternatively, the baseline level is derived from one or more subjects known to be suffering from rheumatoid arthritis. Optionally, the baseline level is derived from the same subject from which the first measure is derived. For example, the baseline is taken from a subject prior to receiving treatment for RA, or at different time periods during a course of treatment. Such methods allow for the evaluation of a particular treatment for a selected individual. Comparison can be performed on test (e.g., patient) and reference samples (e.g., baseline) measured concurrently or at temporally distinct times. An example of the latter is the use of compiled expression information, e.g., a sequence database, which assembles information about expression levels RA genes.

A change in the expression pattern in the patient-derived sample of a RA gene compared to the normal baseline level indicates that the subject is suffering from or is at risk of developing rheumatoid arthritis. In contrast, when the methods are applied prophylacticly, a similar level compared to the normal control level in the patient-derived sample of a RA gene indicates that the subject is not suffering from or is at risk of developing rheumatoid arthritis. Whereas, a similarity in the expression pattern in the patient-derived sample of a RA gene compared to the RA baseline level indicates that the subject is suffering from or is at risk of developing rheumatoid arthritis.

Expression of an effective amount of an RA gene also allows for the course of treatment of rheumatoid arthritis to be monitored. In this method, a biological sample is provided from a subject undergoing treatment, e.g., if desired, biological samples are obtained from the subject at various time points before, during, or after treatment. Expression of an effective amount of RA gene is then determined and compared to baseline profile. The baseline profile may be taken or derived from one or more individuals who have been exposed to the treatment. Alternatively, the baseline level may be taken or derived from one or more individuals who have not been exposed to the treatment. For example, samples may be collected from subjects who have received initial treatment for rheumatoid arthritis and subsequent treatment for rheumatoid arthritis to monitor the progress of the treatment.

Differences in the genetic makeup of individuals can result in differences in their relative abilities to metabolize various drugs. Accordingly, the RA Geen expression panels disclosed herein allow for a putative therapeutic or prophylactic to be tested from a selected subject in order to determine if the agent is a suitable for treating or preventing rheumatoid arthritis in the subject.

To identify a therapeutic that is appropriate for a specific subject, a test sample from the subject is exposed to a candidate therapeutic agent, and the expression of one or more of RA genes is determined. A subject sample is incubated in the presence of a candidate agent and the pattern of RA gene expression in the test sample is measured and compared to a baseline profile, e.g., a rheumatoid arthritis baseline profile or an non-rheumatoid arthritis baseline profile or an index value. The test agent can be any compound or composition.

If the reference sample, e.g., baseline is from a subject that does not have rheumatoid arthritis a similarity in the pattern of RA genes in the test sample and the reference sample indicates that the treatment is efficacious. However, a change in the pattern of RA genes in the test sample and the reference sample indicates a less favorable clinical outcome or prognosis.

By "efficacious" is meant that the treatment leads to a decrease of a sign or symptom of rheumatoid arthritis in the subject. Assessment rheumatoid arthritis is made using standard clinical protocols. Efficacy is determined in association with any known method for diagnosing or treating rheumatoid arthritis.

A Gene Expression Panel is selected in a manner so that quantitative measurement of RNA or protein constituents in the Panel constitutes a measurement of a biological condition of a subject. In one kind of arrangement, a calibrated profile data set is employed. Each member of the calibrated profile data set is a function of (i) a measure of a distinct constituent of a Gene Expression Panel and (ii) a baseline quantity.

It has been discovered that valuable and unexpected results may be achieved when the quantitative measurement of constituents is performed under repeatable conditions (within a degree of repeatability of measurement of better than twenty percent, and preferably ten percent or better, more preferably five percent or better, and more preferably three percent or better). For the purposes of this description and the following claims, a degree of repeatability of measurement of better than twenty percent as providing measurement conditions that are "substantially repeatable". In particular, it is desirable that, each time a measurement is obtained corresponding to the level of expression of a constituent in a particular sample, substantially the same measurement should result for substantially the same level of expression. In this manner, expression levels for a constituent in a Gene Expression Panel may be meaningfully compared from sample to sample. Even if the expression level measurements for a particular constituent are inaccurate (for example, say, 30% too low), the criterion of repeatability means that all measurements for this constituent, if skewed, will nevertheless be skewed systematically, and therefore measurements of expression level of the constituent may be compared meaningfully. In this fashion valuable information may be obtained and compared concerning expression of the constituent under varied circumstances.

In addition to the criterion of repeatability, it is desirable that a second criterion also be satisfied, namely that quantitative measurement of constituents is performed under conditions wherein efficiencies of amplification for all constituents are substantially similar as defined herein. When both of these criteria are satisfied, then measurement of the expression level of one constituent may be meaningfully compared with measurement of the expression level of another constituent in a given sample and from sample to sample.

Additional embodiments relate to the use of an index or algorithm resulting from quantitative measurement of constituents, and optionally in addition, derived from either expert analysis or computational biology (a) in the analysis of complex data sets; (b) to control or normalize the influence of uninformative or otherwise minor variances in gene expression values between samples or subjects; (c) to simplify the characterization of a complex data set for comparison to other complex data sets, databases or indices or algorithms derived from complex data sets; (d) to monitor a biological condition of a subject; (e) for measurement of therapeutic efficacy of natural or synthetic compositions or stimuli that may be formulated individually or in combinations or mixtures for a range of targeted biological conditions; (f) for predictions of toxicological effects and dose effectiveness of a composition or mixture of compositions for an individual or for a population or set of individuals or for a population of cells; (g) for determination of how two or more different agents administered in a single treatment might interact so as to detect any of synergistic, additive, negative, neutral of toxic activity (h) for performing pre-clinical and clinical trials by providing new criteria for pre-selecting subjects according to informative profile data sets for revealing disease status and conducting preliminary dosage studies for these patients prior to conducting phase 1 or 2 trials.

Gene expression profiling and the use of index characterization for a particular condition or agent or both may be used to reduce the cost of phase 3 clinical trials and may be used beyond phase 3 trials; labeling for approved drugs; selection of suitable medication in a class of medications for a particular patient that is directed to their unique physiology; diagnosing or determining a prognosis of a medical condition or an infection which may precede onset of symptoms or alternatively diagnosing adverse side effects associated with administration of a therapeutic agent; managing the health care of a patient; and quality control for different batches of an agent or a mixture of agents.

The Subject

The methods disclosed here may be applied to cells of humans, mammals or other organisms without the need for undue experimentation by one of ordinary skill in the art because all cells transcribe RNA and it is known in the art how to extract RNA from all types of cells.

A subject can include those who have not been previously diagnosed as having rheumatoid arthritis or an inflammatory condition related to rheumatoid arthritis. Alternatively, a subject can also include those who have already been diagnosed as having rheumatoid arthritis or an inflammatory condition related to rheumatoid arthritis. Diagnosis of RA is made, for example, from any one or combination of the following procedures: a medical history; a physical exam looking for common features reported in RA, including but not limited to joint swelling, joint tenderness, loss of motion in the joints, and joint malalignment; signs of RA in other organs, including but not limited to skin, lungs and eyes; lab tests including but limited to measuring blood cell count, erythrocyte sedimentation rate, C-Reactive Protein levels, Rheumatoid Factor, and/or Antinuclear Antibodies; and imaging studies including but not limited to X-rays, MRI, joint ultrasound, and/or bone densitometry.

Optionally, the subject has been previously treated with therapeutic agents, or with other therapies and treatment regimens for rheumatoid arthritis or an inflammatory condition related to rheumatoid arthritis, including but not limited to any one or combination of the following therapeutics: NSAIDS, e.g., ibuprofen; COX-2 inhibitors, e.g., celecoxib (Celebrex); low dose corticosteroids; DMARDs, e.g., methotrexate, leflunomide, gold thiomalate, aurothioglucose, or auranofin; TNF inhibitors, e.g., etanercept (Enbrel), infliximab (Remicade) and adalimumab (Humira); interleukin-1 inhibitors, e.g., injectible anakinra (Kineret); and other biologic response modifiers.

A subject can also include those who are suffering from, or at risk of developing rheumatoid arthritis or an inflammatory condition related to rheumatoid arthritis, such as those who exhibit known risk factors for rheumatoid arthritis or an inflammatory condition related to rheumatoid arthritis. Known risk factors for RA include, but are not limited to blood transfusions, age (increased susceptibility between ages 25-55), gender (women are 2.5 to 3 times more likely to develop RA than men), family history of RA or other autoimmune disorders, ethnic background (increased susceptibility in Caucasians and Native Americans), and obesity. Subjects suffering from or at risk of developing RA often exhibit the gradual worsening of symptoms which include but are not limited to fatigue, morning stiffness (lasting more than one hour), diffuse muscular aches, loss of appetite, and weakness. Eventually, joint pain appears, with warmth, swelling, tenderness, and stiffness of the joint after inactivity.

Selecting Constituents of a Gene Expression Panel

The general approach to selecting constituents of a Gene Expression Panel has been described in PCT application publication number WO 01/25473, incorporated herein in its entirety. A wide range of Gene Expression Panels have been designed and experimentally verified, each panel providing a quantitative measure of biological condition that is derived from a sample of blood or other tissue. For each panel, experiments have verified that a Gene Expression Profile using the panel's constituents is informative of a biological condition. (It has also been demonstrated that in being informative of biological condition, the Gene Expression Profile is used, among other things, to measure the effectiveness of therapy, as well as to provide a target for therapeutic intervention.).

Tables 1-2 and Tables 4-10 listed below, include relevant genes which may be selected for a given Gene Expression Panel, such as the Gene Expression Panels demonstrated herein to be useful in the evaluation of rheumatoid arthritis and inflammatory condition related to rheumatoid arthritis. Table 1 is a panel of 83 genes whose expression is associated with Rheumatoid Arthritis or inflammatory conditions related to Rheumatoid Arthritis. Table 2 is a panel of 103 genes whose expression is associated with Inflammation.

Tables 4-6 were derived from a longitudinal study of RA patients after initiating Interleukin-1 receptor antagonist (IL1ra) or IL1ra plus soluble TNF-α receptor 1 (sTNFR1) therapy, described in Example 5 below. Table 4 is a panel of genes derived from latent class modeling of the subjects from this study using a 1-gene model to distinguish between subjects suffering from RA and normal subjects. Tables 5-6 are panels of gene models derived from latent class modeling of the subjects from this study using a 2-gene and 3-gene model respectively, to distinguish between subjects suffering from RA and normal subjects. Constituent models selected from Tables 5 and 6 are capable of correctly classifying RA-afflicted and/or normal subjects with at least 75% accuracy. For example, in Table 5, it can be seen that the two gene model TLR2 and CD4 correctly classifies RA-afflicted subjects with 91% accuracy, and normal subjects with 98% accuracy. The 2-gene model TLR2 and C1QA correctly classifies RA-afflicted subjects with 100% accuracy, and normal subjects with 96% accuracy. In Table 6, the 3-gene model TLR2, CD4, and NFKB1 correctly classifies both RA-afflicted subjects and normal subjects with 100% accuracy. The 3-gene model TLR2, CD4, and MYC correctly classifies RA subjects with 96% accuracy and normal subjects with 99% accuracy.

Tables 7-10 were derived from a longitudinal study of RA patients after initiating NSAID, MTX or new TNF-inhibitor therapy, described in Example 6 below. Table 7 is a panel of genes derived from latent class modeling of the subjects from this study using a 1-gene model to distinguish between subjects suffering from RA and normal subjects. Tables 8-10 are panels of gene models derived from latent class modeling of the subjects from this study using a 2-gene, 3-gene, and 4-gene model respectively, to distinguish between subjects suffering from RA and normal subjects. Constituent models selected from Tables 8-10 are capable of correctly classifying RA-afflicted and/or normal subjects with at least 75% accuracy. For example, in Table 8, the two gene model ICAM1 and HLADRA correctly classifies RA-afflicted subjects with 90% accuracy, and normal subjects with 91% accuracy. In Table 9, the 3-gene model ICAM1, HLADRA, and HSPA1A correctly classifies RA-afflicted subjects with 95% accuracy, and normal subjects with 97% accuracy. In Table 10, the 4-gene model ICAM1, HLADRA, HSPA1A, and TGFB1 correctly classifies both RA-afflicted and normal subjects with 100% accuracy.

In general, panels may be constructed and experimentally verified by one of ordinary skill in the art in accordance with the principles articulated in the present application.

Design of Assays

Typically, a sample is run through a panel in triplicate; that is, a sample is divided into aliquots and for each aliquot the concentrations of each constituent in a Gene Expression Panel is measured. From over a total of 900 constituent assays, with each assay conducted in triplicate, an average coefficient of variation was found (standard deviation/average)*100, of less than 2 percent among the normalized ΔCt measurements for each assay (where normalized quantitation of the target mRNA is determined by the difference in threshold cycles between the internal control (e.g., an endogenous marker such as 18S rRNA, or an exogenous marker) and the gene of interest. This figure is a measure called "intra-assay variability". Assays have also been conducted on different occasions using the same sample material. With 72 assays, resulting from concentration measurements of constituents in a panel of 24 members, and such concentration measurements determined on three different occasions over time, an average coefficient of variation of less than 5 percent, typically less than 2%, was found. This is a measure of "inter-assay variability". Preferably, the average coefficient of variation is less than 20%, more preferably less than 10%, more preferably less than 5%, more preferably less than 4%, more preferably less than 3%, more preferably less than 2%, and even more preferably less than 1%.

It has been determined that it is valuable to use the quadruplicate or triplicate test results to identify and eliminate data points that are statistical "outliers"; such data points are those that differ by a percentage greater, for example, than 3% of the average of all three or four values. Moreover, if more than one data point in a set of three or four is excluded by this procedure, then all data for the relevant constituent is discarded.

Measurement of Gene Expression for a Constituent in the Panel

For measuring the amount of a particular RNA in a sample, methods known to one of ordinary skill in the art were used to extract and quantify transcribed RNA from a sample with respect to a constituent of a Gene Expression Panel. (See detailed protocols below. Also see PCT application publication number WO 98/24935 herein incorporated by reference for RNA analysis protocols). Briefly, RNA is extracted from a sample such as a tissue, body fluid, or culture medium in which a population of cells of a subject might be growing. For example, cells may be lysed and RNA eluted in a suitable solution in which to conduct a DNAse reaction. First strand synthesis may be performed using a reverse transcriptase. Gene amplification, more specifically quantitative PCR assays, can then be conducted and the gene of interest calibrated against an internal marker such as 18S rRNA (Hirayama et al., Blood 92, 1998: 46-52). Any other endogenous marker can be used, such as 28S-25S rRNA and 5S rRNA. Samples are measured in multiple replicates, for example, 3 replicates. In an embodiment of the invention, quantitative PCR is performed using amplification, reporting agents and instruments such as those supplied commercially by Applied Biosystems (Foster City, Calif.). Given a defined efficiency of amplification of target transcripts, the point (e.g., cycle number) that signal from amplified target template is detectable may be directly related to the amount of specific message transcript in the measured sample. Similarly, other quantifiable signals such as fluorescence, enzyme activity, disintegrations per minute, absorbance, etc., when correlated to a known concentration of target templates (e.g., a reference standard curve) or normalized to a standard with limited variability can be used to quantify the number of target templates in an unknown sample.

Although not limited to amplification methods, quantitative gene expression techniques may utilize amplification of the target transcript. Alternatively or in combination with amplification of the target transcript, quantitation of the reporter signal for an internal marker generated by the exponential increase of amplified product may also be used. Amplification of the target template may be accomplished by isothermic gene amplification strategies, or by gene amplification by thermal cycling such as PCR.

It is desirable to obtain a definable and reproducible correlation between the amplified target or reporter signal, i.e., internal marker, and the concentration of starting templates. It has been discovered that this objective can be achieved by careful attention to, for example, consistent primer-template ratios and a strict adherence to a narrow permissible level of experimental amplification efficiencies (for example 90.0 to 100%+/−5% relative efficiency, typically 99.8 to 100% relative efficiency). For example, in determining gene expression levels with regard to a single Gene Expression Profile, it is necessary that all constituents of the panels, including endogenous controls, maintain similar amplification efficiencies, as defined herein, to permit accurate and precise relative measurements for each constituent. Amplification efficiencies are regarded as being "substantially similar", for the purposes of this description and the following claims, if they differ by no more than approximately 10%, preferably by less than approximately 5%, more preferably by less than approximately 3%, and more preferably by less than approximately 1%. Measurement conditions are regarded as being "substantially repeatable, for the purposes of this description and the following claims, if they differ by no more than approximately +/−10% coefficient of variation (CV), preferably by less than approximately +/−5% CV, more preferably +/−2% CV. These constraints should be observed over the entire range of concentration levels to be measured associated with the relevant biological condition. While it is thus necessary for various embodiments herein to satisfy criteria that measurements are achieved under measurement conditions that are substantially repeatable and wherein specificity and efficiencies of amplification for all constituents are substantially similar, nevertheless, it is within the scope of the present invention as claimed herein to achieve such measurement conditions by adjusting assay results that do not satisfy these criteria directly, in such a manner as to compensate for errors, so that the criteria are satisfied after suitable adjustment of assay results.

In practice, tests are run to assure that these conditions are satisfied. For example, the design of all primer-probe sets are done in house, experimentation is performed to determine which set gives the best performance. Even though primer-probe design can be enhanced using computer techniques known in the art, and notwithstanding common practice, it has been found that experimental validation is still useful. Moreover, in the course of experimental validation, the selected primer-probe combination is associated with a set of features:

The reverse primer should be complementary to the coding DNA strand. In one embodiment, the primer should be located across an intron-exon junction, with not more than four bases of the three-prime end of the reverse primer complementary to the proximal exon. (If more than four bases are complementary, then it would tend to competitively amplify genomic DNA.)

In an embodiment of the invention, the primer probe set should amplify cDNA of less than 110 bases in length and should not amplify, or generate fluorescent signal from, genomic DNA or transcripts or cDNA from related but biologically irrelevant loci.

A suitable target of the selected primer probe is first strand cDNA, which may be prepared, in one embodiment, is described as follows:

(a) Use of Whole Blood for Ex Vivo Assessment of a Biological Condition Affected by an Agent.

Human blood is obtained by venipuncture and prepared for assay by separating samples for baseline, no exogenous stimulus, and pro-inflammatory stimulus with sufficient volume for at least three time points. Typical pro-inflammatory stimuli include lipopolysaccharide (LPS), phytohemagglutinin (PHA) heat-killed staphylococci (HKS), carrageean, IL-2 plus toxic shock syndrome toxin-1 (TSST1), or cytokine cocktails, and may be used individually or in combination. The aliquots of heparinized, whole blood are mixed with additional test therapeutic compounds and held at 37° C. in an atmosphere of 5% $CO_2$ for 30 minutes. Stimulus is added at varying concentrations, mixed and held loosely capped at 37° C. for the prescribed timecourse. At defined times, cells are lysede and RNA extracted by various standard means.

Nucleic acids, RNA and or DNA are purified from cells, tissues or fluids of the test population of cells or indicator cell lines. RNA is preferentially obtained from the nucleic acid mix using a variety of standard procedures (or RNA Isolation Strategies, pp. 55-104, in *RNA Methodologies, A laboratory guide for isolation and characterization,* 2nd edition, 1998, Robert E. Farrell, Jr., Ed., Academic Press), in the present using a filter-based RNA isolation system from Ambion (RNAqueous™, Phenol-free Total RNA Isolation Kit, Catalog #1912, version 9908; Austin, Tex.).

In accordance with one procedure, the whole blood assay for Gene Expression Profiles determination was carried out as follows: Human whole blood was drawn into 10 mL Vacutainer tubes with Sodium Heparin. Blood samples were mixed by gently inverting tubes 4-5 times. The blood was used within 10-15 minutes of draw. In the experiments, blood was diluted 2-fold, i.e. per sample per time point, 0.6 mL whole blood+0.6 mL stimulus. The assay medium was prepared and the stimulus added as appropriate.

A quantity (0.6 mL) of whole blood was then added into each 12×75 mm polypropylene tube. 0.6 mL of 2× LPS (from *E. coli* serotype 0127:B8, Sigma#L3880 or serotype 055, Sigma #L4005, 10 ng/mL, subject to change in different lots) into LPS tubes was added. Next, 0.6 mL assay medium was added to the "control" tubes. The caps were closed tightly. The tubes were inverted 2-3 times to mix samples. Caps were loosened to first stop and the tubes incubated at 37° C., 5% $CO_2$ for 6 hours. At 6 hours, samples were gently mixed to resuspend blood cells, and 0.15 mL was removed from each tube (using a micropipettor with barrier tip), and transferred to 0.15 mL of lysis buffer and mixed. Lysed samples were extracted using an ABI 6100 Nucleic Acid Prepstation following the manufacturer's recommended protocol.

The samples were then centrifuged for 5 min at 500× g, ambient temperature (IEC centrifuge or equivalent, in microfuge tube adapters in swinging bucket), and as much serum from each tube was removed as possible and discarded. Cell pellets were placed on ice; and RNA extracted as soon as possible using an Ambion RNAqueous kit.

(b) Amplification Strategies.

Specific RNAs are amplified using message specific primers or random primers. The specific primers are synthesized from data obtained from public databases (e.g., Unigene, National Center for Biotechnology Information, National Library of Medicine, Bethesda, Md.), including information from genomic and cDNA libraries obtained from humans and other animals. Primers are chosen to preferentially amplify from specific RNAs obtained from the test or indicator samples (see, for example, RT PCR, Chapter 15 in *RNA Methodologies, A laboratory guide for isolation and characterization,* 2nd edition, 1998, Robert E. Farrell, Jr., Ed., Academic Press; or Chapter 22 pp. 143-151, *RNA isolation and characterization protocols,* Methods in molecular biology, Volume 86, 1998, R. Rapley and D. L. Manning Eds., Human Press, or 14 in Statistical refinement of primer design parameters, Chapter 5, pp. 55-72, PCR applications: protocols for functional genomics, M. A. Innis, D. H. Gelfand and J. J. Sninsky, Eds., 1999, Academic Press). Amplifications are carried out in either isothermic conditions or using a thermal cycler (for example, a ABI 9600 or 9700 or 7900 obtained from Applied Biosystems, Foster City, Calif.; see Nucleic acid detection methods, pp. 1-24, in *Molecular methods for virus detection,* D. L. Wiedbrauk and D. H., Farkas, Eds., 1995, Academic Press). Amplified nucleic acids are detected using fluorescent-tagged detection oligonucleotide probes (see, for example, Taqman™ PCR Reagent Kit, Protocol, part number 402823 revision A, 1996, Applied Biosystems, Foster City Calif.) that are identified and synthesized from publicly known databases as described for the amplification primers. In the present case, amplified cDNA is detected and quantified using the ABI Prism 7900 Sequence Detection System obtained from Applied Biosystems (Foster City, Calif.). Amounts of specific RNAs contained in the test sample or obtained from the indicator cell lines can be related to the relative quantity of fluorescence observed (see for example, Advances in quantitative PCR technology: 5' nuclease assays, Y. S. Lie and C. J. Petropolus, Current Opinion in Biotechnology, 1998, 9:43-48, or Rapid thermal cycling and PCR kinetics, pp. 211-229, chapter 14 in PCR applications: protocols for functional genomics, M. A. Innis, D. H. Gelfand and J. J. Sninsky, Eds., 1999, Academic Press).

As a particular implementation of the approach described here in detail is a procedure for synthesis of first strand cDNA for use in PCR. This procedure can be used for both whole blood RNA and RNA extracted from cultured cells (i.e. THP-1 cells).

Materials

1. Applied Biosystems TAQMAN Reverse Transcription Reagents Kit (P/N 808-0234). Kit Components: 10× TaqMan RT Buffer, 25 mM Magnesium chloride, deoxyNTPs mixture, Random Hexamers, RNase Inhibitor, MultiScribe Reverse Transcriptase (50 U/mL) (2) RNase/DNase free water (DEPC Treated Water from Ambion (P/N 9915G), or equivalent)

Methods

1. Place RNase Inhibitor and MultiScribe Reverse Transcriptase on ice immediately. All other reagents can be thawed at room temperature and then placed on ice.

2. Remove RNA samples from −80° C. freezer and thaw at room temperature and then place immediately on ice.

3. Prepare the following cocktail of Reverse Transcriptase Reagents for each 100 mL RT reaction (for multiple samples, prepare extra cocktail to allow for pipetting error):

| 1 reaction (mL) | | 11X, e.g. 10 samples (μL) |
|---|---|---|
| 10X RT Buffer | 10.0 | 110.0 |
| 25 mM MgCl$_2$ | 22.0 | 242.0 |
| dNTPs | 20.0 | 220.0 |
| Random Hexamers | 5.0 | 55.0 |
| RNAse Inhibitor | 2.0 | 22.0 |
| Reverse Transcriptase | 2.5 | 27.5 |
| Water | 18.5 | 203.5 |
| Total: | 80.0 | 880.0 |
| | | (80 μL per sample) |

4. Bring each RNA sample to a total volume of 20 μL in a 1.5 mL microcentrifuge tube (for example, for THP-1 RNA, remove 10 μL RNA and dilute to 20 μL with RNase/DNase free water, for whole blood RNA use 20 μL total RNA) and add 80 μL RT reaction mix from step 5, 2, 3. Mix by pipetting up and down.

5. Incubate sample at room temperature for 10 minutes.
6. Incubate sample at 37° C. for 1 hour.
7. Incubate sample at 90° C. for 10 minutes.
8. Quick spin samples in microcentrifuge.
9. Place sample on ice if doing PCR immediately, otherwise store sample at −20° C. for future use.
10. PCR QC should be run on all RT samples using 18S and b-actin (see SOP 200-020).

The use of the primer probe with the first strand cDNA as described above to permit measurement of constituents of a Gene Expression Panel is as follows:

Set up of a 24-gene Human Gene Expression Panel for Inflammation.

Materials 1. 20× Primer/Probe Mix for each gene of interest.
2. 20× Primer/Probe Mix for 18S endogenous control.
3. 2× Taqman Universal PCR Master Mix.
4. cDNA transcribed from RNA extracted from cells.
5. Applied Biosystems 96-Well Optical Reaction Plates.
6. Applied Biosystems Optical Caps, or optical-clear film.
7. Applied Biosystem Prism 7700 or 7900 Sequence Detector.

Methods

1. Make stocks of each Primer/Probe mix containing the Primer/Probe for the gene of interest, Primer/Probe for 18S endogenous control, and 2× PCR Master Mix as follows. Make sufficient excess to allow for pipetting error e.g., approximately 10% excess. The following example illustrates a typical set up for one gene with quadruplicate samples testing two conditions (2 plates).

| | 1X (1 well) (μL) |
|---|---|
| 2X Master Mix | 7.5 |
| 20X 18S Primer/Probe Mix | 0.75 |
| 20X Gene of interest Primer/Probe Mix | 0.75 |
| Total | 9.0 |

2. Make stocks of cDNA targets by diluting 95 μL of cDNA into 2000 μL of water. The amount of cDNA is adjusted to give Ct values between 10 and 18, typically between 12 and 16.

3. Pipette 9 μL of Primer/Probe mix into the appropriate wells of an Applied Biosystems 384-Well Optical Reaction Plate.
4. Pipette 10 μL of cDNA stock solution into each well of the Applied Biosystems 384-Well Optical Reaction Plate.
5. Seal the plate with Applied Biosystems Optical Caps, or optical-clear film.
6. Analyze the plate on the ABI Prism 7900 Sequence Detector.

Methods herein may also be applied using proteins where sensitive quantitative techniques, such as an Enzyme Linked ImmunoSorbent Assay (ELISA) or mass spectroscopy, are available and well-known in the art for measuring the amount of a protein constituent. (see WO 98/24935 herein incorporated by reference).

Baseline Profile Data Sets

The analyses of samples from single individuals and from large groups of individuals provide a library of profile data sets relating to a particular panel or series of panels. These profile data sets may be stored as records in a library for use as baseline profile data sets. As the term "baseline" suggests, the stored baseline profile data sets serve as comparators for providing a calibrated profile data set that is informative about a biological condition or agent. Baseline profile data sets may be stored in libraries and classified in a number of cross-referential ways. One form of classification may rely on the characteristics of the panels from which the data sets are derived. Another form of classification may be by particular biological condition, e.g., rheumatoid arthritis. The concept of biological condition encompasses any state in which a cell or population of cells may be found at any one time. This state may reflect geography of samples, sex of subjects or any other discriminator. Some of the discriminators may overlap. The libraries may also be accessed for records associated with a single subject or particular clinical trial. The classification of baseline profile data sets may further be annotated with medical information about a particular subject, a medical condition, and/or a particular agent.

The choice of a baseline profile data set for creating a calibrated profile data set is related to the biological condition to be evaluated, monitored, or predicted, as well as, the intended use of the calibrated panel, e.g., as to monitor drug development, quality control or other uses. It may be desirable to access baseline profile data sets from the same subject for whom a first profile data set is obtained or from different subject at varying times, exposures to stimuli, drugs or complex compounds; or may be derived from like or dissimilar populations or sets of subjects. The baseline profile data set may be normal, healthy baseline.

The profile data set may arise from the same subject for which the first data set is obtained, where the sample is taken at a separate or similar time, a different or similar site or in a different or similar biological condition. For example, a sample may be taken before stimulation or after stimulation with an exogenous compound or substance, such as before or after therapeutic treatment. The profile data set obtained from the unstimulated sample may serve as a baseline profile data set for the sample taken after stimulation. The baseline data set may also be derived from a library containing profile data sets of a population or set of subjects having some defining characteristic or biological condition. The baseline profile data set may also correspond to some ex vivo or in vitro properties associated with an in vitro cell culture. The resultant calibrated profile data sets may then be stored as a record in a database or library along with or separate from the baseline profile data base and optionally the first profile data set although the first profile data set would normally become incorporated into a baseline profile data set under suitable classification criteria. The remarkable consistency of Gene Expression Profiles associated with a given biological condition makes it valuable to store profile data, which can be used, among other things for normative reference purposes. The normative reference can serve to indicate the degree to which a subject conforms to a given biological condition (healthy or diseased) and, alternatively or in addition, to provide a target for clinical intervention.

Selected baseline profile data sets may be also be used as a standard by which to judge manufacturing lots in terms of efficacy, toxicity, etc. Where the effect of a therapeutic agent is being measured, the baseline data set may correspond to Gene Expression Profiles taken before administration of the agent. Where quality control for a newly manufactured product is being determined, the baseline data set may correspond with a gold standard for that product. However, any suitable normalization techniques may be employed. For example, an average baseline profile data set is obtained from authentic material of a naturally grown herbal nutriceutical and compared over time and over different lots in order to demonstrate consistency, or lack of consistency, in lots of compounds prepared for release.

Calibrated Data

Given the repeatability achieved in measurement of gene expression, described above in connection with "Gene Expression Panels" and "gene amplification", it was concluded that where differences occur in measurement under such conditions, the differences are attributable to differences in biological condition. Thus, it has been found that calibrated profile data sets are highly reproducible in samples taken from the same individual under the same conditions. Similarly, it has been found that calibrated profile data sets are reproducible in samples that are repeatedly tested. Also found have been repeated instances wherein calibrated profile data sets obtained when samples from a subject are exposed ex vivo to a compound are comparable to calibrated profile data from a sample that has been exposed to a sample in vivo. Importantly, it has been determined that an indicator cell line treated with an agent can in many cases provide calibrated profile data sets comparable to those obtained from in vivo or ex vivo populations of cells. Moreover, it has been determined that administering a sample from a subject onto indicator cells can provide informative calibrated profile data sets with respect to the biological condition of the subject including the health, disease states, therapeutic interventions, aging or exposure to environmental stimuli or toxins of the subject.

Calculation of Calibrated Profile Data Sets and Computational Aids

The calibrated profile data set may be expressed in a spreadsheet or represented graphically for example, in a bar chart or tabular form but may also be expressed in a three dimensional representation. The function relating the baseline and profile data may be a ratio expressed as a logarithm. The constituent may be itemized on the x-axis and the logarithmic scale may be on the y-axis. Members of a calibrated data set may be expressed as a positive value representing a relative enhancement of gene expression or as a negative value representing a relative reduction in gene expression with respect to the baseline.

Each member of the calibrated profile data set should be reproducible within a range with respect to similar samples taken from the subject under similar conditions. For example, the calibrated profile data sets may be reproducible within one order of magnitude with respect to similar samples taken from the subject under similar conditions. More particularly, the members may be reproducible within 20%, and typically within 10%. In accordance with embodiments of the invention, a pattern of increasing, decreasing and no change in relative gene expression from each of a plurality of gene loci examined in the Gene Expression Panel may be used to prepare a calibrated profile set that is informative with regards to a biological condition, biological efficacy of an agent treatment conditions or for comparison to populations or sets of subjects or samples, or for comparison to populations of cells. Patterns of this nature may be used to identify likely candidates for a drug trial, used alone or in combination with other clinical indicators to be diagnostic or prognostic with respect to a biological condition or may be used to guide the development of a pharmaceutical or nutriceutical through manufacture, testing and marketing.

The numerical data obtained from quantitative gene expression and numerical data from calibrated gene expression relative to a baseline profile data set may be stored in databases or digital storage mediums and may retrieved for purposes including managing patient health care or for conducting clinical trials or for characterizing a drug. The data may be transferred in physical or wireless networks via the World Wide Web, email, or internet access site for example or by hard copy so as to be collected and pooled from distant geographic sites.

The method also includes producing a calibrated profile data set for the panel, wherein each member of the calibrated profile data set is a function of a corresponding member of the first profile data set and a corresponding member of a baseline profile data set for the panel, and wherein the baseline profile data set is related to the rheumatoid arthritis or inflammatory conditions related to rheumatoid arthritis to be evaluated, with the calibrated profile data set being a comparison between the first profile data set and the baseline profile data set, thereby providing evaluation of the rheumatoid arthritis or inflammatory conditions related to rheumatoid arthritis of the subject.

In yet other embodiments, the function is a mathematical function and is other than a simple difference, including a second function of the ratio of the corresponding member of first profile data set to the corresponding member of the baseline profile data set, or a logarithmic function. In related embodiments, each member of the calibrated profile data set has biological significance if it has a value differing by more than an amount D, where $D=F(1.1)-F(0.9)$, and F is the second function. In such embodiments, the first sample is obtained and the first profile data set quantified at a first location, and the calibrated profile data set is produced using a network to access a database stored on a digital storage medium in a second location, wherein the database may be updated to reflect the first profile data set quantified from the sample. Additionally, using a network may include accessing a global computer network.

In an embodiment of the present invention, a descriptive record is stored in a single database or multiple databases where the stored data includes the raw gene expression data (first profile data set) prior to transformation by use of a baseline profile data set, as well as a record of the baseline profile data set used to generate the calibrated profile data set including for example, annotations regarding whether the baseline profile data set is derived from a particular Signature Panel and any other annotation that facilitates interpretation and use of the data.

Because the data is in a universal format, data handling may readily be done with a computer. The data is organized so as to provide an output optionally corresponding to a graphical representation of a calibrated data set.

For example, a distinct sample derived from a subject being at least one of RNA or protein may be denoted as PI. The first profile data set derived from sample PI is denoted Mj, where Mj is a quantitative measure of a distinct RNA or protein constituent of PI. The record Ri is a ratio of M and P and may be annotated with additional data on the subject relating to, for example, age, diet, ethnicity, gender, geographic location, medical disorder, mental disorder, medication, physical activity, body mass and environmental exposure. Moreover, data handling may further include accessing data from a second condition database which may contain additional medical data not presently held with the calibrated profile data sets. In this context, data access may be via a computer network.

The above described data storage on a computer may provide the information in a form that can be accessed by a user. Accordingly, the user may load the information onto a second access site including downloading the information. However, access may be restricted to users having a password or other security device so as to protect the medical records contained within. A feature of this embodiment of the invention is the ability of a user to add new or annotated records to the data set so the records become part of the biological information.

The graphical representation of calibrated profile data sets pertaining to a product such as a drug provides an opportunity for standardizing a product by means of the calibrated profile, more particularly a signature profile. The profile may be used as a feature with which to demonstrate relative efficacy, differences in mechanisms of actions, etc. compared to other drugs approved for similar or different uses.

The various embodiments of the invention may be also implemented as a computer program product for use with a computer system. The product may include program code for deriving a first profile data set and for producing calibrated profiles. Such implementation may include a series of computer instructions fixed either on a tangible medium, such as a computer readable medium (for example, a diskette, CD-ROM, ROM, or fixed disk), or transmittable to a computer system via a modem or other interface device, such as a communications adapter coupled to a network. The network coupling may be for example, over optical or wired communications lines or via wireless techniques (for example, microwave, infrared or other transmission techniques) or some combination of these. The series of computer instructions preferably embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (for example, shrink wrapped software), pre-loaded with a computer system (for example, on system ROM or fixed disk), or distributed from a server or electronic bulletin board over a network (for example, the Internet or World Wide Web). In addition, a computer system is further provided including derivative modules for deriving a first data set and a calibration profile data set.

The calibration profile data sets in graphical or tabular form, the associated databases, and the calculated index or derived algorithm, together with information extracted from the panels, the databases, the data sets or the indices or algorithms are commodities that can be sold together or separately for a variety of purposes as described in WO 01/25473.

In other embodiments, a clinical indicator may be used to assess the rheumatoid arthritis or inflammatory conditions related to rheumatoid arthritis of the relevant set of subjects by interpreting the calibrated profile data set in the context of at least one other clinical indicator, wherein the at least one other clinical indicator is selected from the group consisting of blood chemistry, urinalysis, X-ray or other radiological or metabolic imaging technique, other chemical assays, and physical findings.

Index Construction

In combination, (i) the remarkable consistency of Gene Expression Profiles with respect to a biological condition across a population or set of subject or samples, or across a population of cells and (ii) the use of procedures that provide substantially reproducible measurement of constituents in a Gene Expression Panel giving rise to a Gene Expression Profile, under measurement conditions wherein specificity and efficiencies of amplification for all constituents of the panel are substantially similar, make possible the use of an index that characterizes a Gene Expression Profile, and which therefore provides a measurement of a biological condition.

An index may be constructed using an index function that maps values in a Gene Expression Profile into a single value that is pertinent to the biological condition at hand. The values in a Gene Expression Profile are the amounts of each constituent of the Gene Expression Panel that corresponds to the Gene Expression Profile. These constituent amounts form a profile data set, and the index function generates a single value—the index—from the members of the profile data set.

The index function may conveniently be constructed as a linear sum of terms, each term being what is referred to herein as a "contribution function" of a member of the profile data set. For example, the contribution function may be a constant times a power of a member of the profile data set. So the index function would have the form $$I = \Sigma C_i M_i P(i,$$

where I is the index, Mi is the value of the member i of the profile data set, Ci is a constant, and P(i) is a power to which Mi is raised, the sum being formed for all integral values of i up to the number of members in the data set. We thus have a linear polynomial expression.

The values Ci and P(i) may be determined in a number of ways, so that the index I is informative of the pertinent biological condition. One way is to apply statistical techniques, such as latent class modeling, to the profile data sets to correlate clinical data or experimentally derived data, or other data pertinent to the biological condition. In this connection, for example, may be employed the software from Statistical Innovations, Belmont, Mass., called Latent Gold®. Alternatively, other simpler modeling techniques may be employed in a manner known in the art. The index function for inflammation may be constructed, for example, in a manner that a greater degree of inflammation (as determined by the profile data set for the Inflammation Gene Expression Panel included in Tables 1 and 2) correlates with a large value of the index function. In a simple embodiment, therefore, each P(i) may be +1 or −1, depending on whether the constituent increases or decreases with increasing inflammation. As discussed in further detail below, a meaningful inflammation index that is proportional to the expression, referred to herein as IR-105, was constructed as follows:

$$\frac{1}{4}\{IL1A\}+\frac{1}{4}\{IL1B\}+\frac{1}{4}\{TNF\}+\frac{1}{4}\{INFG\}-1/\{IL10\},$$

where the braces around a constituent designate measurement of such constituent and the constituents are a subset of the Inflammation Gene Expression Panel included in Tables 1 and 2.

Just as a baseline profile data set, discussed above, can be used to provide an appropriate normative reference, and can even be used to create a Calibrated profile data set, as discussed above, based on the normative reference, an index that characterizes a Gene Expression Profile can also be provided with a normative value of the index function used to create the index. This normative value can be determined with respect to a relevant population or set of subjects or samples or to a relevant population of cells, so that the index may be interpreted in relation to the normative value. The relevant population or set of subjects or samples, or relevant population of cells may have in common a property that is at least one of age range, gender, ethnicity, geographic location, nutritional history, medical condition, clinical indicator, medication, physical activity, body mass, and environmental exposure.

As an example, the index can be constructed, in relation to a normative Gene Expression Profile for a population or set of healthy subjects, in such a way that a reading of approximately 1 characterizes normative Gene Expression Profiles of healthy subjects. Let us further assume that the biological condition that is the subject of the index is inflammation; a reading of 1 in this example thus corresponds to a Gene Expression Profile that matches the norm for healthy subjects. A substantially higher reading then may identify a subject experiencing an inflammatory condition. The use of 1 as identifying a normative value, however, is only one possible choice; another logical choice is to use 0 as identifying the normative value. With this choice, deviations in the index from zero can be indicated in standard deviation units (so that values lying between −1 and +1 encompass 90% of a normally distributed reference population or set of subjects. Since it was determined that Gene Expression Profile values (and accordingly constructed indices based on them) tend to be normally distributed, the 0-centered index constructed in this manner is highly informative. It therefore facilitates use of the index in diagnosis of disease and setting objectives for treatment. The choice of 0 for the normative value, and the use of standard deviation units, for example, are illustrated in FIG. 4B, discussed below.

Still another embodiment is a method of providing an index that is indicative of rheumatoid arthritis or inflammatory conditions related to rheumatoid arthritis of a subject based on a first sample from the subject, the first sample providing a source of RNAs, the method comprising deriving from the first sample a profile data set, the profile data set including a plurality of members, each member being a quantitative measure of the amount of a distinct RNA constituent in a panel of constituents selected so that measurement of the constituents is indicative of the presumptive signs of rheumatoid arthritis, the panel including at least two of the constituents of any of the genes listed in the Inflammation Gene Expression Panel included in Tables 1 and 2. In deriving the profile data set, such measure for each constituent is achieved under measurement conditions that are substantially repeatable, at least one measure from the profile data set is applied to an index function that provides a mapping from at least one measure of the profile data set into one measure of the presumptive signs of rheumatoid arthritis, so as to produce an index pertinent to the rheumatoid arthritis or inflammatory conditions related to the rheumatoid arthritis of the subject.

As another embodiment of the invention, an index function I of the form $$I=C_0+\Sigma C_i M_{1i}^{P1(i)} M_{2i}^{P2(i)},$$

can be employed, where $M_1$ and $M_2$ are values of the member i of the profile data set, $C_i$ is a constant determined without reference to the profile data set, and P1 and P2 are powers to which $M_1$ and $M_2$ are raised. For example, when P1=P2=0, the index function is simply the sum of constants; when P1=1 and P2=0, the index function is a linear expression; when P1=P2=1, the index function is a quadratic expression. As discussed in further detail below, a quadratic expression that is constructed as a meaningful identifier of Rheumatoid Arthritis (RA) is the following:

$$C_0+C_1\{TLR2\}+C_2\{CD4\}+C_3\{NFKB1\}+\\C_4\{TLR2\}\{CD4\}+C_5\{TLR2\}\{NFKB1\}+\\C_6\{NFKB1\}^2+C_7\{TLR2\}^2+C_8\{CD4\}^2.$$

where the constant Co serves to calibrate this expression to the biological population of interest (such as RA), that is characterized by inflammation. In this embodiment, when the index value equals 0, the odds are 50:50 of I the subject being RA vs normal. More generally, the predicted odds of being RA is $[\exp(I_i)]$, and therefore the predicted probability of being RA is $[\exp(I_i)]/[I+\exp((I_i)]$. Thus, when the index exceeds 0, the predicted probability that a subject is RA is higher than 0.5, and when it falls below 0, the predicted probability is less than 0.5.

The value of $C_0$ may be adjusted to reflect the prior probability of being in this population based on known exogenous risk factors for the subject. In an embodiment where $C_0$ is adjusted as a function of the subject's risk factors, where the subject has prior probability pi of being RA based on such risk factors, the adjustment is made by increasing (decreasing) the unadjusted $C_0$ value by adding to $C_0$ the natural logarithm of the ratio of the prior odds of being RA taking into account the risk factors to the overall prior odds of being RA without taking into account the risk factors.

It was determined that the above quadratic expression for RA may be well approximated by a linear expression of the form:

$$D_0+D_1\{TLR2\}+D_2\{CD4\}+D_3\{NFKB1\}.$$

Kits

The invention also includes an RA-detection reagent, i.e., nucleic acids that specifically identify one or more rheumatoid arthritis or inflammatory condition related to rheumatoid arthritis nucleic acids (e.g., any gene listed in Tables 1-2 and Tables 4-10; sometimes referred to herein as RA-associated genes) by having homologous nucleic acid sequences, such as oligonucleotide sequences, complementary to a portion of the RA-associated genes nucleic acids or antibodies to proteins encoded by the RA-associated genes nucleic acids packaged together in the form of a kit. The oligonucleotides can be fragments of the RA-associated genes. For example the oligonucleotides can be 200, 150, 100, 50, 25, 10 or less nucleotides in length. The kit may contain in separate containers a nucleic acid or antibody (either already bound to a solid matrix or packaged separately with reagents for binding them to the matrix), control formulations (positive and/or negative), and/or a detectable label. Instructions (i.e., written, tape, VCR, CD-ROM, etc.) for carrying out the assay may be included in the kit. The assay may for example be in the form of PCR, a Northern hybridization or a sandwich ELISA, as known in the art.

For example, RA-associated genes detection reagents can be immobilized on a solid matrix such as a porous strip to form at least one RA-associated genes detection site. The measurement or detection region of the porous strip may include a plurality of sites containing a nucleic acid. A test strip may also contain sites for negative and/or positive controls. Alternatively, control sites can be located on a separate strip from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of RA-associated genes present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences represented by RA-associated genes (see Tables 1-2 and Tables 4-10). In various embodiments, the expression of 2, 3, 4, 5, 6, 7, 8, 9, 10, 15, 20, 25, 40 or 50 or more of the sequences represented by RA-associated genes (see Tables 1-2 and Tables 4-10) can be identified by virtue of binding to the array. The substrate array can be on, i.e., a solid substrate, i.e., a "chip" as described in U.S. Pat. No. 5,744,305. Alternatively, the substrate array can be a solution array, i.e., Luminex, Cyvera, Vitra and Quantum Dots' Mosaic.

The skilled artisan can routinely make antibodies, nucleic acid probes, i.e., oligonucleotides, aptamers, siRNAs, anti sense oligonucleotides, against any of the RA-associated genes listed in Tables 1-2 and Tables 4-10.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

EXAMPLES

In the Examples below, subjects having "active RA" were selected on the basis of the following criteria: 6 or more swollen joints, 9 or more tender joints, CRP>2 mg/dL, and may require introduction of more aggressive therapy. Subjects suffering from RA and described as being "stable" indicate that the subject was responsive to the therapeutic being administered. Subjects suffering from RA and described as being "unstable" that their disease was not responding to the therapeutic being administered, and whose therapeutic was scheduled to be changed.

Example 1

Development and Use of Population Normative Values for Gene Expression Profiles

FIG. 1A shows the arithmetic mean values for gene expression profiles (using 48 loci of the Inflammation Gene Expression Panel included in Tables 1 and 2) obtained from whole blood of two distinct patient populations (patient sets). These patient sets are both normal or undiagnosed. The first patient set, which is identified as Bonfils (the plot points for which are represented by diamonds), was composed of 17 subjects accepted as blood donors at the Bonfils Blood Center in Denver, Colo. The second patient set was composed of 16 donors, for which Gene Expression Profiles were obtained from assays conducted four times over a four-week period. Subjects in this second patient set (plot points for which are represented by squares) were recruited from employees of Source Precision Medicine, Inc., the assignee herein. Gene expression averages for each population were calculated for each of 48 gene loci of the Inflammation Gene Expression Panel included in Tables 1 and 2. The results for loci 1-24 (sometimes referred to below as the Inflammation 48A loci) are shown in FIG. 1A and for loci 25-48 (sometimes referred to below as the Inflammation 48B loci) are shown in FIG. 1B.

The consistency between gene expression levels of the two distinct patient sets is dramatic. Both patient sets show gene expressions for each of the 48 loci that are not significantly different from each other. This observation suggests that there is a "normal" expression pattern for human inflammatory genes, that a Gene Expression Profile, using the Inflammation Gene Expression Panel included in Tables 1 and 2 (or a subset thereof) characterizes that expression pattern, and that a population-normal expression pattern can be used, for example, to guide medical intervention for any biological condition that results in a change from the normal expression pattern.

Figure 2:
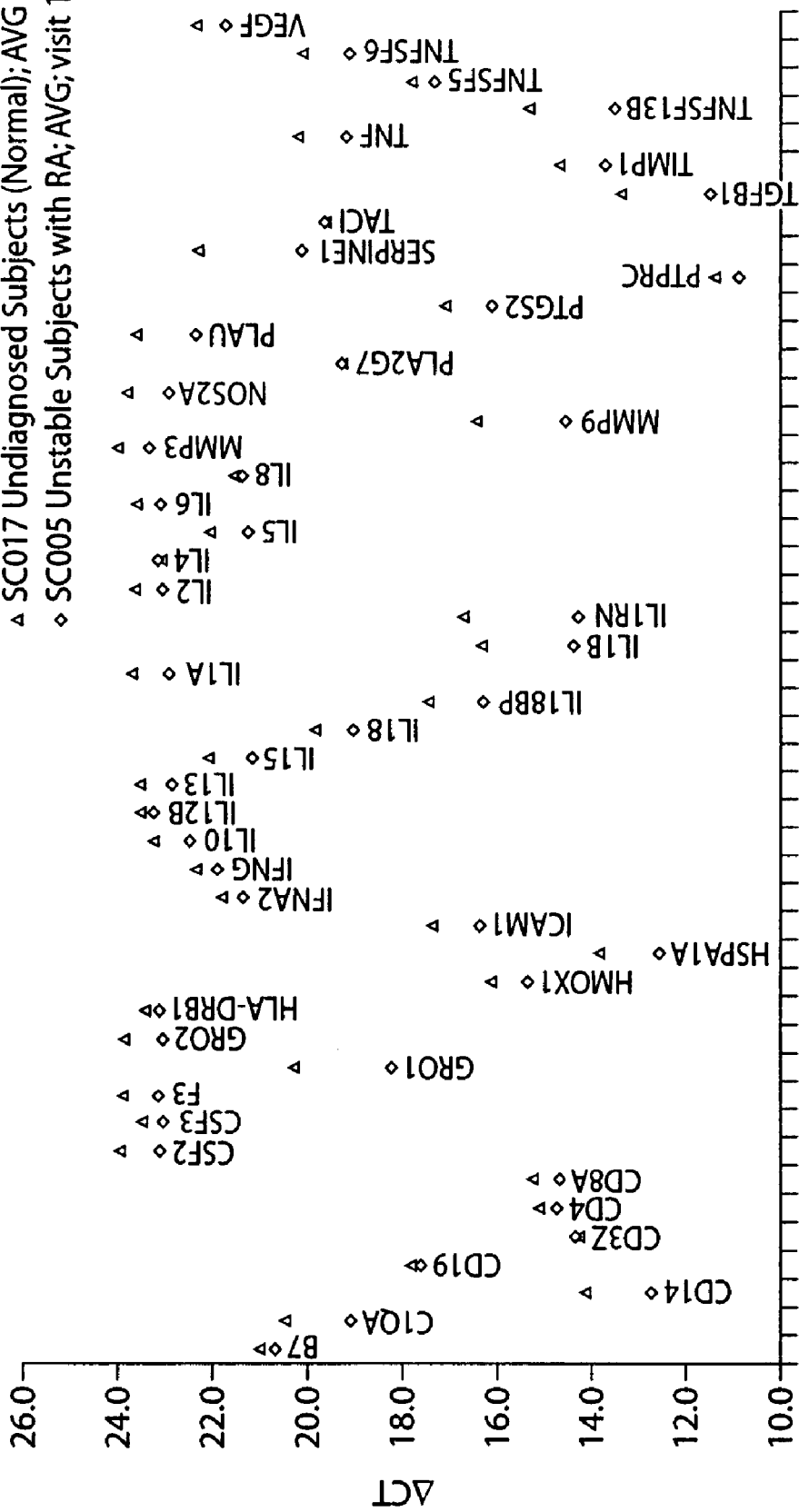
FIG. 2 compares a normal population with a rheumatoid arthritis population derived from a longitudinal study.

In a similar vein, FIG. 2 shows arithmetic mean values for gene expression profiles (again using the 48 loci of the Inflammation Gene Expression Panel included in Tables 1 and 2) also obtained from whole blood of two distinct patient populations (patient sets). One patient set, expression values for which are represented by triangular data points, was 24 normal, undiagnosed subjects (who therefore had no known inflammatory disease). The other patient set, the expression values for which are represented by diamond-shaped data points, was four patients with rheumatoid arthritis and who have failed therapy (who therefore had unstable rheumatoid arthritis).

Figure 1B:
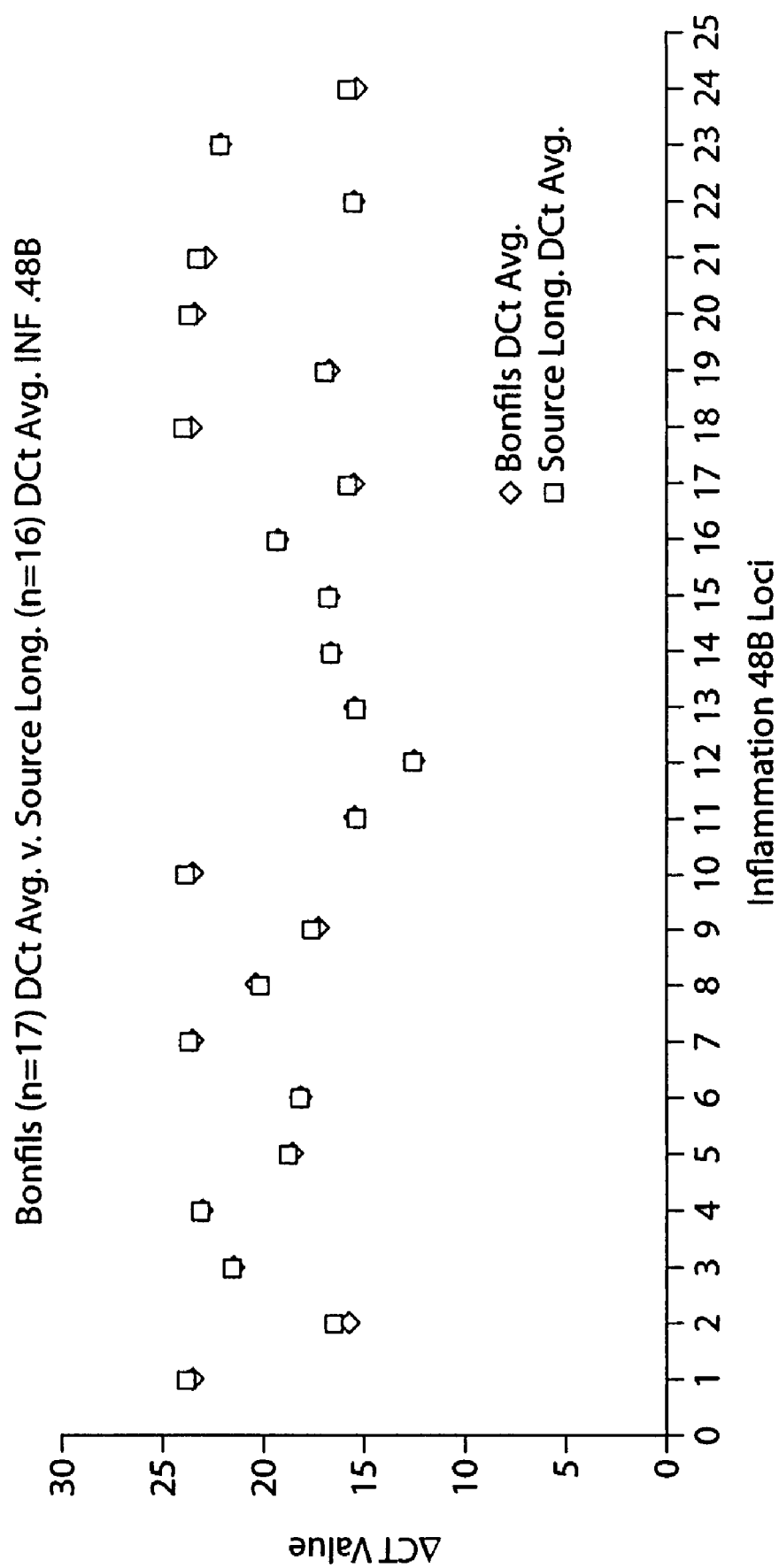

As remarkable as the consistency of data from the two distinct normal patient sets shown in FIGS. 1A and 1B was the systematic divergence of data from the normal and diseased patient sets shown in FIG. 2. In 45 of the shown 48 inflammatory gene loci, subjects with unstable rheumatoid arthritis showed, on average, increased inflammatory gene expression (lower cycle threshold values; Ct), than subjects without disease. The data thus further demonstrate that is possible to identify groups with specific biological conditions using gene expression if the precision and calibration of the underlying assay are carefully designed and controlled according to the teachings herein.

Example 2

Figure 3:
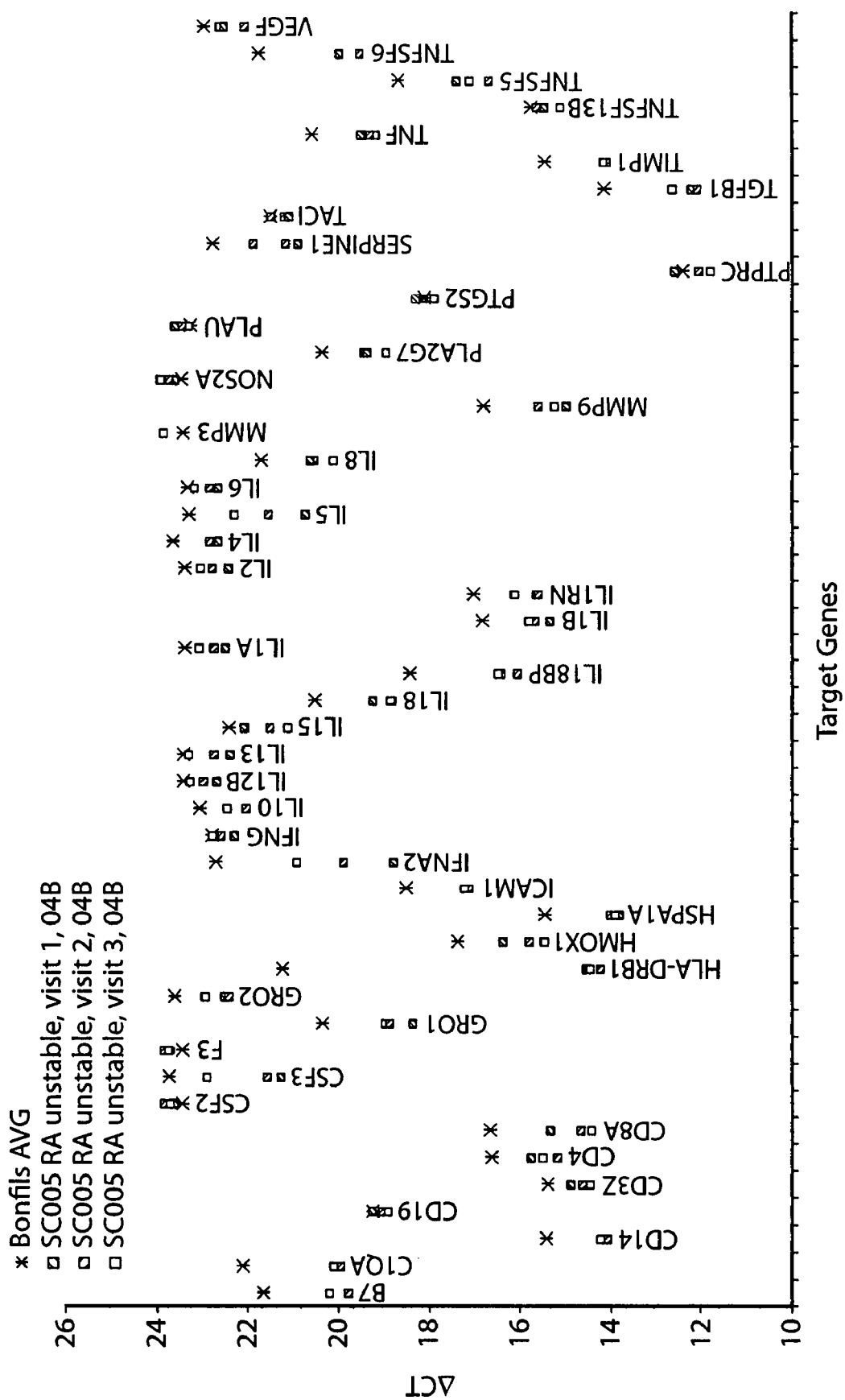
FIG. 3 also shows the effect over time, on inflammatory gene expression in a single human subject suffering from rheumatoid arthritis, of the administration of a TNF-inhibiting compound, but here the expression is shown in comparison to the cognate locus average previously determined for the normal (i.e., undiagnosed, healthy) population.

Consistency of Expression Values of Constituents in Gene Expression Panels Over Time as Reliable Indicators of Biological Condition FIG. 3 also shows the effect over time, on inflammatory gene expression in a single human subject suffering from rheumatoid arthritis, of the administration of a TNF-inhibiting compound, but here the expression is shown in comparison to the cognate locus average previously determined for the normal (i.e., undiagnosed, healthy) patient set. As part of a larger international study involving patients with rheumatoid arthritis, the subject was followed over a twelve-week period. The subject was enrolled in the study because of a failure to respond to conservative drug therapy for rheumatoid arthritis and a plan to change therapy and begin immediate treatment with a TNF-inhibiting compound. Blood was drawn from the subject prior to initiation of new therapy (visit 1). After initiation of new TNF-inhibiting therapy, blood was drawn at 4 weeks post change in therapy (visit 2), 8 weeks (visit 3), and 12 weeks (visit 4) following the start of new therapy. Blood was collected using the PAXgene Blood RNA System™, held at room temperature for two hours and then frozen at −30° C.

Frozen samples were shipped to the central laboratory at Source Precision Medicine, the assignee herein, in Boulder, Colo. for determination of expression levels of genes in the 48-gene inflammation gene expression panel included in Tables 1 and 2. The blood samples were thawed and RNA extracted according to the manufacturer's recommended procedure. RNA was converted to cDNA and the level of expression of the 48 inflammatory genes was determined. Expression results are shown for 11 of the 48 loci in FIG. 3. When the expression results for the 11 loci are compared from visit one to a population average of normal blood donors from the United States, the subject shows considerable difference. Similarly, gene expression levels at each of the subsequent physician visits for each locus are compared to the same normal average value. Data from visits 2, 3 and 4 document the effect of the change in therapy. In each visit following the change in the therapy, the level of inflammatory gene expression for 10 of the 11 loci is closer to the cognate locus average previously determined for the normal (i.e., undiagnosed, healthy) patient set.

Figure 4A:
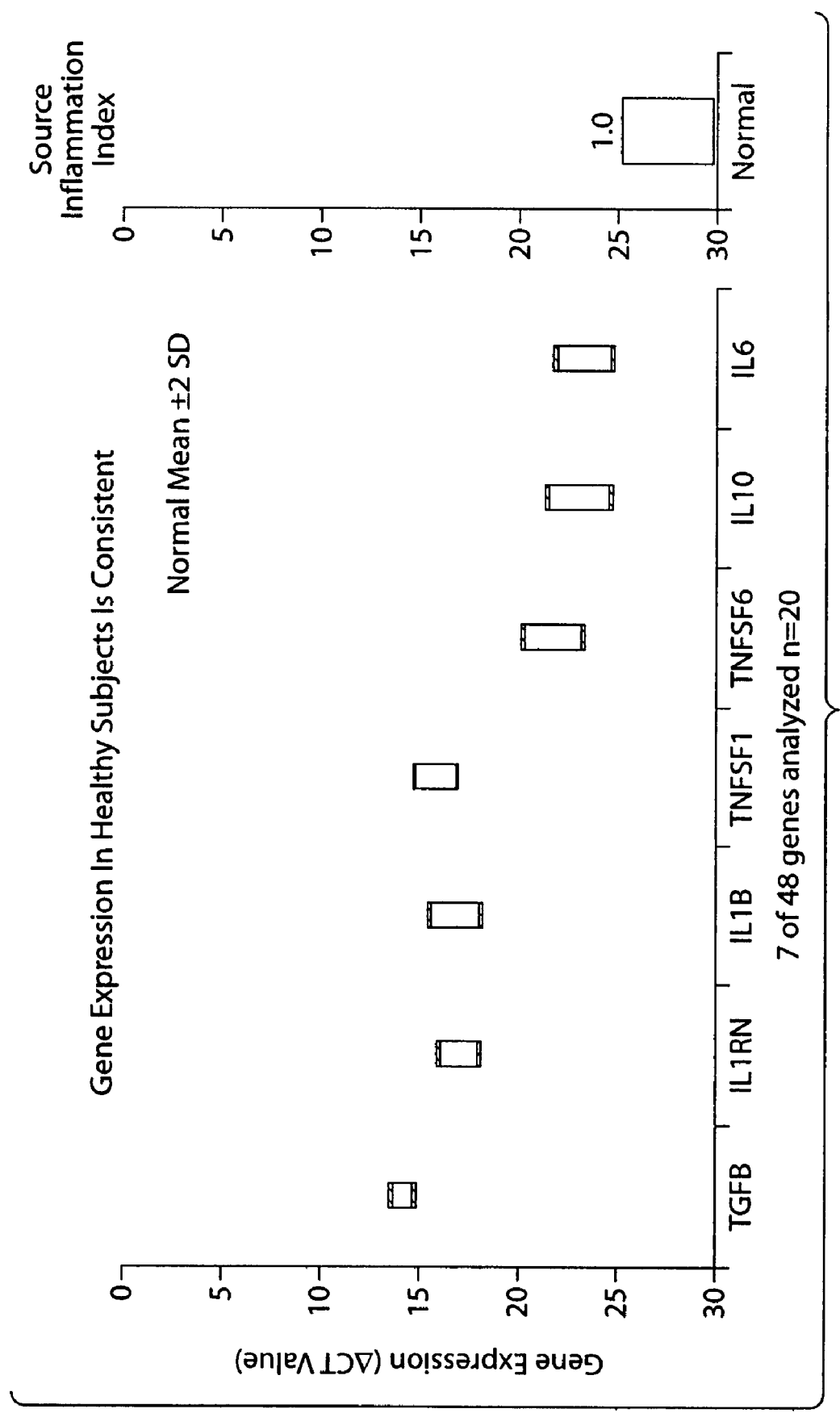
FIG. 4A further illustrates the consistency of inflammatory gene expression in a population.
Figure 4B:
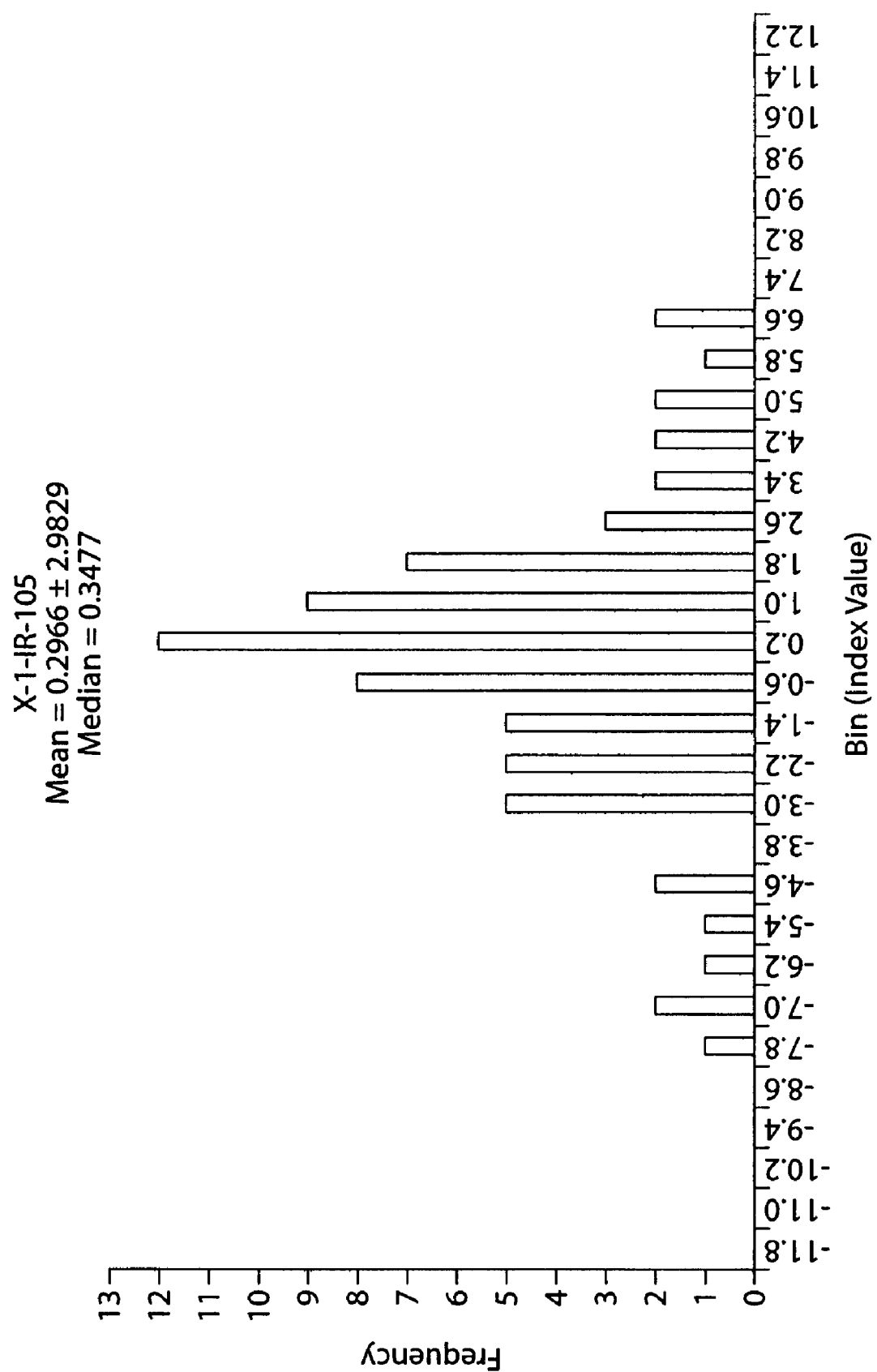
FIG. 4B shows the normal distribution of index values obtained from an undiagnosed population.

FIG. 4A further illustrates the consistency of inflammatory gene expression, illustrated here with respect to 7 loci of (of the Inflammation Gene Expression Panel included in Tables 1 and 2), in a set of 44 normal, undiagnosed blood donors. For each individual locus is shown the range of values lying within ±2 standard deviations of the mean expression value, which corresponds to 95% of a normally distributed population. Notwithstanding the great width of the confidence interval (95%), the measured gene expression value (ΔCt)—remarkably—still lies within 10% of the mean, regardless of the expression level involved. As described in further detail below, for a given biological condition an index can be constructed to provide a measurement of the condition. This is possible as a result of the conjunction of two circumstances: (i) there is a remarkable consistency of Gene Expression Profiles with respect to a biological condition across a population and (ii) there can be employed procedures that provide substantially reproducible measurement of constituents in a Gene Expression Panel giving rise to a Gene Expression Profile, under measurement conditions wherein specificity and efficiencies of amplification for all constituents of the panel are substantially similar and which therefore provides a measurement of a biological condition. Accordingly, a function of the expression values of representative constituent loci of FIG. 4A is here used to generate an inflammation index value, which is normalized so that a reading of 1 corresponds to constituent expression values of healthy subjects, as shown in the right-hand portion of FIG. 4A.

In FIG. 4B, an inflammation index value was determined for each member of a set of 42 normal undiagnosed blood donors, and the resulting distribution of index values, shown in the figure, can be seen to approximate closely a normal distribution, notwithstanding the relatively small subject set size. The values of the index are shown relative to a 0-based median, with deviations from the median calibrated in standard deviation units. Thus 90% of the subject set lies within +1 and −1 of a 0 value. We have constructed various indices, which exhibit similar behavior.

Figure 4C:
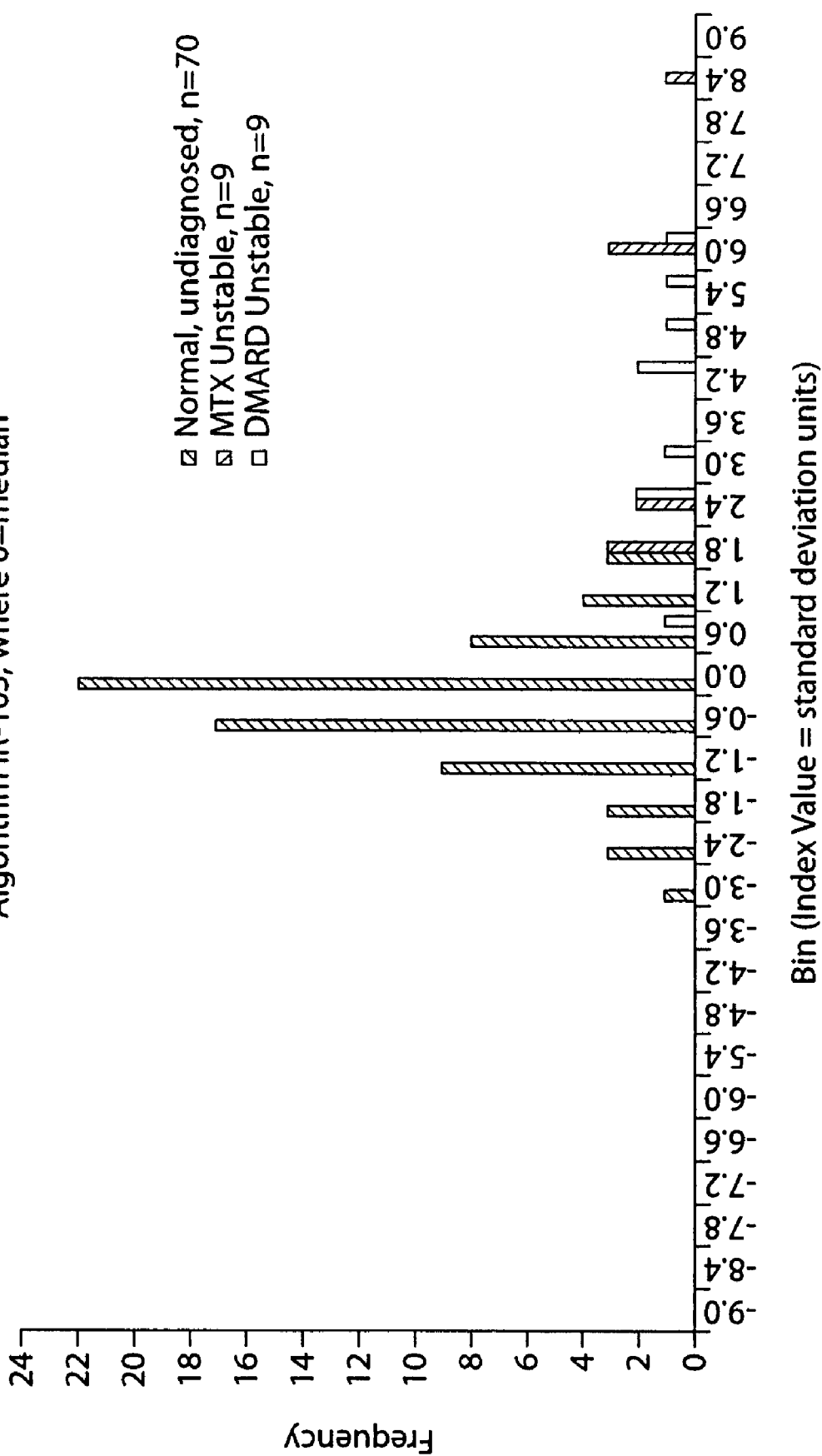
FIG. 4C illustrates the use of the same index as FIG. 4B, where the inflammation median for a normal population has been set to zero and both normal and diseased subjects are plotted in standard deviation units relative to that median.

FIG. 4C illustrates the use of the same index as FIG. 4B, where the inflammation median for a normal population of subjects has been set to zero and both normal and diseased subjects are plotted in standard deviation units relative to that median. An inflammation index value was determined for each member of a normal, undiagnosed population of 70 individuals (black bars). The resulting distribution of index values, shown in FIG. 4C, can be seen to approximate closely a normal distribution. Similarly, index values were calculated for individuals from two diseased population groups, (1) rheumatoid arthritis patients treated with methotrexate (MTX) who are about to change therapy to more efficacious drugs (e.g., TNF inhibitors)(hatched bars), and (2) rheumatoid arthritis patients treated with disease modifying anti-rheumatoid drugs (DMARDS) other than MTX, who are about to change therapy to more efficacious drugs (e.g., MTX). Both populations of subjects present index values that are skewed upward (demonstrating increased inflammation) in comparison to the normal distribution. This figure thus illustrates the utility of an index to derived from Gene Expression Profile data to evaluate disease status and to provide an objective and quantifiable treatment objective. When these two populations of subjects were treated appropriately, index values from both populations returned to a more normal distribution (data not shown here).

Figure 5:
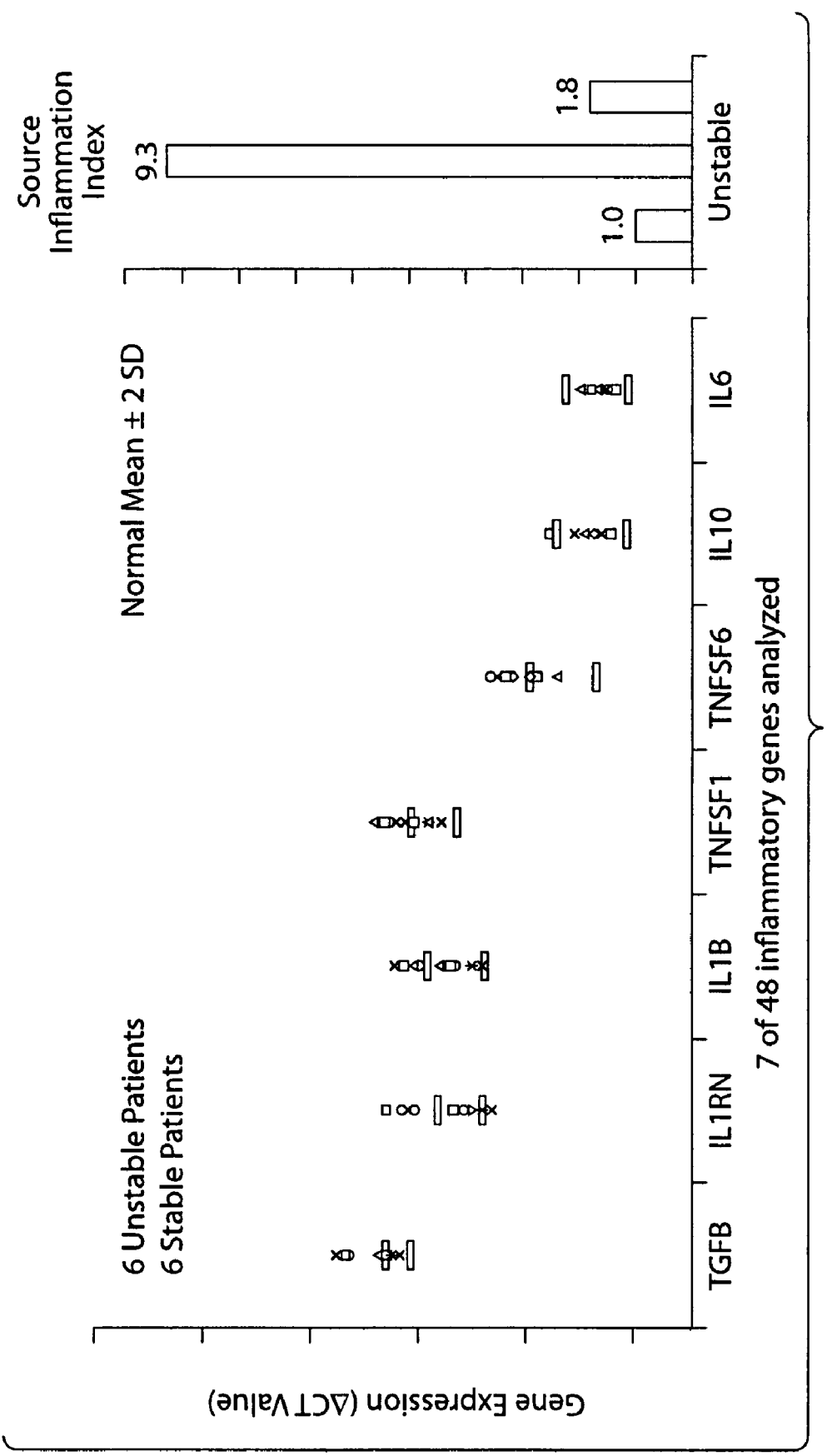
FIG. 5 plots, in a fashion similar to that of FIG. 4A, Gene Expression Profiles, for the same 7 loci as in FIG. 4A, two different (responder v. non-responder) 6-subject populations of rheumatoid arthritis patients.

FIG. 5 plots, in a fashion similar to that of FIG. 4A, Gene Expression Profiles, for the same 7 loci as in FIG. 4A, two different 6-subject populations of rheumatoid arthritis patients. One population (called "stable" in the figure) is of patients who have responded well to treatment and the other population (called "unstable" in the figure) is of patients who have not responded well to treatment and whose therapy is scheduled for change. It can be seen that the expression values for the stable patient population, lie within the range of the 95% confidence interval, whereas the expression values for the unstable patient population for 5 of the 7 loci are outside and above this range. The right-hand portion of the figure shows an average inflammation index of 9.3 for the unstable population and an average inflammation index of 1.8 for the stable population, compared to 1 for a normal undiagnosed population of patients. The index thus provides a measure of the extent of the underlying inflammatory condition, in this case, rheumatoid arthritis. Hence the index, besides providing a measure of biological condition, can be used to measure the effectiveness of therapy as well as to provide a target for therapeutic intervention.

Figure 6:
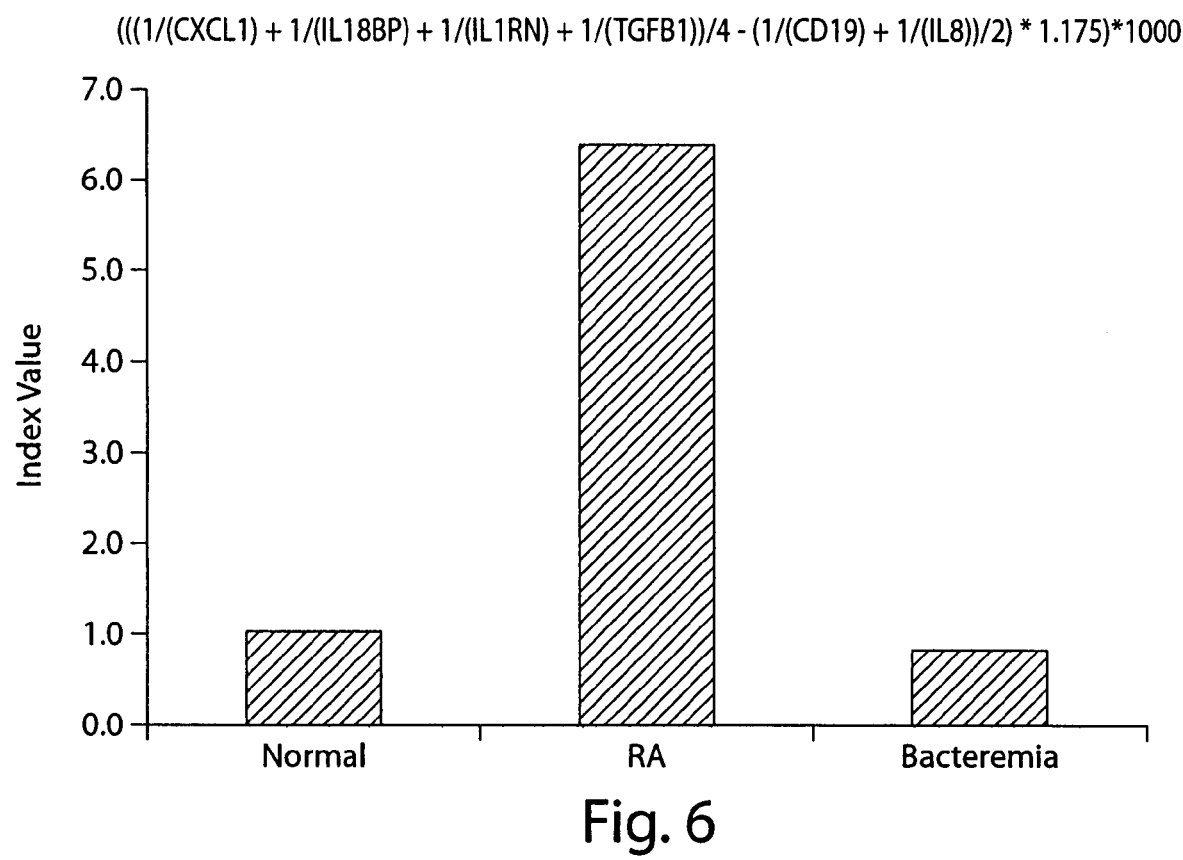
FIG. 6 illustrates application of an algorithm (shown in the figure), providing an index pertinent to rheumatoid arthritis (RA) as applied respectively to normal subjects, RA patients, and bacteremia patients.

An algorithm specific for rheumatoid arthritis (shown in FIG. 6) useful for distinguishing between subjects afflicted with rheumatoid arthritis versus normal subjects or other diseased subjects was applied. As can be seen in FIG. 6, the index easily distinguishes RA subjects from both normal subjects and subjects suffering from a disease other than RA (e.g., bacteremia subjects).

Example 3

Experimental Design for Evaluating Rheumatoid Arthritis: Assessing Response to Therapeutic Treatment In a series of studies, the inflammation index was used to assess response to therapeutic treatment by individuals suffering from rheumatoid arthritis, or inflammatory conditions induced or related to rheumatoid arthritis.

Figure 7:
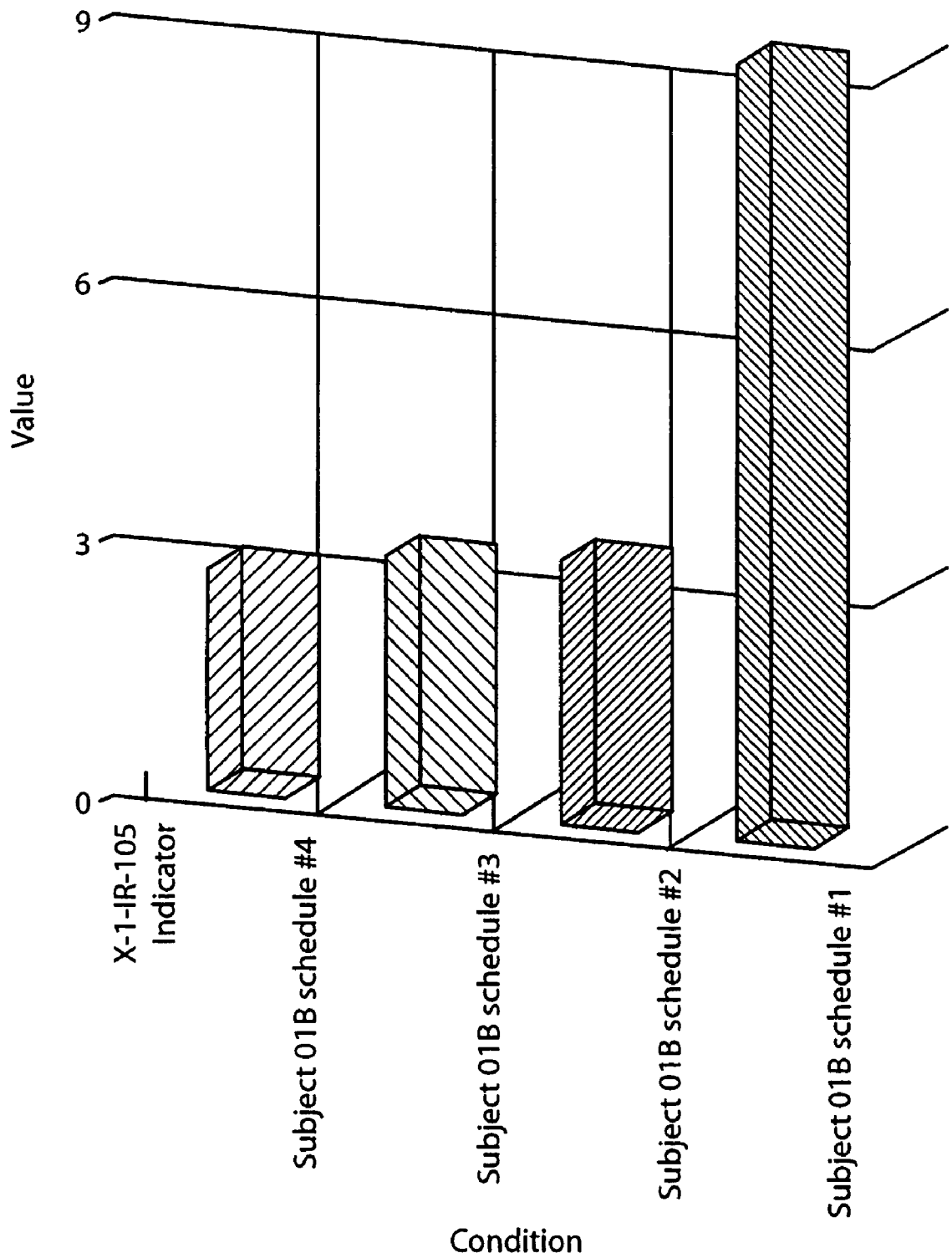
FIG. 7 thus illustrates use of the inflammation index for assessment of a single subject suffering from rheumatoid arthritis, who has not responded well to traditional therapy with methotrexate.

In one study, the inflammation index was used to assess a single subject suffering from rheumatoid arthritis, who has not responded well to traditional therapy with methotrexate. The results are depicted in FIG. 7, where the inflammation index for this subject is shown on the far right of the graph at the start of a new therapy (a TNF inhibitor), and then, moving leftward, successively, 2 weeks, 6 weeks, and 12 weeks thereafter. As can be seen from FIG. 7, the index can be seen moving towards normal, consistent with physician observation of the patient as responding to the new treatment.

Figure 8:
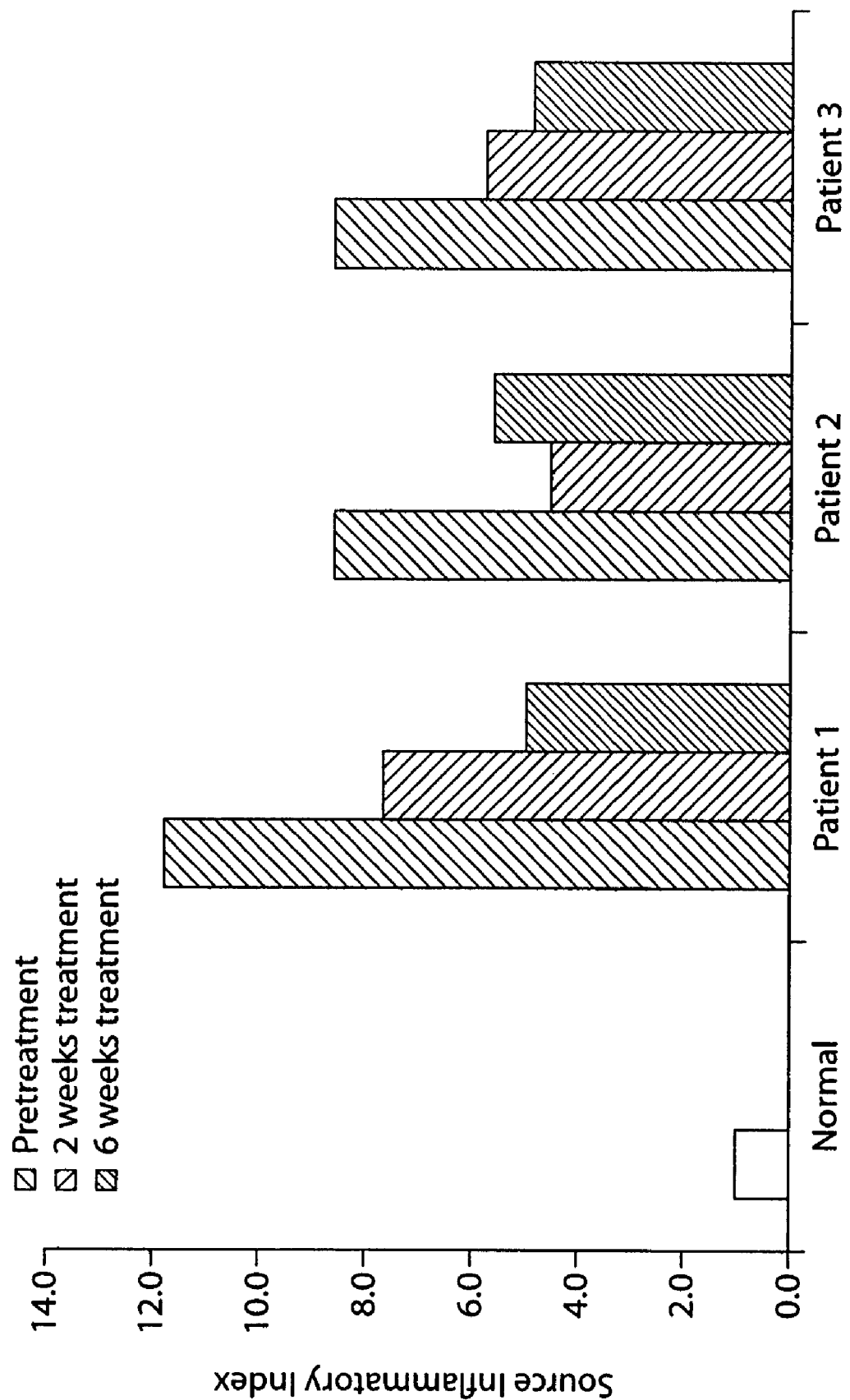
FIG. 8 similarly illustrates use of the inflammation index for assessment of three subjects suffering from rheumatoid arthritis, who have not responded well to traditional therapy with methotrexate.

In a similar study, the inflammation index was used to assess three subjects suffering from rheumatoid arthritis, who have not responded well to traditional therapy with methotrexate, at the beginning of new treatment (also with a TNF inhibitor), and 2 weeks and 6 weeks thereafter. The results are depicted in FIG. 8, where the index in each case can again be seen moving generally towards normal, consistent with physician observation of the patients as responding to the new treatment.

Figure 9:
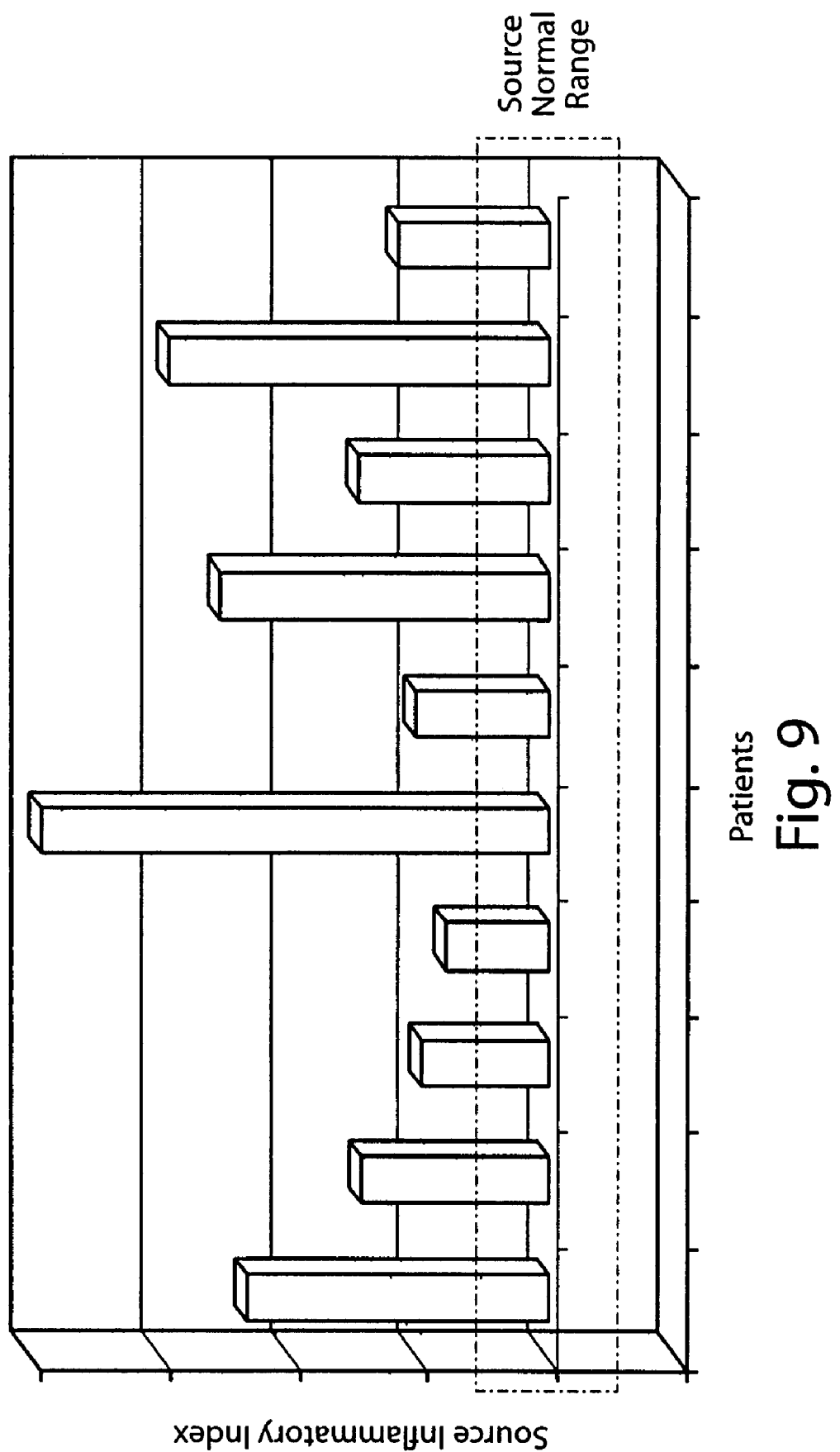
FIGS. 9-11 show the inflammation index for an international group of subjects, suffering from rheumatoid arthritis, undergoing three separate treatment regimens.
Figure 10:
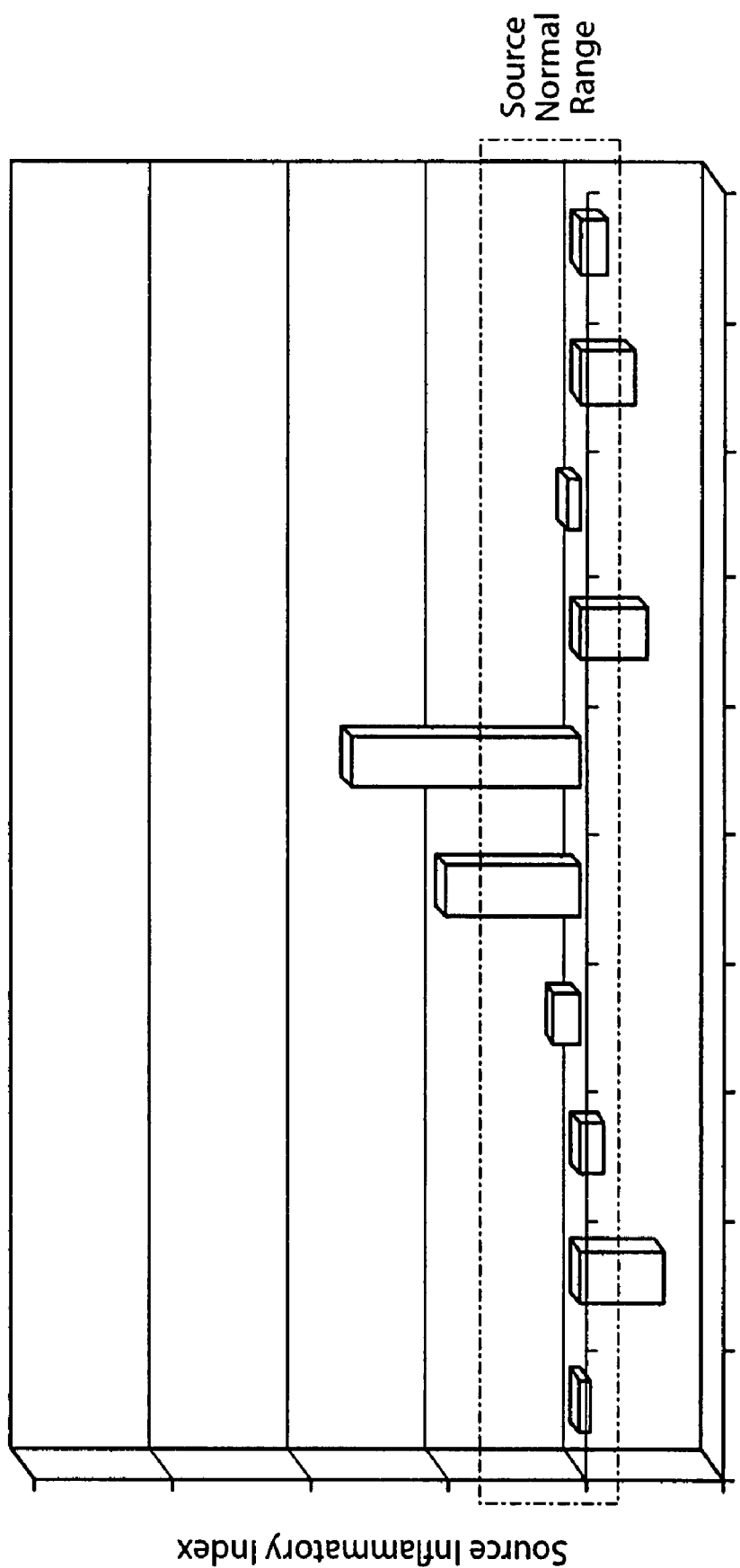
Figure 11:
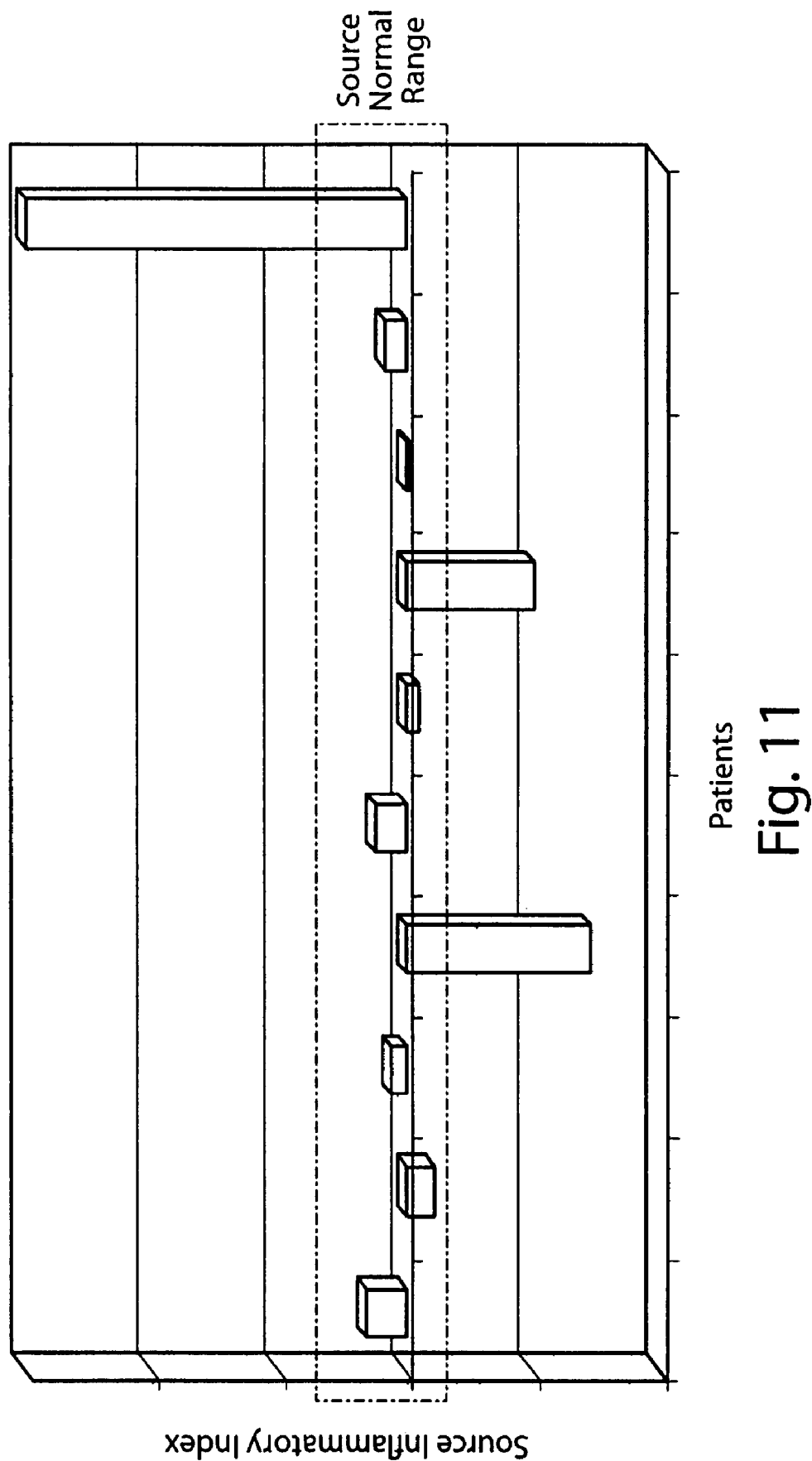

In another study, the inflammation index was used to assess three groups of ten international subjects suffering from RA, each of whom has been characterized as stable (that is, not anticipated to be subjected to a change in therapy) by the subject's treating physician, and each group having been treated with either methotrexate, Enbrel (a TNF inhibitor), or Remicade (another TNF inhibitor). The results are depicted in FIGS. 9-11. FIG. 9 shows the index for each of 10 patients in the group being treated with methotrexate, which known to alleviate symptoms without addressing the underlying disease. FIG. 10 shows the index for each of 10 patients in the group being treated with Enbrel, and FIG. 11 shows the index for each 10 patients being treated with Remicade. It can be seen that the inflammation index for each of the patients in FIG. 9 is elevated compared to normal, whereas in FIG. 10, the patients being treated with Enbrel as a class have an inflammation index that comes much closer to normal (80% in the normal range). In FIG. 11, it can be seen that, while all but one of the patients being treated with Remicade have an inflammation index at or below normal, two of the patients have an abnormally low inflammation index, suggesting an immunosuppressive response to this drug. (Indeed, studies have shown that Remicade has been associated with serious infections in some subjects, and here the immunosuppressive effect is quantified.) Also in FIG. 11, one subject has an inflammation index that is significantly above the normal range. This subject in fact was also on a regimen of an anti-inflammation steroid (prednisone) that was being tapered; within approximately one week after the inflammation index was sampled, the subject experienced a significant flare of clinical symptoms.

Remarkably, these examples show a measurement, derived from the assay of blood taken from a subject, pertinent to the subject's arthritic condition. Given that the measurement pertains to the extent of inflammation, it can be expected that other inflammation-based conditions, including, for example, cardiovascular disease, may be monitored in a similar fashion.

In one study, a statistical T-test was applied to identify potential members of a signature gene expression panel that were capable of distinguishing between normal subjects (n=69) and subjects suffering from unstable rheumatoid arthritis (n=23). The results are depicted in FIG. 12, where the grayed boxes show genes that are individually highly effective (T-test P values noted in the box to the right in each case) in distinguishing between the two sets of subjects, and thus indicative of potential members of a signature gene expression panel for rheumatoid arthritis.

FIG. 13 shows a comparison of the change in relative gene expression of 24 patients unstable on Disease Modifying Anti-Rheumatoid Drug (DMARD) therapy, 19 patients stable on DMARD therapy, and 20 patients stable on TNF blockers relative to the mean (ACt) of normal gene expression for 11 genes of interest for RA patients. As can be seen, the relative change in expression, (indicated by X-fold change relative to the mean for normal gene expression) ranges from 3.45-fold greater expression than the mean for MMP9, to 2.23-fold greater expression than the mean for IL10, for patients unstable on DMARD. Perhaps more surprisingly, patients who were stable on DMARD, suggesting that the therapy was successfully treating the RA conditions, showed anywhere from 2.75-fold greater expression than the mean for MMP9 to 1.29-fold greater than the mean for IL10. While not intending to be bound by any theory, these results perhaps suggest that that the DMARD therapy was in fact not treating the underlying condition, but merely treating the symptoms of RA. In fact, for 10 of the 11 genes investigated with this study, all patients, whether unstable on DMARD therapy or stable on DMARD therapy exhibited statistically significant increased gene expression relative to the mean for normal gene expression (see the change in expression for genes MMP9, CD14, TIMP1, HSPA1A, GFB1, IL10, IL1RN, CXCL1, IL1B, and PTGS2). Only the expression of the gene CD 19 was not increased relative to the mean for normal gene expression, and in fact, the values of 0.64 and 0.68 for patient unstable or stable on DMARD, respectively, are statistically significantly lower than the normal expression for this gene. The t-test p values are shown on the right half of this table, indicating which changes in gene expression shown on the left half of the table are statistically significant.

In contrast, for patients being treated with TNF blockers, one can see that the gene expression levels were all within the statistical mean compared to normal gene expression, and the expression levels for IL10, IL1RN, CXCL2, PTGS2, and CD19 were in fact statistically significantly lower than the mean for normal expression levels. While not intending to be bound by any theory, these results support the position that even patients responding to DMARD therapy should be treated more aggressively and placed on TNF blockers earlier. This is strong clinical evidence that traditional DMARD therapy may not, in fact, be treating the underlying cause or condition of rheumatoid arthritis, and that patients so treated are at risk for progression of the disease, if more aggressive therapy, such as treatment with TNF blockers, is not initiated.

FIG. 14 shows gene expression values for 8 genes in 17 patients with Active RA (i.e., each patient had 6 or more swollen joints, 9 or more tender joints, and had CRP at greater than 2 mg/dL), expressed as standard deviation changes from normal. The light-shaded boxes indicate all gene expression values for the various patients that are greater than 2-fold standard deviation units above or below the normal values, and are statistically significant. As can be seen, nearly all of these patients had changes in standard deviation of greater than two for several of the genes investigated. Moreover, using a standard algorithm referred to herein as the IR-105 algorithm (note, statistically derived algorithms are discussed in further detail above) 15 of the 17 patients were assessed with IR-105 values greater than 2, suggesting that these patients could benefit from more aggressive therapy.

FIG. 15 is a study of 22 patients with Active RA (same as for FIG. 14) performed by different rheumatologists on different patients from those in FIG. 14, where similar results are observed. 20 of the 22 patients exhibit changes in standard deviation units that are more than 2-fold greater than the values for normal gene expression. In particular, the values for the genes TGFB1 and TIMP1 are particularly increased in most of the patients. As with the results in FIG. 14, these data suggest that the patients are not responding to the current therapy, as these results look similar to those for patients in FIG. 14 who failed DMARD therapy. Again, these data suggest that more aggressive therapy, in addition to or in place of current treatment, may be in order for these patients.

FIG. 16 displays the gene expression values, expressed in change of standard deviation units relative to normal expression values, for 19 patients who were stable on TNF blockers for 3 months prior to the study. As can be seen, the gene expression values for these patients are almost all within "normal." The exception for patient 01a is explainable and does not dilute the value of this study. Patient 01a was in fact not stable 3 months prior to the study but rather, flared 1 month prior to the study, was treated aggressively with prednisone, and the data for this patient comes from 1 week prior to the flare. These data show the predictive value of gene expression analysis for such patients, since the values for TGFB1, TIMP1 and IL1RN for this patient were higher than they should have been had the patient in fact been stable, but are what might be expected for a patient in an active RA condition.

Similarly, patients 13 and 18 have gene expression values for PTGS2, ILB, and IL1RN that are underexpressed relative to the normal values, suggesting that these patients are trending towards immunosuppression. Again, these data show the predictive value of gene expression analysis for identifying patients at risk for immunosuppression.

FIG. 17 shows the changes in gene expression values relative to normals (n=69 for this study) for 22 patients being treated with kineret or kineret plus sTNF-R1 at baseline, week 4, and termination of the study. The relative expression for 11 of the 12 genes examined were overexpressed at the start of the study, still over-expressed at week 4 but less so, and by the end of the study, 7 genes were still over-expressed to some extent, while 4 genes had transitioned to the underexpressed category (IL1RN, CXCL1, and PTGS2—light boxes). Of interest, the values of CD19 were all under-expressed from the start of the study until the end. It is worth noting that by the end of the study, the expression of PTGS2 (prostaglandin endo-peroxide synthase 2, i.e. COX2), was not statistically significantly different from normal. These data indicate how the gene expression data can track effective therapy in RA patients.

Figure 18:
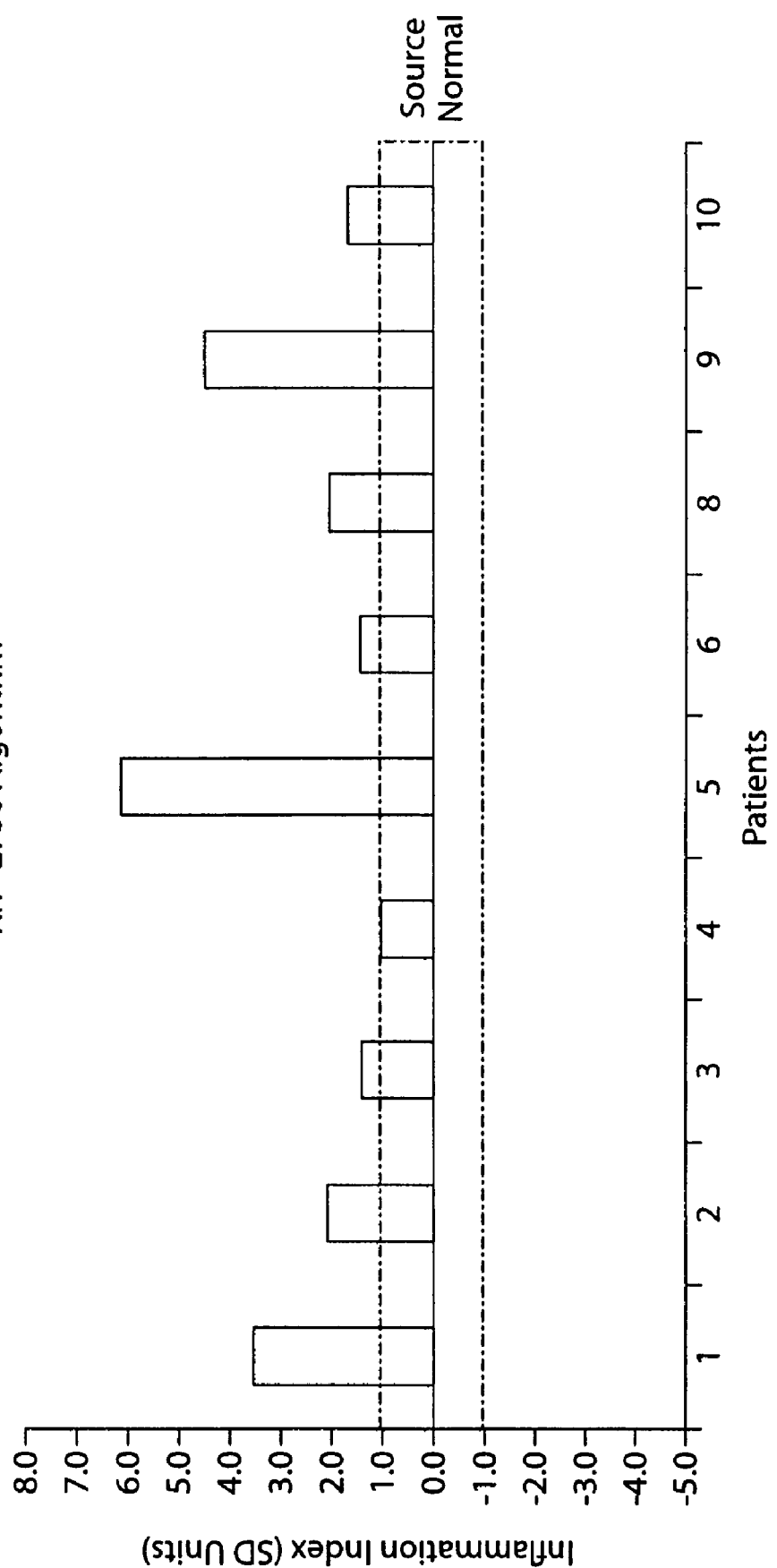
FIG. 18 illustrates inflammation index values for patients clinically stable on methotrexate, at the beginning of the study.
Figure 19:
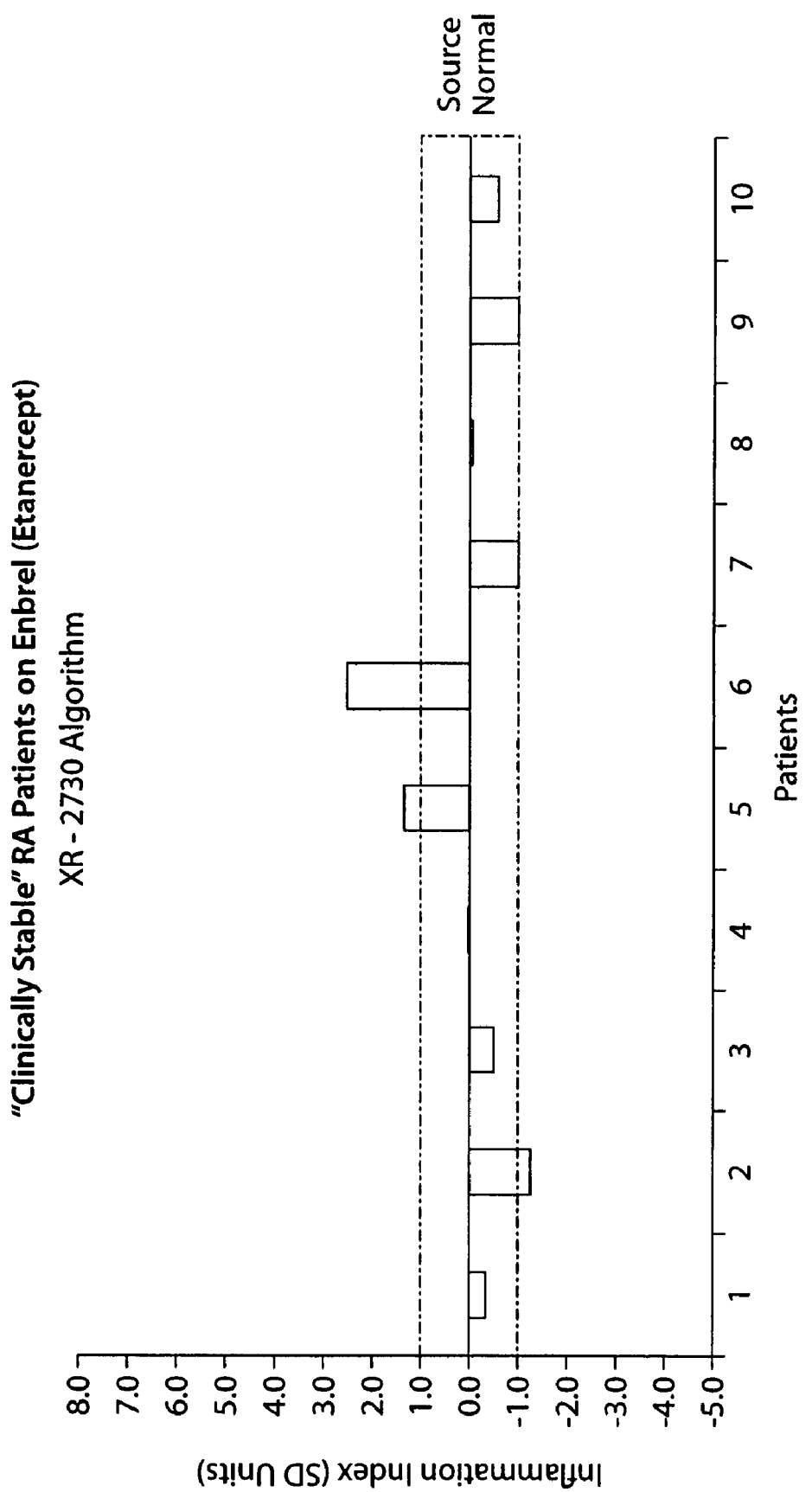
FIG. 19 illustrates inflammation index values for patients clinically stable on TNF inhibitor Enbrel at the beginning of the study.

In another study, a panel of 10 genes known as the Inflammation Index were used to evaluate the gene expression profiles for clinically stable RA patients treated with various therapeutics. The results are depicted in FIGS. 18-22. FIG. 18 shows gene expression values for clinically stable RA patients being treated with methotrexate for a panel of 10 genes known as the Inflammation Index (in standard deviation units).

FIG. 18 shows gene expression values for clinically stable RA patients being treated with enbrel (etanercept) for a panel of 10 genes known as the Inflammation Index (in standard deviation units).

Figure 20:
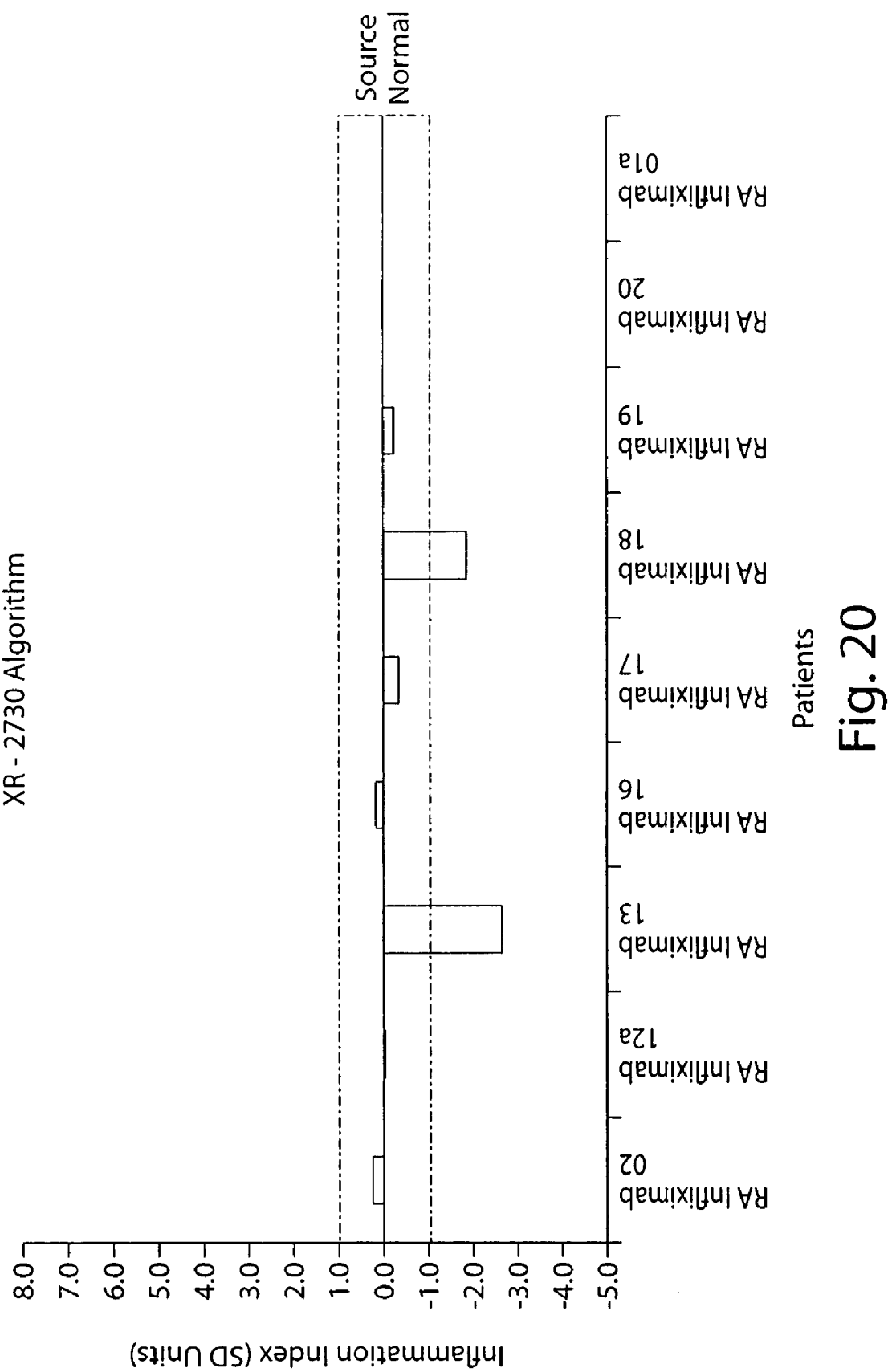
FIG. 20 illustrates inflammation index values for patients clinically stable on the TNF inhibitor Remicade, at the beginning of the study.

FIG. 20 shows gene expression values for clinically stable RA patients being treated with Remicade (infliximab) for a panel of 10 genes known as the Inflammation Index (in standard deviation units).

Figure 21:
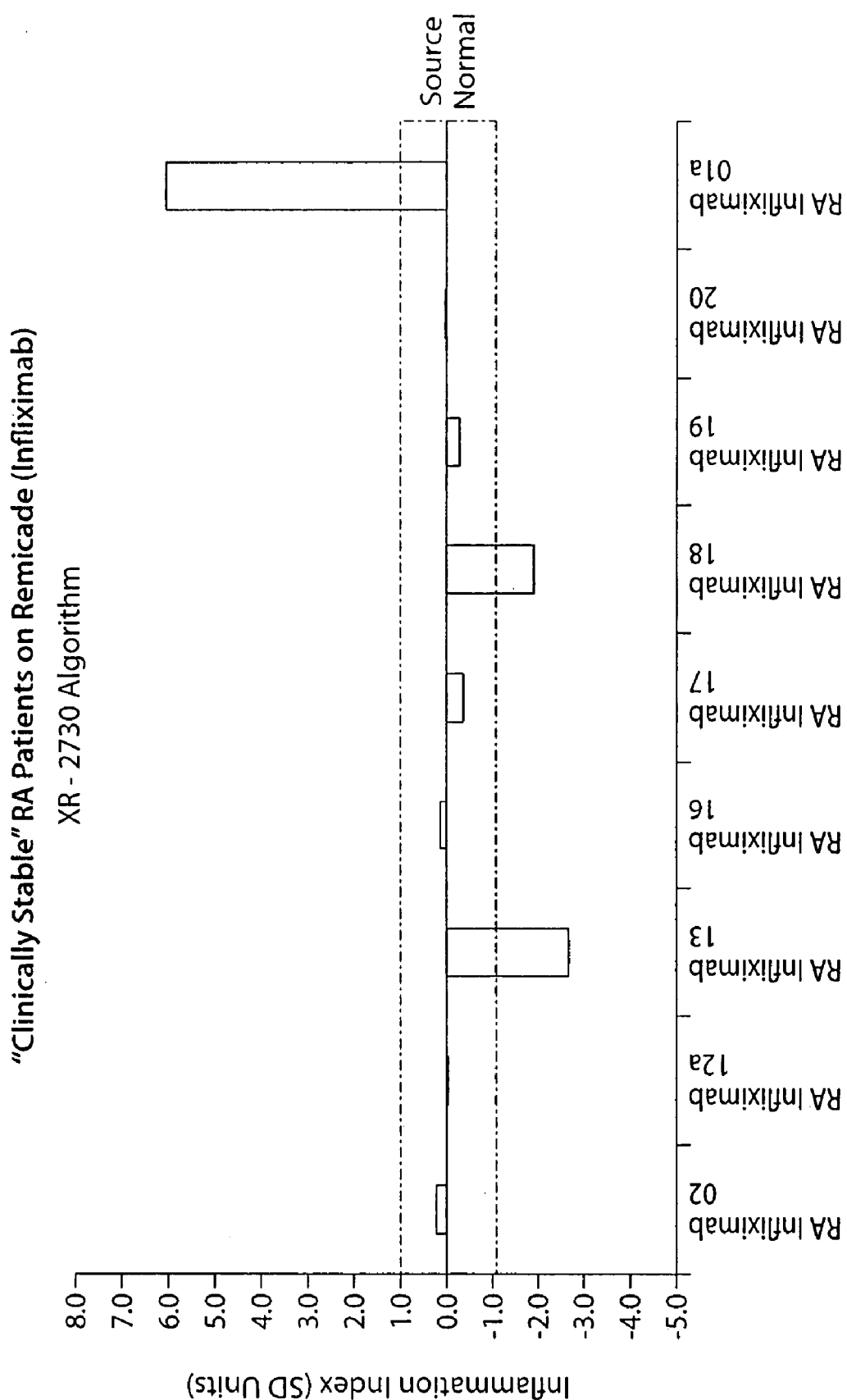
FIG. 21 illustrates inflammation index values for patients clinically stable on the TNF inhibitor Remicade, 4 weeks into the study.

FIG. 21 shows gene expression values for additional clinically stable RA patients being treated with Remicade (infliximab) for a panel of 10 genes known as the Inflammation Index (in standard deviation units).

Figure 22:
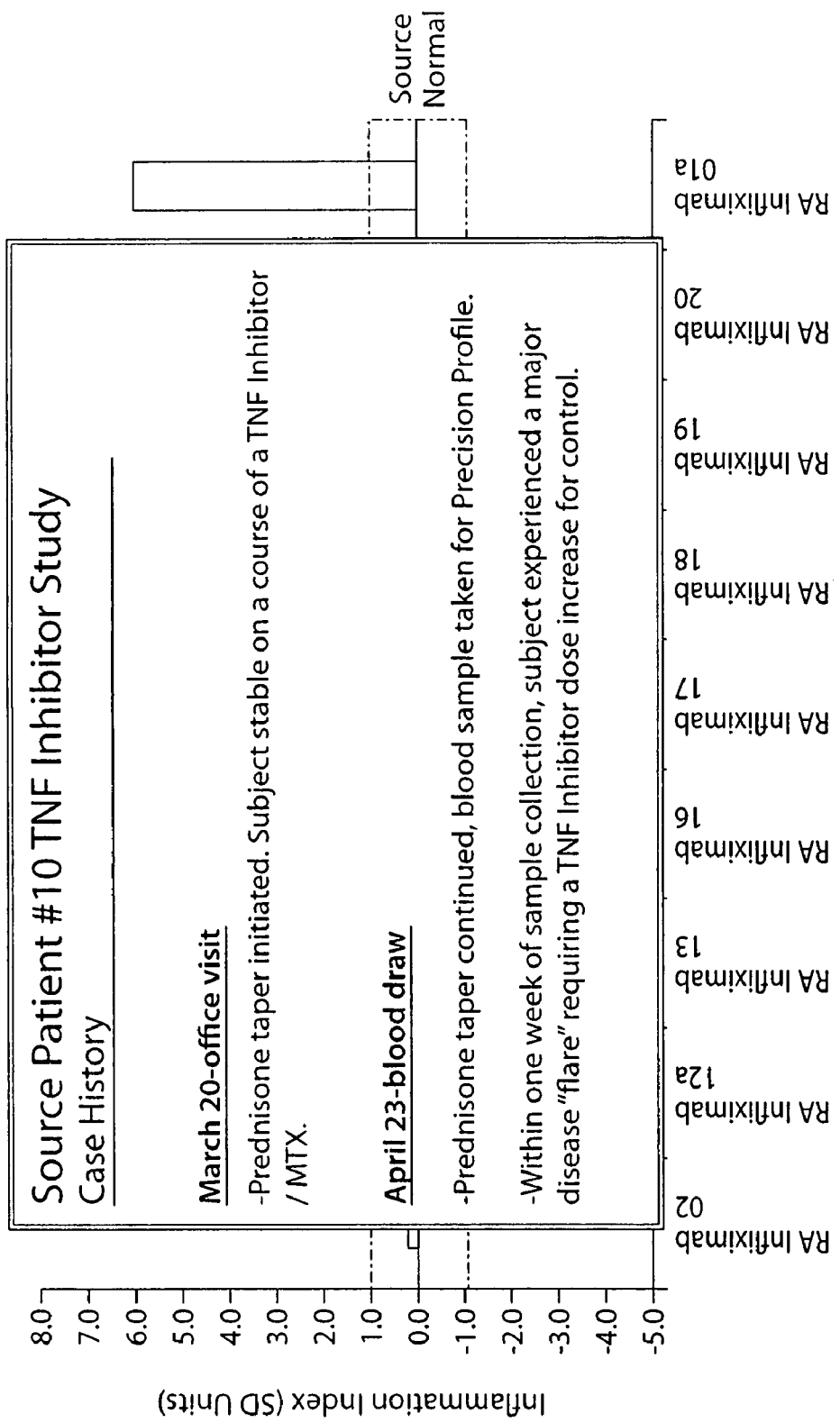
FIG. 22 illustrates aberrant patient 01a gene expression values in FIGS. 50 and 58, resulting from an active RA flare 1-week after sample collection for gene expression analysis.

FIG. 22 shows an assessment of the data presented in FIGS. 20 and 21, wherein a TNF inhibitor study performed on the patients (remicade/methotrexate program) resulted in a flare-up for patient 01a (see FIG. 21), requiring aggressive treatment involving increased TNF inhibitor dosage. These results for this patient were discussed previously, in FIG. 16, above.

Example 4

Correlating Clinical Assessment with High Precision Gene Expression Profiling

FIG. 23 shows the response of 22 patients over time in respect to 5 different clinical assessments traditionally used by clinicians for a study treating RA patients with kineret or sTNF-R1 plus kineret: Disease Activity Score (DAS); Swollen Joint Count (SJC); Tender Joint Count (TJ); MD Assessment of Disease (MDAD); and Health Assessment Questionaire (HAQ) self score, based on patient's evaluation on quality of life factors. As can be seen, the DAS decreased from the baseline of 6.51 to 5.35 after 4 weeks and down to 4.88 at the end of the study, and the joint counts, MD assessment and patient self-score also all went down over the course of the study and treatment period.

FIG. 24 shows Pearson Correlation Coefficients across all values for 5 clinical assessment methods traditionally used by physicians to monitor RA patients. As can be seen, the values for swollen joint count (SJC) and tender joint count (TJC) are not always statistically significant, but those for DAS tend to have statistical significance for most genes examined with this study. This study shows how it is possible to determine associations with clinical endpoints using simple correlations.

FIG. 25 shows that DAS is becoming the gold standard for comparison of the usefulness of the methodologies described and claimed herein using a gene expression panel selected to enable diagnosis, evaluation, and treatment of RA in patients. As can be seen, a mixed model analysis (i.e., multiple genes) indicates that the p-values for genes associated with determination of DAS values are statistically significant, indicating that the gene expression values determined for these genes in such a panel can be used in place of the traditional physician's DAS determination. The advantages are clear. A physician needs at least an hour, sometimes more, to determine a DAS value for a patient, and many of the indicators used to determine the DAS value are subjective. In contrast, using gene expression values for the panel of genes shown here, for example, allows an off-site, fast and totally objective assessment of a patient's RA status which, rivals, if not exceeds, the accuracy of the in-clinic assessment traditionally done by a physician.

FIG. 26 shows the relationship of gene expression to physician's assessment of disease using either a simple a correlation method of analysis (as in FIG. 23), or mixed model method of analysis for gene expression values (as in FIG. 24) determined for a number of genes of interest in unstable RA patients undergoing treatment with methotrexate.

Example 5

Clinical Data Analyzed with Latent Class Modeling (1-Gene, 2-Gene 3-Gene Models)

From a targeted 76-gene panel, selected to be informative relative to biological state of RA patients, primers and probes were prepared for a subset of 47 genes (those with p-values of 0.05 or better) (Table 3). Gene expression profiles were obtained using this subset of genes, and of these individual genes, TRL2 was found to be uniquely and exquisitely informative regarding RA, yielding the best discrimination from normals of the genes examined.

A ranking of the top 47 genes is shown in Table 3 summarizing the results of significance tests for the difference in the mean expression levels for Normals and RAs. Since competing methods are available that are justified under different assumptions, the p-values were computed in 2 different ways:
1) Based on 1-way ANOVA. This approach assumes that the gene expression is normally distributed with the same variance within each of the 2 populations.
2) Based on stepwise logistic regression (STEP analysis), where group membership (Normal vs. RA) is predicted as a function of the gene expression. Conceptually, this is the reverse of what is done in the ANOVA approach where the gene expression is predicted as a function of the group. The logistic distribution holds true under several different distributional assumptions, including those that are made in the 1-way ANOVA approach. Thus, this second strategy is justified under a more general class of distributional assumptions than the ANOVA approach.

As expected, the two different approaches yield comparable p-values and comparable rankings for the genes. Only 8 genes were found not to be significant at the 0.05 level. TLR2 was found to be the most significant. Table 3 shows that compared to the Normals, the washed-out RAs tend to be under-expressed with respect to TLR2.

Gene expression profiles were obtained using these subsets of genes using the Search procedure in GOLDMineR (Magidson, 1998) to implement stepwise logistic regressions (STEP analysis) for predicting the dichotomous variable that distinguishes RAs from Normals as a function of all 47 genes in an RA longitudinal study, i.e., a study that followed RA patients over an extended period of time after initiating Interleukin-1 receptor antagonist (IL1ra) or IL1ra plus soluble TNF-α receptor-1 therapy (IL1ra+sTNFR1) (N=22 'washed-out' RA subjects, and N=134 Normal subjects). The STEP analysis was performed under the assumption that the gene expressions follow a multinormal distribution, with different means and different variance-covariance matrices for the normal and RA population.

Actual correct classification rate for the RA patients and the normal subjects were computed. Multi-gene models were constructed which were capable of correctly classifying RA and normal subjects with at least 75% accuracy. These results are shown in Tables 4-10 below. As demonstrated in Tables 5-6 and Tables 8-10, as few as two genes allows discrimination between individuals with RA and normals at an accuracy of at least 75%.

One Gene Model

A STEP analysis was used first to find which were the most significant genes to use as the first gene in two gene models. All 47 genes were evaluated for significance (i.e., p-value) regarding their ability to discriminate between RA and Normals, and ranked in the order of significance (see, Table 4). The optimal cutoff on the ΔCt value for each gene was chosen that maximized the overall correct classification rate. The actual correct classification rate for the RA and Normal subjects was computed based on this cutoff and determined as to whether both reached the 75% criteria. None of these 1-gene models satisfied the 75%/75% criteria.

Two Gene Model

The top 6 genes (lowest p-value discriminating between RA and Normals, highlighted in Table 4) were subject to further analysis in a two-gene model. Each of the top 6 genes, one at a time, was used as the first gene in a 2-gene model, where all 46 remaining genes were evaluated as the second gene in this 2-gene model. All models that yielded significant incremental p-values, at the 0.05 level, for the second gene were then analyzed using Latent Gold to find $R^2$ values. The $R^2$ statistic is a less formal statistical measure of goodness of prediction, which varies between 0 (predicted probability of being in RA is constant regardless of delta-ct values on the 2 genes) to 1 (predicted probability of being RA=1 for each RA subject, and =0 for each Normal subject). If the 2-gene model yielded an $R^2$ value greater than 0.6 it was kept as a model that discriminated well. If these models met the 0.6 cutoff, their statistical output from Latent Gold, was then used to determine classification percentages (shown in Table 5).

Three Gene Model

The 2-gene models that discriminated well were subject to more STEP analyses as the first two genes for 3-gene models where all 45 remaining genes were evaluated as the third gene in this 3-gene model. Again, Latent Gold was used to determine $R^2$ values as well as p-values for each gene. All models that yielded significant incremental p-values, at the 0.05 level, for the third gene were then analyzed using Latent Gold to find $R^2$ values. For all 3-gene models that yielded an $R^2$ value greater than 0.6, classification percentages were determined using their statistical output from Latent Gold (shown in Table 6)

Without taking into account group membership (normals vs. RA) in the estimation of the model parameters, the 3-gene model perfectly distinguished the 2 groups. The most significant of these genes was TLR2. Given TLR2, a second gene, CD4, made the most significant incremental contribution towards the discrimination between the normals and RAs, and including a $3^{rd}$ gene, NFKB1, in the model led to perfect discrimination. Other 3-gene models are described in Table 6. Overall, the expression levels of at least 38 genes were found to differ significantly (p<0.05) between 134 normals and 22 'washed-out' RAs among the 47 genes for which measurements were obtained.

Figure 27:
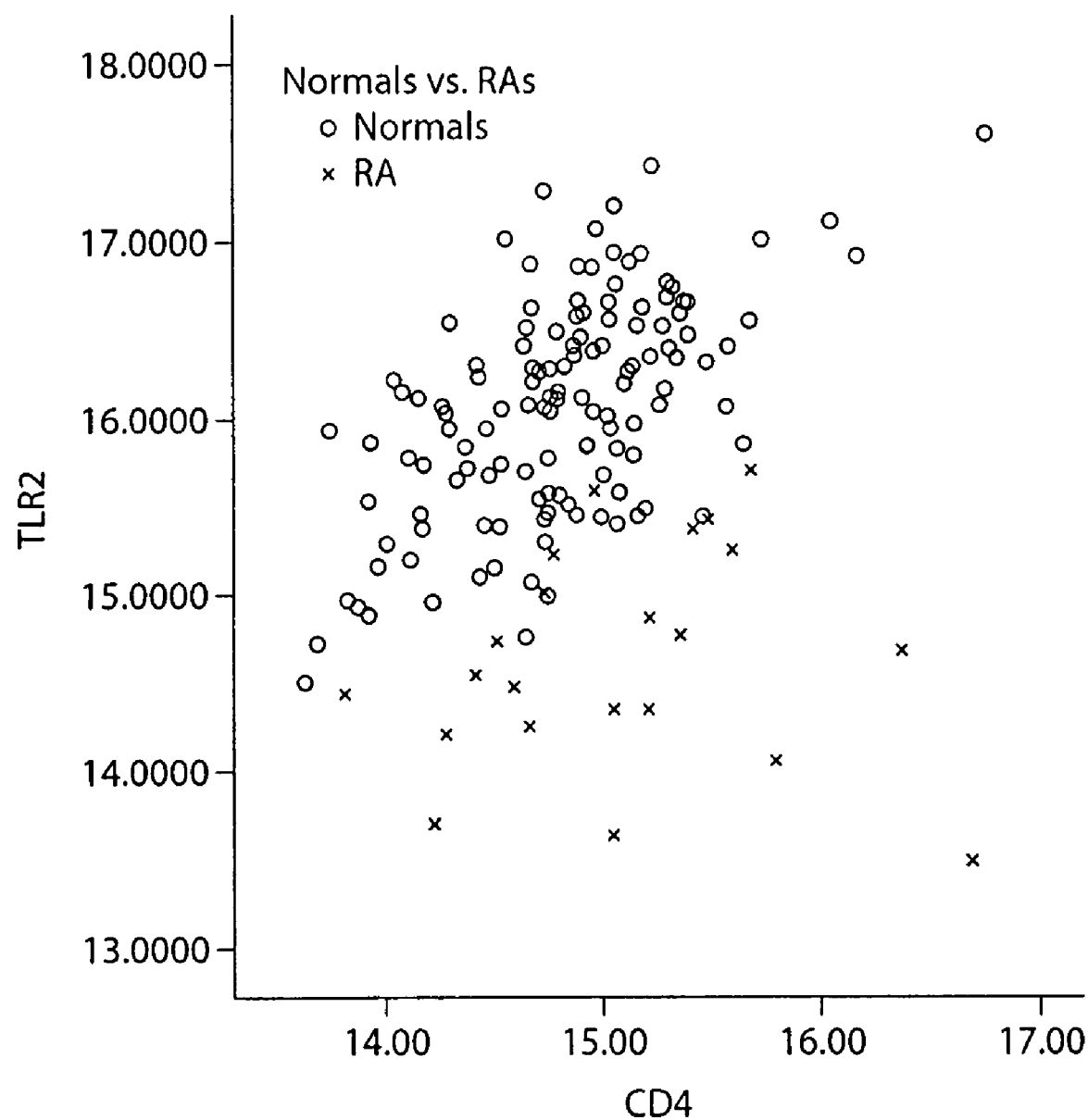
FIG. 27 illustrates a scatterplot of CD4 by TLR2 for 132 Normals and 22 RAs.

FIG. 27 shows the strong discrimination provided by TLR2 and CD4. For normals, the mean expression levels are (TLR2, CD4)=(16.1, 14.8); for RAs, (TLR2, CD4)=(14.8, 15.1). Within Normals, TLR2 and CD4 have a significant positive correlation (r=0.577), but within RAs, the correlation is not significantly different from 0 (r=0.061).

Figure 28:
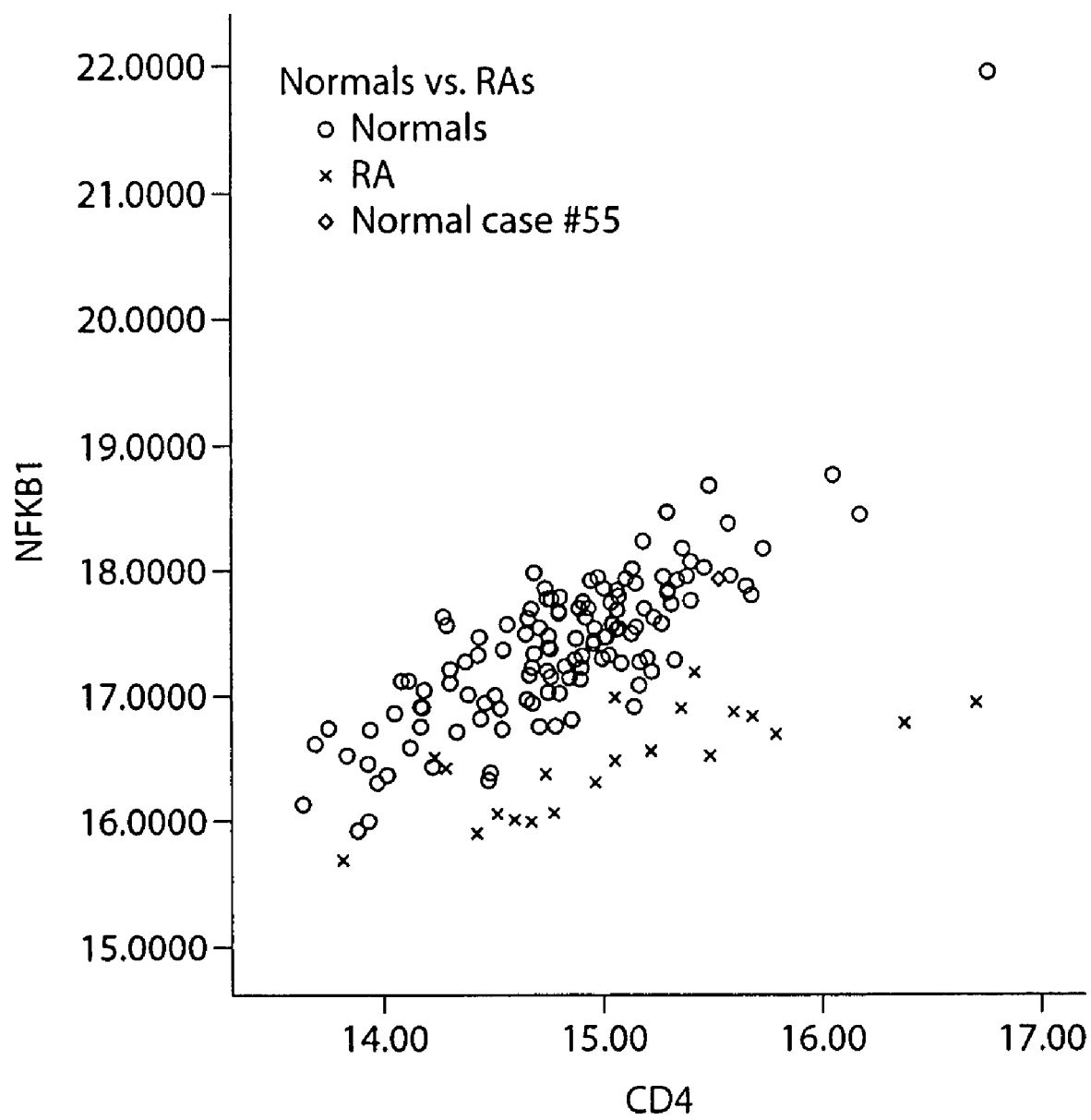
FIG. 28 illustrates a scatterplot of CD4 by NFKB1 for 133 Normals and 22 RAs (Plot separately identifies Normal #55, which is missing on TLR2).

Given these 2 genes, adding a $3^{rd}$ (NFKB1) provided perfect prediction. Like TLR2, RAs are under-expressed on NFKB 1, and the relationship between NFKB1 and CD4 (see FIG. 28) is similar to the relationship between TLR2 and CD4 shown in FIG. 27. (However, unlike the relationship shown in FIG. 27 for TLR2 and CD4, the correlation between NFKB1 and CD4 is large for both Normals (r=0.799) and RAs (r=0.738).)

Again, with these 3 genes included in the model, prediction was perfect. In fact, the predicted probability of being an RA was 1 for each RA in the sample and 0 for each Normal case (to 8 decimal places). (The predicted probability incorporates the prior probability of being an RA, which is reflected in the intercept of the logit model. Since this analysis consists of 22 RAs out of a total sample of 154, the prior probability was set at 22/154. Alternative priors can be used which change the intercept—a change in the prior does not affect the other estimated coefficients. For example, to use a prior probability of 0.5 of being an RA, the current prior odds of 22/132 would be multiplied by 132/22, which is equivalent to adding log (132/22)=1.179 to the intercept. To use a prior odds of 1:1000, the current prior odds of 22/132 would need to be multiplied by (132/22)×(1/1000)=0.006, and thus log(0.006)=−5.116 would be added (5.116 subtracted) from the intercept. In both of these cases, prediction still would be perfect—that is, the predicted Prob(RA) is close to 1 for RAs and close to 0 for Normals. The predicted probabilities are not affected much by changes in the prior probability. For example, if the prior RA: Normal odds is taken anywhere in the range between 1:100,000 and 100,000:1, the predicted probability of being an RA would still be 1.00 for each true RA and 0.00 for each true normal (to at least 2 decimal places).)

The following model was used:

$$Logit(RA)=1020.9+165.3*CD4-115.8*NFKB1-101.3*TLR2$$

where 'Logit' is the logarithm of the odds of being an RA as opposed to a Normal. Thus, $$Prob(RA)=exp[Logit(RA)]/[1+exp[Logit(RA)]],$$

where Prob(RA) is the probability of being an RA under the assumption that there are only 2 populations—Normals and RAs.

Higher values for CD4 and lower values for NFKB1 and TLR2 increase the odds (probability) of RA. While these are maximum likelihood estimates, because of the perfect aspect of the model, no standard errors are available for the model parameters. To see whether the model could be simplified changing the perfect prediction of the model, coefficients for NFKB1 and TLR2 were equated, and the model re-estimated. (Equating the coefficients for TLR2 and NFKB1 was accomplished by creating a new variable (called tPn) equal to the sum of TLR2 and NFKB1, and using this together with CD4 in the logit model.) The prediction continued to be perfect, as shown by the separation line added to FIG. 29. The more parsimonious the model (fewer parameters), the more likely the model is to validate on other data. Thus, the fewer the genes used, the fewer the number of model parameters. Here, there are only 3 genes, and the number of parameters were further reduced by equating the effects of 2 of the genes.

Figure 29:
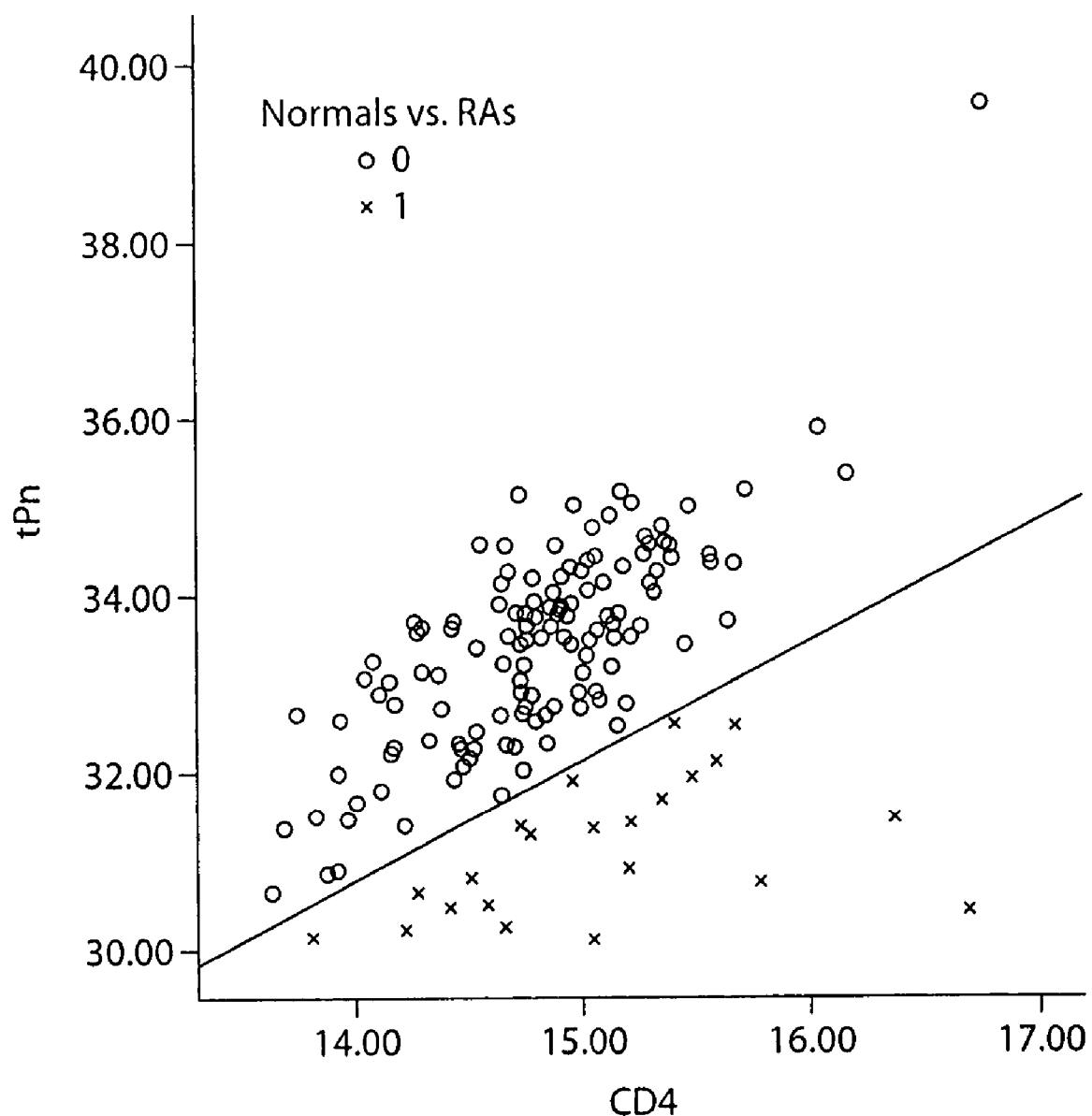
FIG. 29 illustrates a scatterplot of CD4 by tPN (=TLR2+ NFKB 1) for 132 Normals and 22 RAs. Appended line shows that RAs are perfectly distinguished from Normals on the basis of CD4 and tPN.
Figure 30:
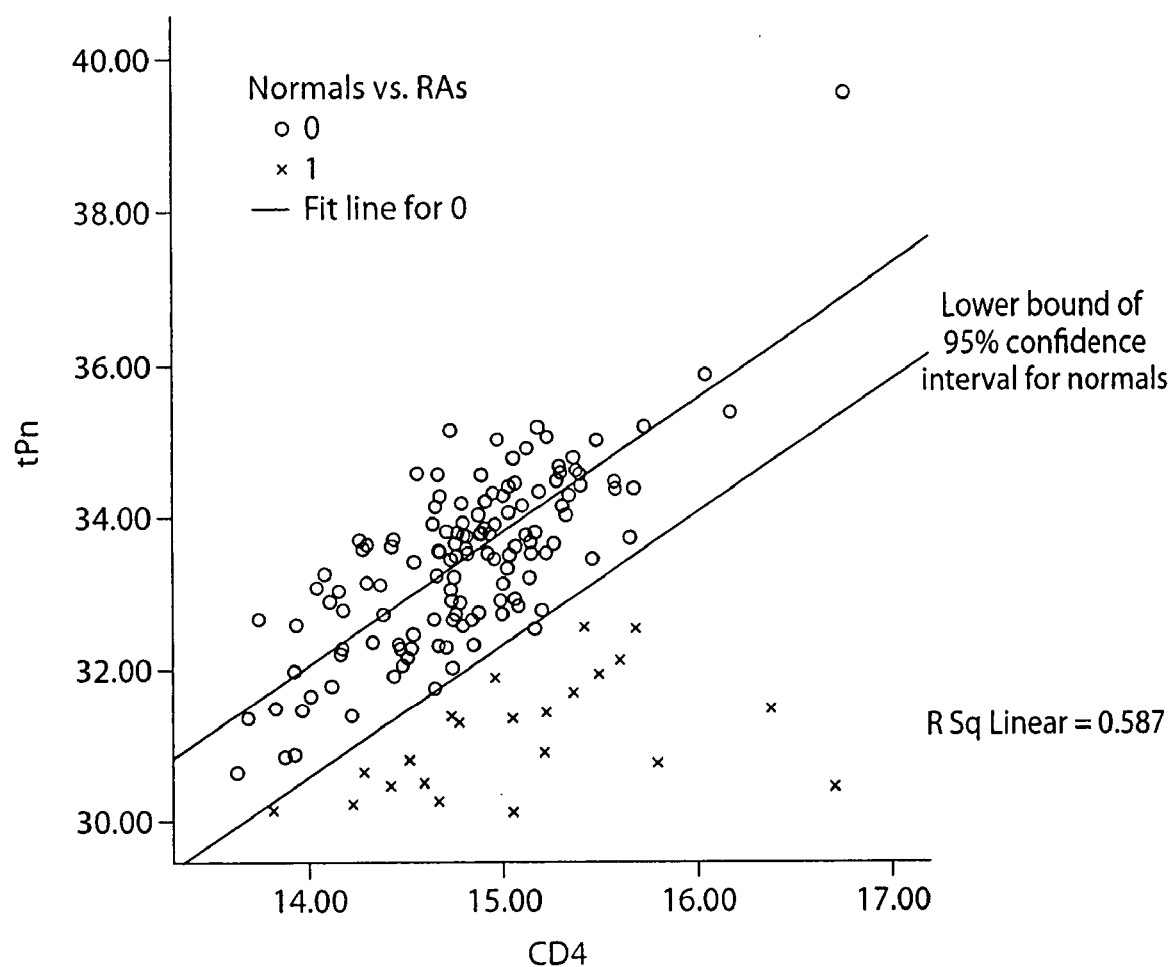
FIG. 30 illustrates the best least squares fitting line and lower 95% predicted confidence limit to the Normals data showing the expected value for tPN given a particular expression level for CD4.
Figure 31:
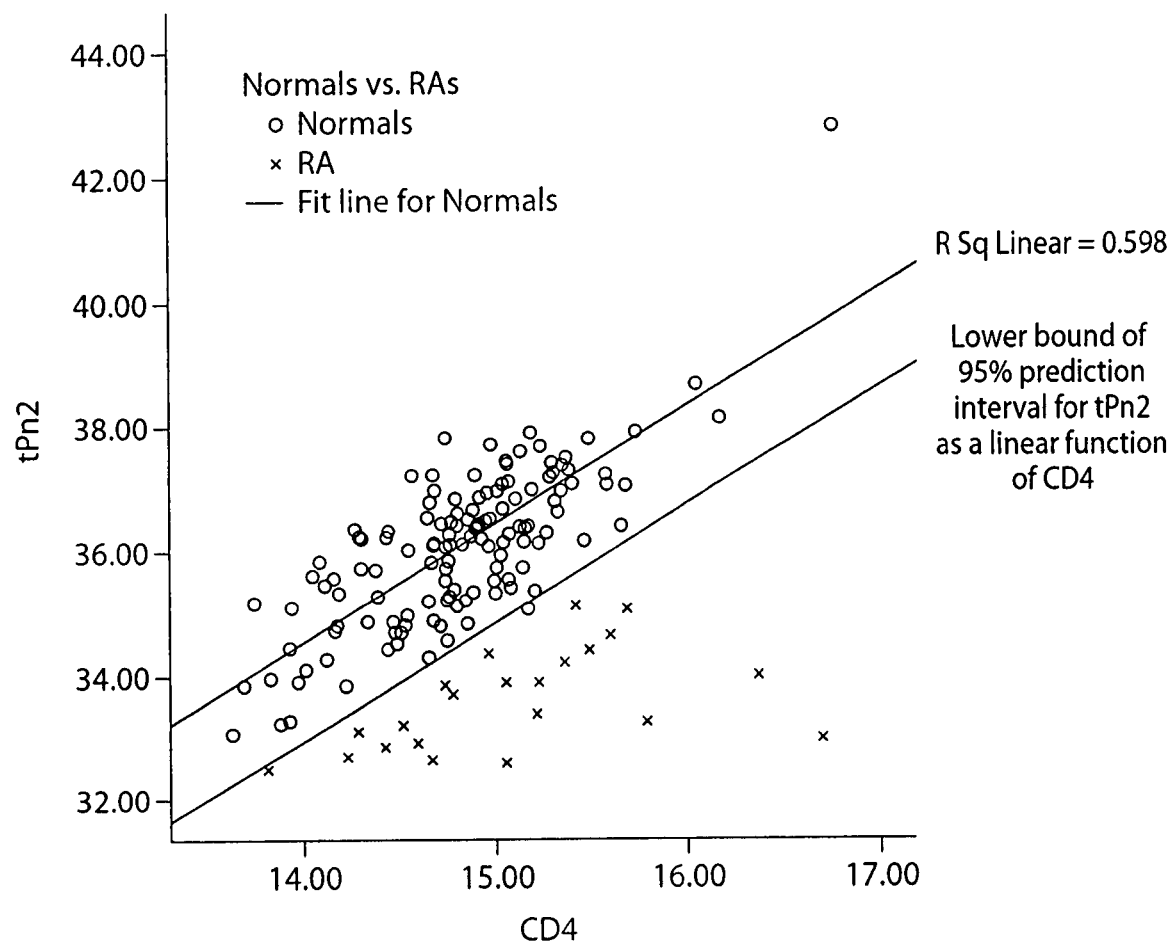
FIG. 31 illustrates the best least squares fitting line and lower 95% predicted confidence limit to the Normals data showing the expected value for tPN2 given a particular expression level for CD4.

FIG. 29 plots tPn by CD4 and shows that a line can perfectly distinguish the two groups. All cases above the line are Normal cases, all below are RAs. This separation line is not unique. (This line is not unique as there are an infinite number of lines that can provide perfect discrimination. Note that because the discrimination is perfect, without additional data containing some amount of imperfect discrimination it is not possible to determine whether the sum of TLR2 and NFKB1 is optimal or some other weighting such as tPn2=1.15*NFKB1+TLR2. That is, there are an infinite number of possible weightings of these 2 genes that provide perfect discrimination.) However, it is possible to obtain a unique equation, and estimated probabilities of being an RA (strictly between 0 and 1) by making some distributional assumptions. We take this approach in the section below on estimating a latent class model. Alternatively, a conditional model can be estimated, for example, by focusing on the prediction of tPn as a function of CD4. FIGS. 30 and 31 show the best least squares fitting line and lower 95% predicted confidence limit for the Normals data showing the expected value for tPn and tPn2 given a particular expression level for CD4. The RA population falls below the lower limit.

Example 6

Clinical Data Analyzed with Latent Class Modeling (1-Gene, 2-Gene, 3-Gene and 4-Gene Models)

From a targeted 76-gene panel, selected to be informative relative to biological state of RA patients, primers and probes were prepared for a subset of 24 genes (those with p-values of 0.05 or better). Gene expression profiles were obtained using this subset of genes, and of these individual genes, ICAM was found to be uniquely and exquisitely informative regarding RA, yielding the best discrimination from normals of the genes examined.

The Search procedure in GOLDMineR (Magidson, 1998) was used to implement a stepwise logistic regressions (STEP analysis) were used for predicting the dichotomous variable that distinguishes RAs from Normals as a function of all 47 genes in a study an RA longitudinal study, i.e., a study that followed RA patients over an extended period of time after initiating NSAIDS, methotrexate, or new TNF-inhibitor therapy (N=20 'washed-out' RA subjects and N=32 Normal). A STEP analysis was used to obtain predictions under 1-gene, 2-gene, 3-gene, and 4-gene models. As described infra, 4-gene models provided perfect discrimination between RA and Normal populations.

One Gene Model

A STEP analysis was used first to find which were the most significant genes to use as the first gene in two gene models. All 24 genes were evaluated for significance (i.e., p-value) regarding their ability to discriminate between RA and Normals, and ranked in the order of significance (see, Table 7). The optimal cutoff on the ACt value for each gene was chosen that maximized the overall correct classification rate. The actual correct classification rate for the RA and Normal subjects was computed based on this cutoff and determined as to whether both reached the 75% criteria. None of these 1-gene models satisfied the 75%/75% criteria.

Two Gene Model

The top 6 genes (lowest p-value discriminating between RA and Normals, (highlighted in Table 7) were subject to further analysis in a two-gene model. Each of the top 6 genes, one at a time, was used as the first gene in a 2-gene model, where all 23 remaining genes were evaluated as the second gene in this 2-gene model. All models that yielded significant incremental p-values, at the 0.05 level, for the second gene were then analyzed using Latent Gold to find $R^2$ values for each gene. The $R^2$ statistic is a less formal statistical measure of goodness of prediction, which varies between 0 (predicted probability of being in RA is constant regardless of delta-ct values on the 2 genes) to 1 (predicted probability of being RA=1 for each RA subject, and =0 for each Normal subject). If the 2-gene model yielded an $R^2$ value greater than 0.6 it was kept as a model that discriminated well. If these models met the 0.6 cutoff, Latent Gold or GoldMineR was then used to determine classification percentages (shown in Table 8).

Three Gene Model

The 2-gene models that discriminated well were subject to more STEP analyses as the first two genes for 3-gene models where all 22 remaining genes were evaluated as the third gene in the 3-gene model. Again, Latent Gold was used to determine $R^2$ values as well as p-values for each gene. All models that yielded significant incremental p-values, at the 0.05 level, for the third gene were then analyzed using Latent Gold to find $R^2$ values. For all 3-gene models that yielded an $R^2$ value greater than 0.6, classification percentages were determined using Latent Gold or GoldMineR (shown in Table 9).

Four Gene Model

The 3-gene models that discriminated well were subject to yet more STEP analysis as the first 3 genes for 4-gene models where all 21 remaining genes were evaluated as the $4^{th}$ gene in the 4-gene model. Again, Latent Gold was used to determine $R^2$ values as well as p-values for each gene. All models that yielded significant incremental p-values, at the 0.05 level for the fourth gene were then analyzed using Latent Gold to find $R^2$ values. For all 3-gene models that yielded an $R^2$ value greater than 0.6, classification percentages were determined using Latent Gold or GoldMineR (shown in Table 10)

Again, without taking into account group membership (normals vs. RA) in the estimation of the model parameters, 4-gene modeling perfectly distinguished the 2 groups. In one model, the most significant of these genes was ICAM. Given ICAM, a second gene, HLADRA, made the most significant incremental contribution towards the discrimination between the normals and RAs. Including a $3^{rd}$ gene, HSPA1A, in the model made the next most significant incremental contribution towards discrimination, and including a $4^{th}$ gene, TGFB1 provided perfect discrimination. In the other model, the following 4-gene model provided perfect discrimination between normals and RA populations: CSPG2, HLADRA, CD14, and ITGAL. Other 4-gene models are described in Table 10.

Example 7

Clinical Data Analyzed with Latent Class Modeling: Normal V. Unstable RA

Figure 32:
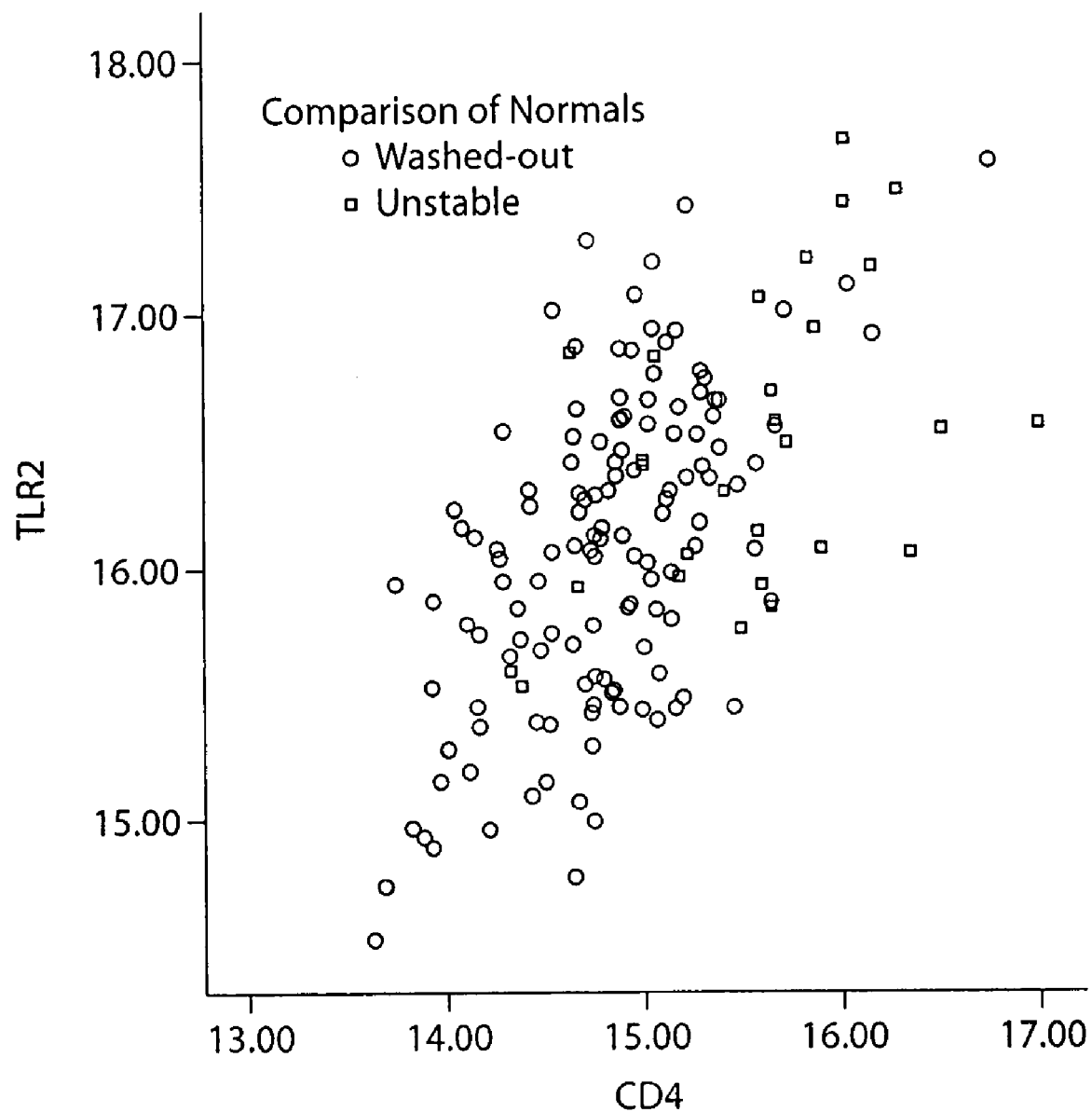
FIG. 32 illustrates comparison of Normals from 2 studies on expression levels for CD4 and TLR2.

To test whether the results described above could be generalized beyond the 'washed-out' RAs, Normals and RAs from an 'unstable RA' study were examined. NFKB1 was not measured for these subjects. Data from a different study containing 27 normals and 10 unstable RAs for which measurements on both TLR2 and CD4 were available (NFKB1 expressions were not measured in this study) were used to validate the results from the 2-gene model. However, the 27 Normals and 10 'unstable RAs' contained non-missing values on CD4 and TLR2. Compared to the 134 Normals from the 'washed-out' RA study, these Normals were similar with respect to the estimated variances and correlation (r=0.59) for these gene expressions, but have significantly higher mean expression levels for both CD4 and TLR2: means=(15.6, 16.5) vs. (14.8, 16.1). See FIG. 32.

Figure 33:
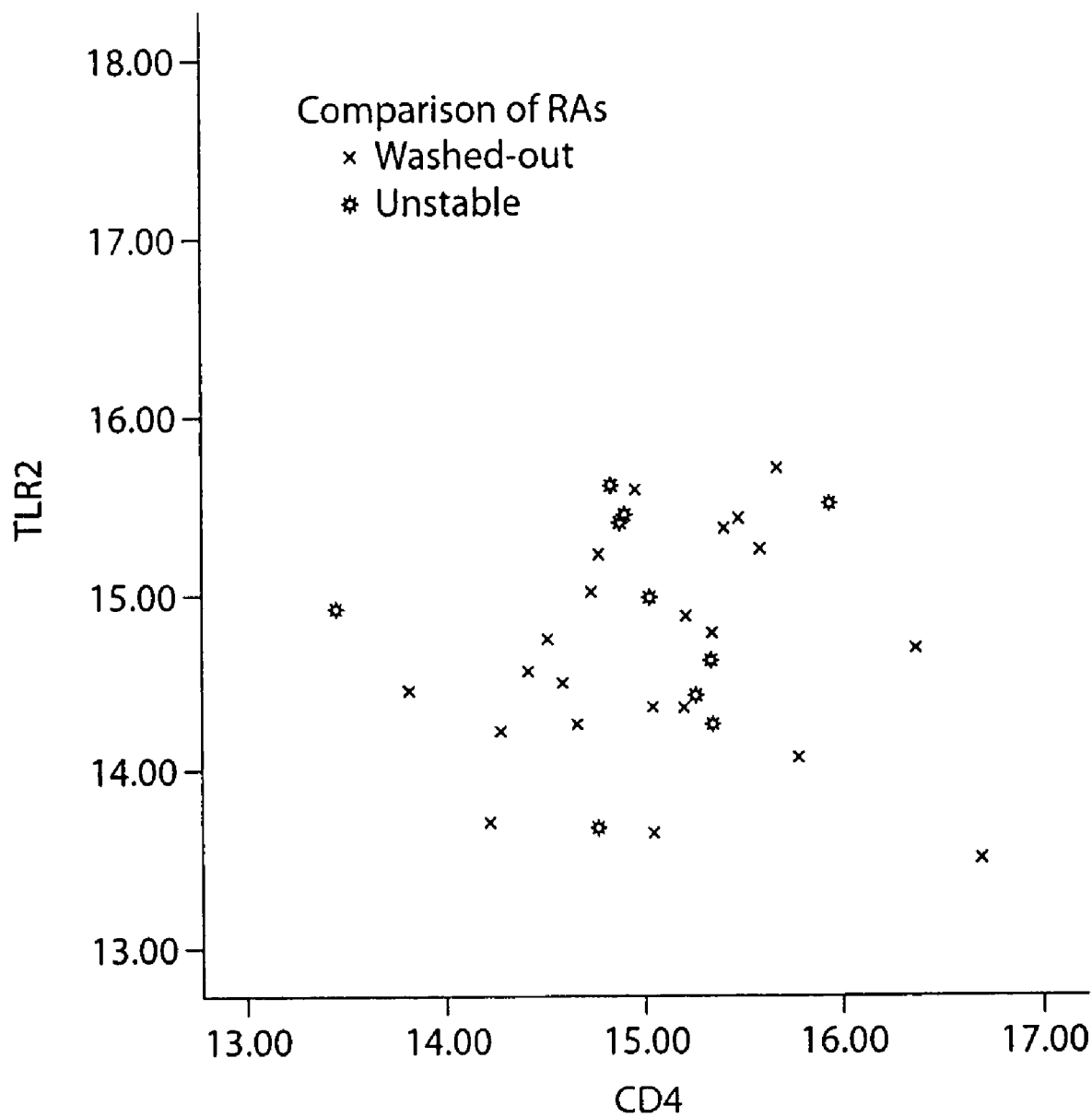
FIG. 33 illustrates comparison of RAs from 2 studies with respect to expression levels on CD4 and TRL2.

'Unstable' RAs with non-missing values on CD4 and TLR2 (N=10 depicted as stars in FIG. 33) are indistinguishable from 'Washed-out' RAs (N=22 depicted as Xs in FIG. 33) with respect to mean expression levels and variances for CD4 and TLR2. In addition, both show zero correlation between CD4 and TLR2, unlike the significant positive correlation for Normals. See FIG. 33.

Figure 34:
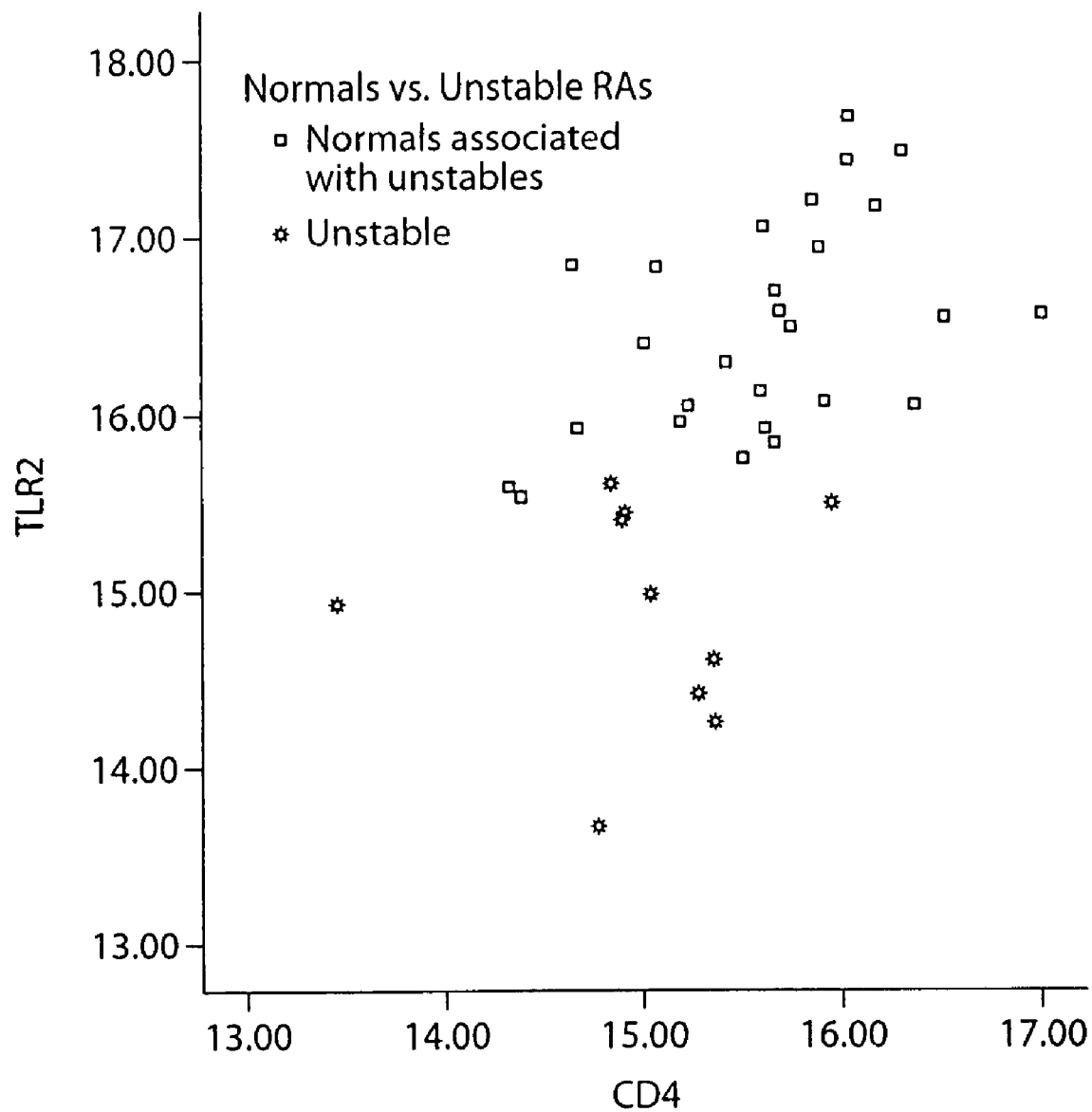
FIG. 34 illustrates comparison of Normals vs. Unstable RAs with respect to CD4 and TLR2 expression levels.
Figure 35:
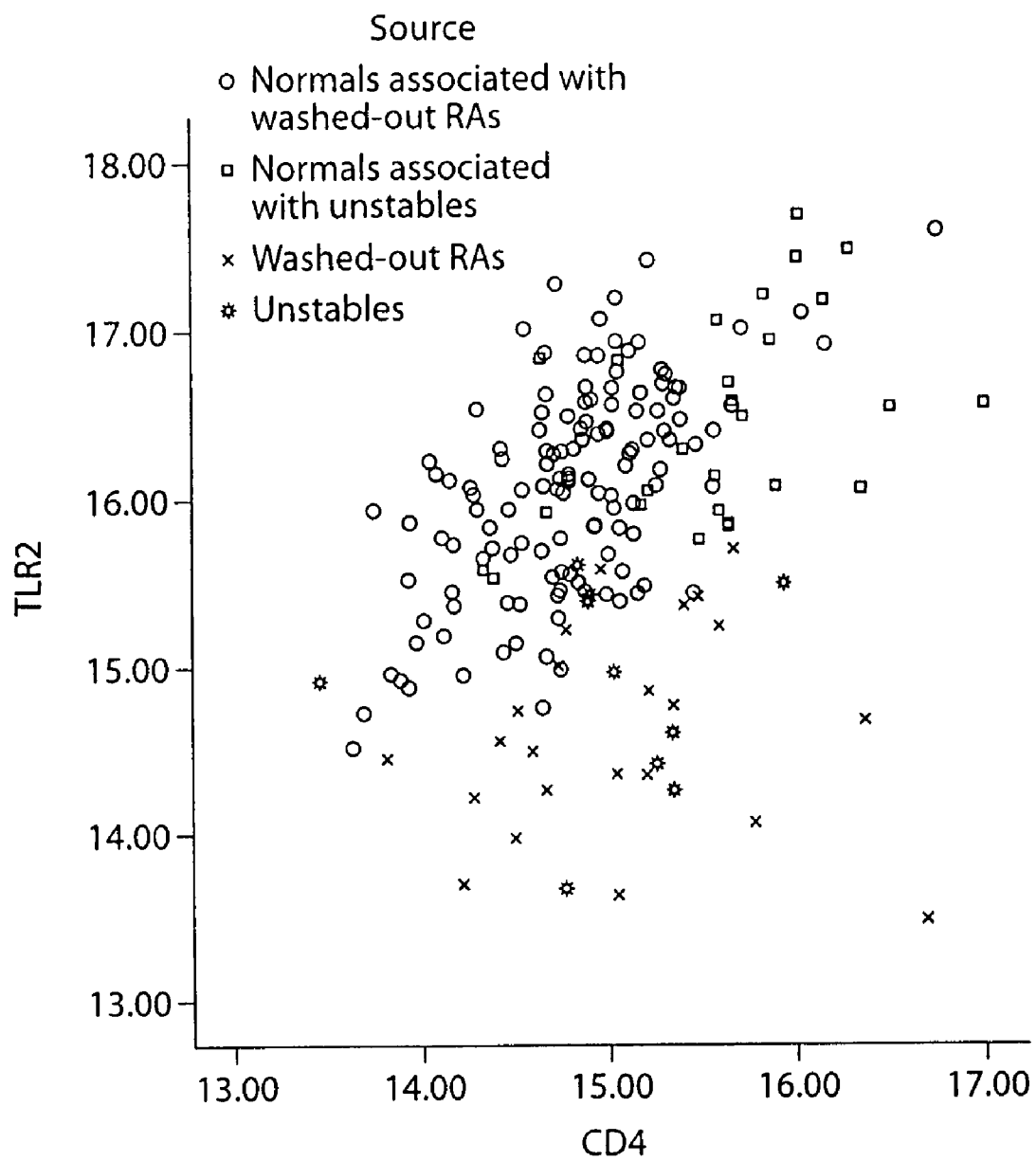
FIG. 35 illustrates data for both washed-out and unstable RA studies together.

FIG. 34 shows that Unstable RAs have significant lower levels than Normals on both genes. FIG. 35 shows the data for both studies together. The results here suggest that the model can probably be generalized to apply also to unstable RAs.

Example 8

Estimating a Latent Class Model

Assuming that the gene expressions follow a multinormal (MVN) distribution within the Normal population, and that MVN also characterizes the distribution within the RA population (with different means and possibly different variances and correlations), it is possible to develop a model that discriminates between the 2 groups without using information about group membership.

Latent class (LC)/finite mixture modeling was used to examine the number of latent classes in the data under the above assumptions, and determine how closely related these classes are to the Normals and RAs. The possibility of selection effects was minimized in the development of the model by not using the information about group membership in the model estimation, and see to the extent to which the model could predict group membership. Baseline gene expressions for RAs and for normals on tPn and CD4 were determined, without identifying group membership to develop a model that estimates the probability of being in the RA group (vs. normal) under the above distributional assumptions. This methodology is similar to that employed by Vermunt and Magidson (2004) where a LC model was developed that accurately classified individuals into the appropriate group (normal, overt diabetes, chemical diabetes) on the basis of 3 clinical measures (glucose, insulin, SSPG).

Figure 36:
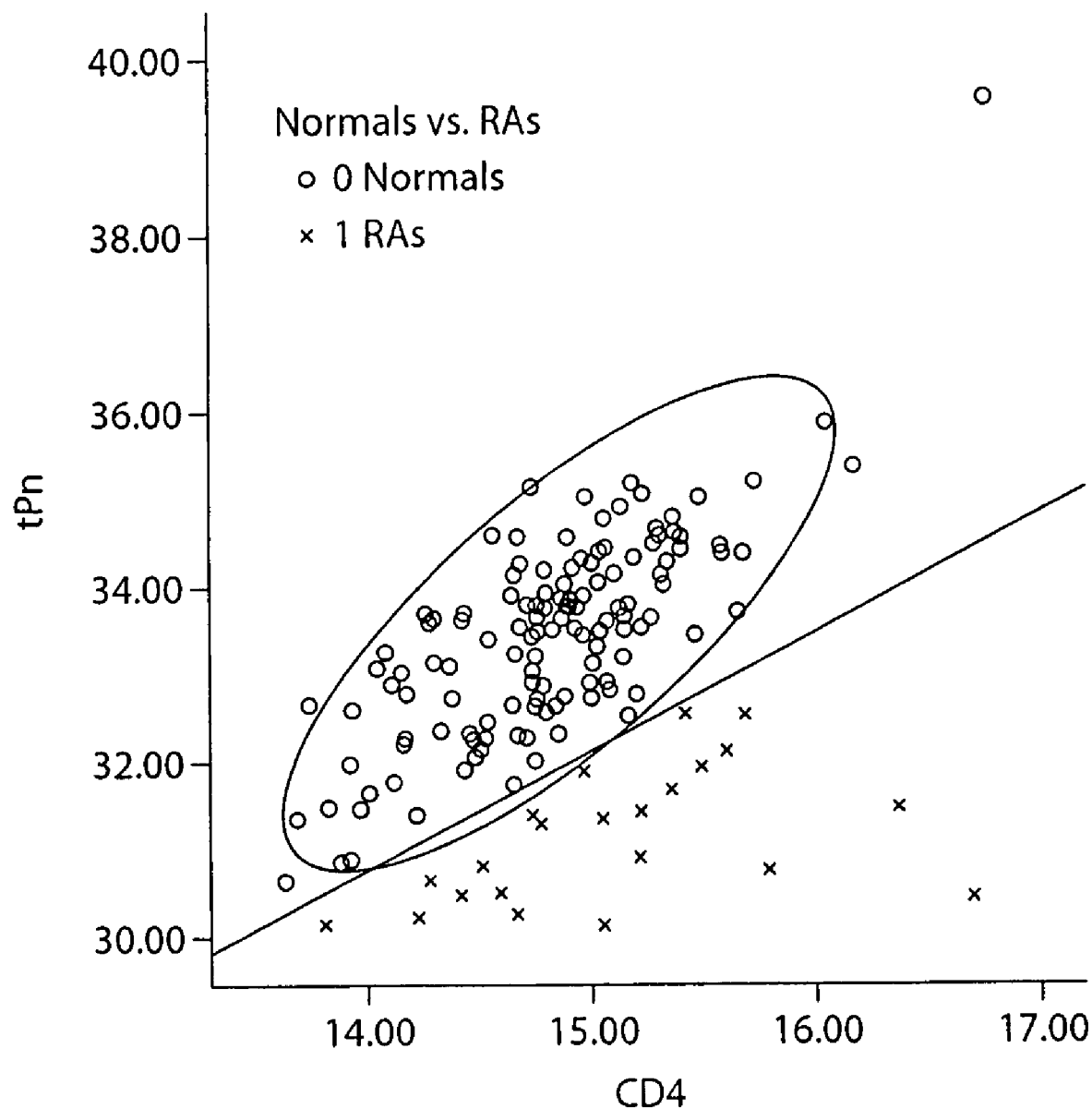
FIG. 36 illustrates the approximate 95% ellipsoid for normals data.
Figure 37:
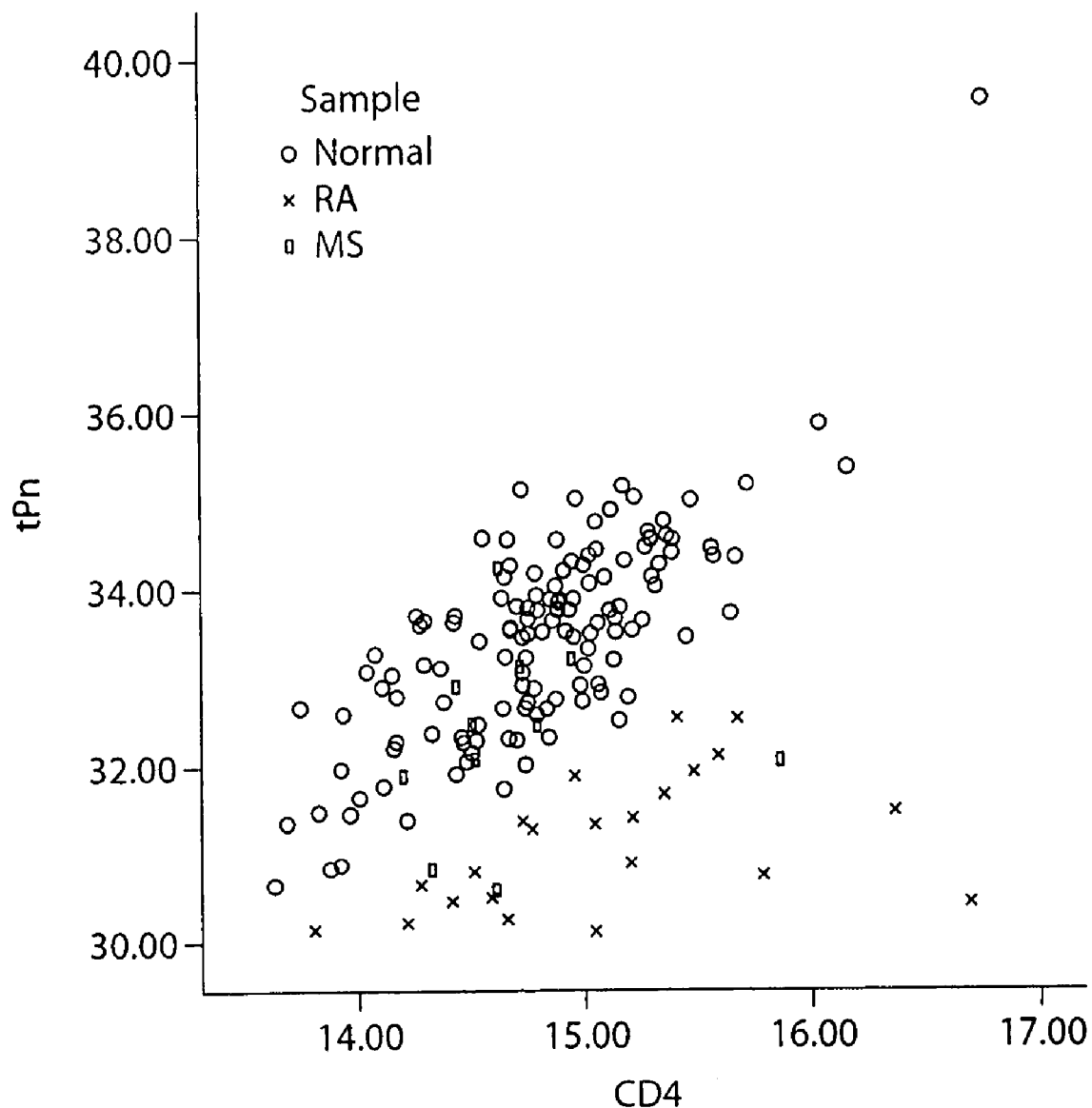
FIG. 37 illustrates the relationship between tPn and CD4 for all cases in the washed out study plus 11 MS subjects, showing that separation is apparent between 3 MS subjects who look like RA subjects and the other 8 MS subjects who look more like Normals.
Figure 38:
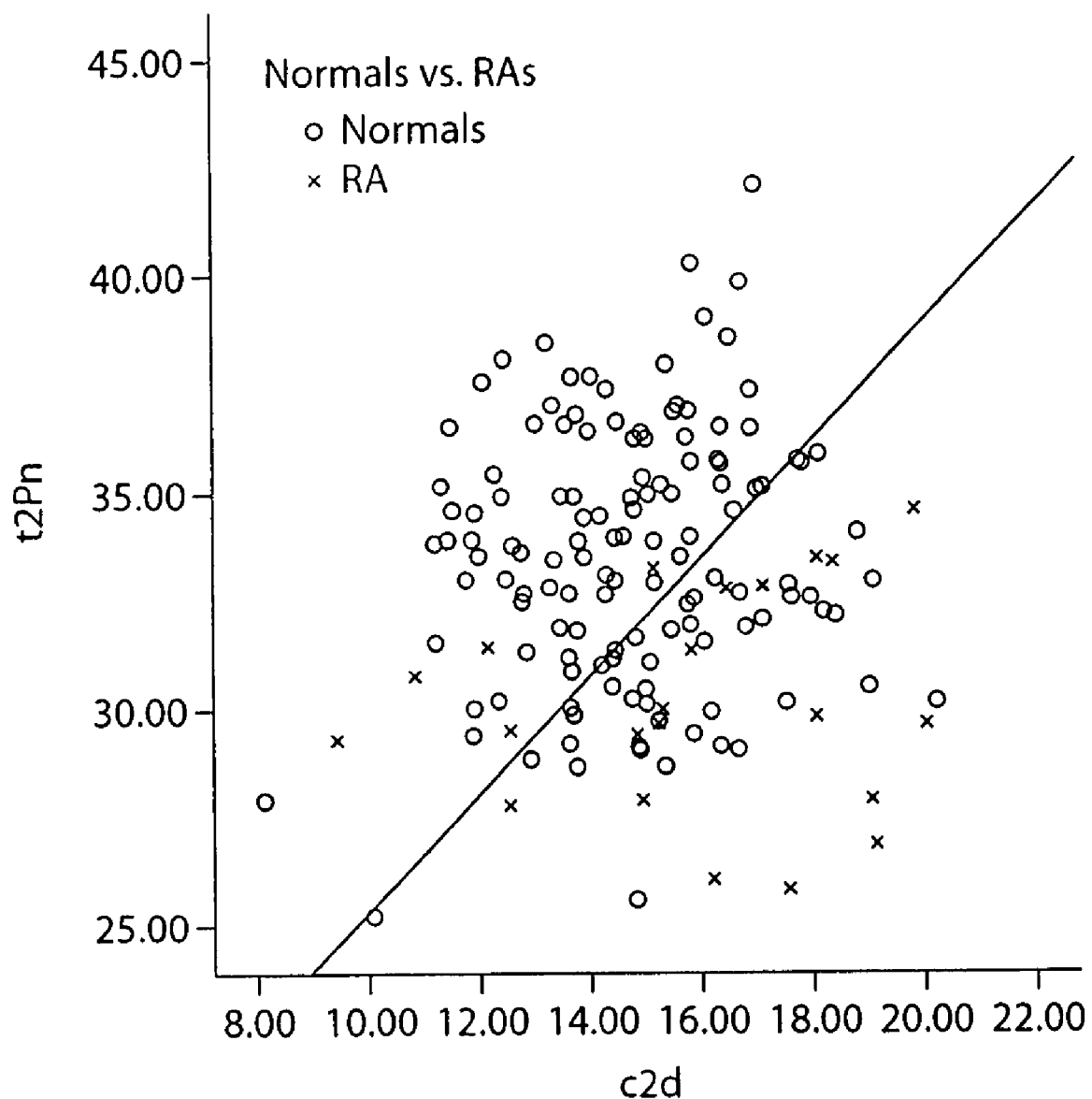
FIG. 38 illustrates original data with very large amount of error added (s=2).
Figure 39:
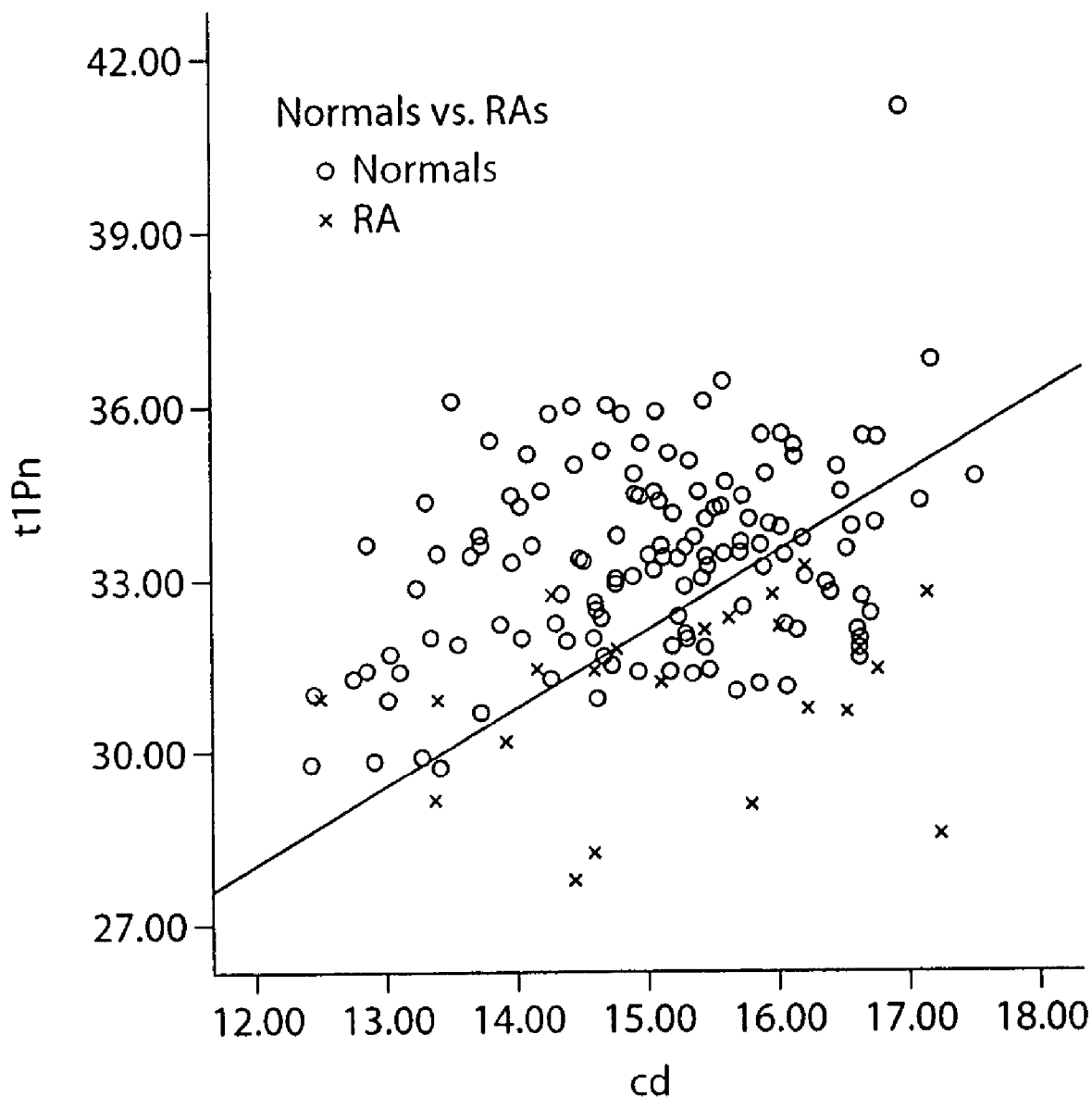
FIG. 39 illustrates original data with large amount of error added (s=1).
Figure 40:
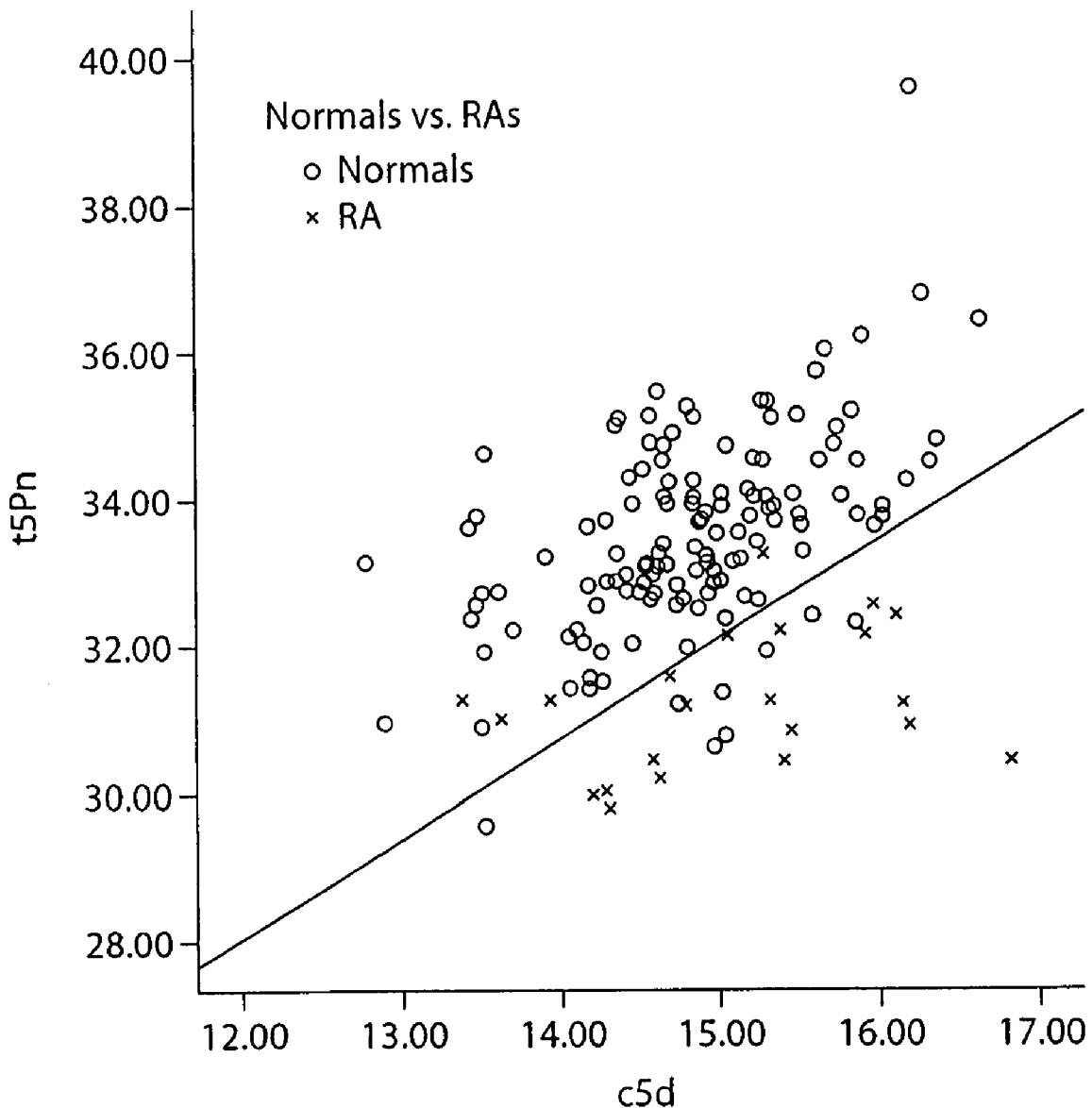
FIG. 40 illustrates original data with moderate amount of error added (s=0.5).
Figure 41:
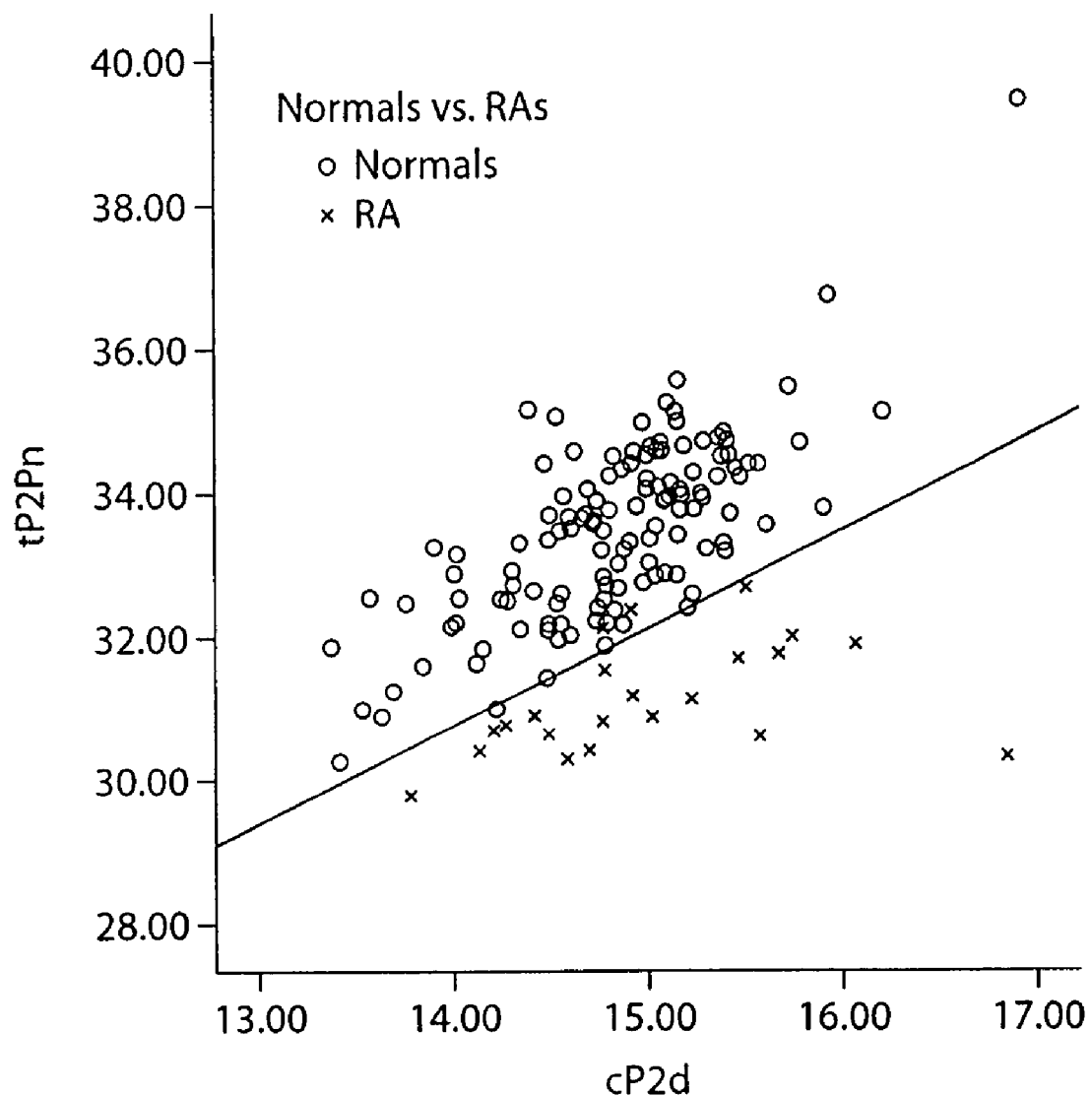
FIG. 41 illustrates original data with small amount of error added (s=0.2).

Given values for tPn and CD4, the Bayesian Information Criteria (BIC) correctly identified 2 classes in the data (the 2-class model had the smallest BIC among models estimated containing between 1 and 4 classes). The first class consisted of all the Normals and the second consisted of all the RAs. The estimated parameters from this model (means, variances and correlations within each group) can be used to construct a 95% Confidence Region for the normals (FIG. 36). More specifically, it was assumed that within the Normals population, the variables tPn2 and CD4 follows a bivariate normal distribution with means (tPn, CD4)=(33.5, 14.8), variances (1.33, 0.245) and correlation r=0.74. As can be seen in FIGS. 37 and 38, all of the RAs fall outside this region. As expected, some of the Normals also fall outside the 95% confidence region (approximately 5% would be expected to fall outside this region by chance). However, none of these falls below the discrimination line.

Next, MS subjects (n=11) were included among the sample subjects the LC analysis was repeated. The results again indicated that there were 2 classes (see Table 11) (BIC is lowest for the 2-class model). Class I again corresponded to the Normals, as shown in Table 12, all of the normals were classified into this class. The parameter estimates were very similar to those obtained without the MS subjects included, i.e., the model described supra. As before, all of the RAs were classified into class 2. The posterior probabilities are given in Tables 12, 13, and 14. Regarding the 11 MS subjects, 8 are assigned to the Normal class (for each of these, the posterior probability is estimated to be at 0.89 or higher of being in this class), the other 3 are classified into class 2 with the RA subjects. FIG. 37 shows the separation between 3 MS subjects who look like RA subjects and the other 8 MS subjects who look more like Normals.

Assuming that these 3 MS subjects do not in fact have RA, this data suggests that one or more additional genes could be included in the model, to distinguish the RAs from those MS subjects who might have similar gene expressions on CD4 and tPn.

In the present RA model, the following inferences appear justified (at least for a large subset of the genes):
1) The gene expressions within the normal population follows a multivariate normal (MVN) distribution.
2) The gene expressions within one or more non-normal populations follows a multivariate normal distribution with perhaps different means, variances and correlations.

Thus, a 95% 'concentration ellipsoid' can be constructed from the sample of $N_1$=134 normals based on G genes which be expected to contain 95% of the normals. Moreover, if these genes are selected in a way that the MVN (multivariate normal) parameters (means, variances, correlations) differ in significant ways from the non-normal population being studied, and the sample sizes $N_1$ and $N_2$ (for the non-normals) were sufficiently large, it would be expected that the gene expressions for each non-normal case might fall outside the 95% normal confidence bounds.

Example 9

Relationship Between Gene Expressions and Clinical Outcomes for Washed-Out RA Subjects In a related study, various clinical outcomes including (American College of Rheumatology score (ACR), C-Reactive Protein levels (W-CRP), Disease Activity Score (W-DAS), Erythrocyte Sedmintation rate (W-ESR), Health Assessment Questionnaire (W-HAQ), Physician's assessment of disease (PhysAssessDisease), Subject's assessment of disease (SubAssessDisease), Subject's assessment of pain (SubAssessPain), swollen joint count (SwollJoints), and tender joint count (TenderJoints) were considered, with a view to identifying the relationships between the gene expressions at baseline and the clinical outcomes.

Since these outcome variables are not normally distributed, an ordinal logistic regression model was used (see e.g., Magidson, 1996) rather than a linear regression to predict them as a function of the gene expressions. Again, the stepwise procedure within the GOLDMineR program was used to perform the analysis. Because of the small sample size (N=22), the number of predictors that were allowed to enter into the model was limited to two to reduce the likelihood of obtaining spurious results.

During baseline (time=0), significant relationships were found between 8 of the 10 clinical outcomes. However, the genes found to be significant were not necessarily those that were found to discriminate between Normals and RAs. Regarding subject's assessment of disease, TLR2 is the gene singled out as most highly related to this outcome (p=0.01). As noted earlier, TLR2 is the most significant discriminator between RAs and normals. Other outcomes show significant relationships with other genes. For example, if the goal were to predict W-CRP or the SwollenJoints score, the best of the 48 genes would be IL8. However, IL8 is not significantly different between RAs and Normals (IL8 expression has a mean value of 21.0 for both groups). Regarding the prediction of Swollen Joints score, TLR2 enters into the linear regression second, following IL8. Swollen joint score increases with higher values on IL8 and lower values on TLR2. See Table 15 for a summary of results from a stepwise ordinal logit model. Thus while the relatively small sample of RAs does not allow for definitive conclusions, it is clear that there are strong relationships between the clinical outcomes and the gene expressions. Only 2 measures (Sharp score and HAQ) were not found to be significantly related to any of the 48 genes measured.

Example 10

Simulated Effect of Error in Data

A study simulating the effect of error in gene expression data was conducted. For simplicity the study was limited to just 1 realization (using only a single set of random numbers as opposed to hundreds or thousands of replications), and added the random error quantities to just the 3 genes used in the RA vs. Normals model discussed above. This random error generation was applied 4 times, generating what might be consider a 'small' amount of error (s=0.2 below), moderate (s=0.5), large (s=1) and very large (s=2), where s is measured in standard deviation units.

To relate the magnitude of "s" to the ability of the less precise measure to reproduce the more precise measure, for each of the 3 genes, Table 16 relates each value of "s" to the average % CD standard used in analysis, and Table 17 below relates "s" to the percentage of the variance of the more precise measure that is reproduced by the less precise measure. For these purposes, the "% CD standard" is the standard deviation s of the gene expression data divided by its mean. Table 16 calculates these average '% CD' values based on the mean for each of the 3 genes.

Let $Y(j)$ represent the measure developed according to the practices described herein for the expression of gene j. For subject i, among a sample of N=156 subjects (includes both the $N_1$=134 Normals and the $N_2$=22 RAs), for each of 3 genes observed $y_i(j)$, j=1, 2, 3, so vector $Y(j)=[y_1(j), y_2(j), \ldots, y_N(j)]$ was observed, for each gene j=1, 2, 3. Supposing that there is a less precise measurement of gene j, $Y'(j)$, which is simulated from the measured data by adding a random error "e" that is independently and identically distributed according to the normal distribution with mean 0 and standard deviation "s", is as follows:

$$y_i'(j) = y_i(j) + e_i(j), I=1,2, \ldots, N; j=1,2,3$$

The larger the value of "s", the larger the contribution made by the error, i.e., the more error is in the data. Taking the mean equivalent to 0 makes the less precise measure unbiased, that is, the difference between the two measurements is only that one is more precise than the other. Four sets of data were generated, corresponding to the values s=0.2, 0.5, 1.0 and 2.0 which yield successively larger amounts of error.

$Y'(j)=Y(j)+$error, where 'error' is independently and identically distributed as Normal with mean 0 and standard deviation s. The higher the value of "s", the more error in the measurement. Since the mean error is zero, it was assumed that the less precise alternative measurement is unbiased. (Note: The square of the correlation between $Y(j)$ and $Y'(j)$ is a measure of the percentage of the variance of $Y(j)$ that is captured by $Y'(j)$. The formula for this is $VAR(Y)/[VAR(Y)+s^2]$. These quantities are displayed in Table 17 below, followed by the observed squared correlations based on the generated data in Table 18.)

The results of this simulation show that accurate measurement is critical to discrimination. The standard deviation of the measurements increases as larger amounts of error are added (see Table 19). For example, for TLR2, the standard deviation increases from 0.79 to 0.83, to 0.90, to 1.25 to 1.93. The R-square statistic, which is a measure of the extent to which the 3-genes discriminate between the RAs and Normals goes from 1 (perfect discrimination) to 0.87, to 0.55, to 0.33 to 0.23 as larger amounts of error are added to the data. Only for the situation where there is a 'small' amount of error, are 2-classes distinguished by a latent class analysis. That is, in the other situations the data does not contain sufficient differentiation to identify that it comes from 2 populations. Using the 'small error' data, a latent class analysis would correctly identify 2 classes, but the 2-class model would misclassify 2 normals and 14 RAs. If the linear algorithm from the original model were used with these data, 2 RAs and 2 Normals would be misclassified as shown in FIG. 76. If the original linear algorithm were applied to the simulated data, increasing numbers of RAs and Normals would be misclassified, as the amount of error is increased. Specifically, 4 misclassifications occur with the small amounts of error (2 RAs and 2 Normals), increasing to 12, 42 and 47 respectively as more error is added.

FIGS. 38-41 show the plots corresponding to FIG. 29 as applied to the simulated data.

These data support that Gene Expression Profiles with sufficient precision and calibration as described herein (1) can determine subsets of individuals with a known biological condition, particularly individuals with rheumatoid arthritis or individuals with inflammatory conditions related to rheumatoid arthritis; (2) may be used to monitor the response of patients to therapy; (3) may be used to assess the efficacy and safety of therapy; and (4) may be used to guide the medical management of a patient by adjusting therapy to bring one or more relevant Gene Expression Profiles closer to a target set of values, which may be normative values or other desired or achievable values.

Gene Expression Profiles are used for characterization and monitoring of treatment efficacy of individuals with rheumatoid arthritis, or individuals with inflammatory conditions related to rheumatoid arthritis. Use of the algorithmic and statistical approaches discussed above to achieve such identification and to discriminate in such fashion is within the scope of various embodiments herein.

The references listed below are hereby incorporated herein by reference.

REFERENCES

Magidson, J. *GOLDMineR User's Guide* (1998). Belmont, Mass.: Statistical Innovations Inc.

Vermunt J. K. and J. Magidson. *Latent GOLD 4.0 User's Guide*. (2005) Belmont, Mass.: Statistical Innovations Inc.

Vermunt J. K. and J. Magidson. *Technical Guide for Latent GOLD 4.0: Basic and Advanced* (2005) Belmont, Mass.: Statistical Innovations Inc.

Vermunt J. K. and J. Magidson. *Latent Class Cluster Analysis* in (2002) J. A. Hagenaars and A. L. McCutcheon (eds.), *Applied Latent Class Analysis,* 89-106. Cambridge: Cambridge University Press.

Magidson, J. "Maximum Likelihood Assessment of Clinical Trials Based on an Ordered Categorical Response." (1996) Drug Information Journal, Maple Glen, Pa.: Drug Information Association, Vol. 30, No. 1, pp 143-170.

TABLE 1

Rheumatoid Arthritis or Inflammatory Conditions Related to Rheumatoid Arthritis Gene Expression Panel

| | Symbol | Name | Classification | Description |
|---|---|---|---|---|
| 1 | APAF1 | Apoptotic Protease Activating Factor 1 | Protease activating peptide | Cytochrome c binds to APAF1, triggering activation of CASP3, leading to apoptosis. May also facilitate procaspase 9 auto activation. |
| 2 | BCL2 | B-cell CLL/lymphoma 2 | Apoptosis Inhibitor - cell cycle control - oncogenesis | Blocks apoptosis by interfering with the activation of caspases |
| 3 | BPI | Bactericidal/permeability-increasing protein | Membrane-bound protease | LPS binding protein; cytotoxic for many gram negative organisms; found in myeloid cells |
| 4 | C1QA | Complement component 1, q subcomponent, alpha polypeptide | Proteinase/proteinase inhibitor | Serum complement system; forms C1 complex with the proenzymes c1r and c1s |
| 5 | CASP1 | Caspase 1 | Proteinase | Activates IL1B; stimulates apoptosis |
| 6 | CASP3 | Caspase 3 | Proteinase/Proteinase Inhibitor | Involved in activation cascade of caspases responsible for apoptosis - cleaves CASP6, CASP7, CASP9 |
| 7 | CASP9 | Caspase 9 | Proteinase | Binds with APAF1 to become activated; cleaves and activates CASP3 |
| 8 | CCL1 | Chemokine (C-C Motif) ligand 1 | Cytokines/Chemokines/Growth Factors | Secreted by activated T cells; chemotactic for monocytes, but not neutrophils; binds to CCR8 |
| 9 | CCL2 | Chemokine (C-C Motif) ligand 2 | Cytokines-chemokines-growth factors | CCR2 chemokine; Recruits monocytes to areas of injury and infection; Upregulated in liver inflammation; Stimulates IL-4 production; Implicated in diseases involving monocyte, basophil infiltration of tissue (e.g,. psoriasis, rheumatoid arthritis, atherosclerosis) |
| 10 | CCL3 | Chemokine (C-C motif) ligand 3 | Cytokines/Chemokines/Growth Factors | AKA: MIP1-alpha; monkine that binds to CCR1, CCR4 and CCR5; major HIV-suppressive factor produced by CD8 cells. |
| 11 | CCL4 | Chemokine (C-C Motif) ligand 4 | Cytokines/Chemokines/Growth Factors | Inflammatory and chemotactic monokine; binds to CCR5 and CCR8 |
| 12 | CCL5 | Chemokine (C-C Motif) ligand 5 | Cytokines/Chemokines/Growth Factors | Binds to CCR1, CCR3, and CCR5 and is a chemoattractant for blood monocytes, memory T-helper cells and eosinophils; |

TABLE 1-continued

Rheumatoid Arthritis or Inflammatory Conditions Related to Rheumatoid Arthritis Gene Expression Panel

| | Symbol | Name | Classification | Description |
|---|---|---|---|---|
| 13 | CCR3 | Chemokine (C-C motif) receptor 3 | Chemokine receptor | A major HIV-suppressive factor produced by CD8-positive T-cells C-C type chemokine receptor (Eotaxin receptor) binds to Eotaxin, Eotaxin-3, MCP-3, MCP-4, SCYA5/RANTES and mip-1 delta thereby mediating intracellular calcium flux. Alternative co-receptor with CD4 for HIV-1 infection. Involved in recruitment of eosinophils. Primarily a Th2 cell chemokine receptor. |
| 14 | CD14 | CD14 antigen | Cell Marker | LPS receptor used as marker for monocytes |
| 15 | CD19 | CD19 antigen | Cell Marker | AKA Leu 12; B cell growth factor |
| 16 | CD3Z | CD3 antigen, zeta polypeptide | Cell Marker | T-cell surface glycoprotein |
| 17 | CD4 | CD4 antigen (p55) | Cell Marker | Helper T-cell marker |
| 18 | CD86 | CD 86 Antigen (cD 28 antigen ligand) | Cell signaling and activation | AKA B7-2; membrane protein found in B lymphocytes and monocytes; co-stimulatory signal necessary for T lymphocyte proliferation through IL2 production. |
| 19 | CD8A | CD8 antigen, alpha polypeptide | Cell Marker | Suppressor T cell marker |
| 20 | CKS2 | CDC28 protein kinase regulatory subunit 2 | Cell signaling and activation | Essential for function of cyclin-dependent kinases |
| 21 | CSF2 | Granulocyte-monocyte colony stimulating factor | Cytokines/ Chemokines/ Growth Factors | AKA GM-CSF; Hematopoietic growth factor; stimulates growth and differentiation of hematopoietic precursor cells from various lineages, including granulocytes, macrophages, eosinophils, and erythrocytes |
| 22 | CSF3 | Colony stimulating factor 3 (granulocyte) | Cytokines/ Chemokines/ Growth Factors | AKA GCSF controls production ifferentiation and function of granulocytes. |
| 23 | CSPG2 | Chondroitin Sulfate Proteoglycan 2 (versican) | Cell Adhesion/Cell Recognition | Versican is 1 of the main genes upregulated after vascular injury |
| 24 | CXCL1 | Chemokine (C-X-C-motif) ligand 1 | Cytokines/ Chemokines/ Growth Factors | Melanoma growth stimulating activity, alpha; Chemotactic proinflammatory activation-inducible cytokine. |
| 25 | CXCL3 | Chemokine (C-X-C-motif) ligand 3 | Cytokines/ Chemokines/ Growth Factors | Chemotactic proinflammatory activation-inducible cytokine, acting primarily upon hemopoietic cells in immunoregulatory processes, may also play a role in inflammation and exert its effects on endothelial cells in an autocrine fashion. |
| 26 | CXCL10 | Chemokine (C-X-C motif) ligand 10 | Cytokines/ Chemokines/ Growth Factors | AKA: Gamma IP10; interferon inducible cytokine IP10; SCYB10; Ligand for CXCR3; binding causes stimulation of monocytes, NK cells; induces T cell migration |
| 27 | DPP4 | Dipeptidyl-peptidase 4 | Membrane protein; exopeptidase | Removes dipeptides from unmodified, n-terminus prolines; has role in T cell activation |

TABLE 1-continued

Rheumatoid Arthritis or Inflammatory Conditions Related to Rheumatoid Arthritis Gene Expression Panel

| | Symbol | Name | Classification | Description |
|---|---|---|---|---|
| 28 | ELA2 | Elastase 2, neutrophil | Protease | Modifies the functions of NK cells, monocytes and granulocytes |
| 29 | EGR1 | Early Growth Response 1 | Tumor Suppressor | The protein encoded by this gene belongs to the EGR family of C2H2-type zinc-finger proteins. It is a nuclear protein and functions as a transcriptional regulator. |
| 30 | HIST1H1C | Histone 1, H1c | Basic nuclear protein | Responsible for the nucleosome structure within the chromosomal fiber in eukaryotes; may attribute to modification of nitrotyrosine-containing proteins and their immunoreactivity to antibodies against nitrotyrosine |
| 31 | HLA-DRA | major histocompatibility complex, class II, DR alpha | Membrane protein; antigen processing | HLA-DRA is one of the HLA class II alpha chain paralogues. It plays a central role in the immune system by presenting peptides derived from extracellular proteins |
| 32 | HMOX1 | Heme oxygenase (decycling) 1 | Enzyme/Redox | Endotoxin inducible |
| 33 | HSPA1A | Heat shock protein 70 | Cell Signaling and activation | heat shock protein 70 kDa; Molecular chaperone, stabilizes AU rich mRNA |
| 34 | ICAM1 | Intercellular adhesion molecule 1 | Cell Adhesion/Matrix Protein | Endothelial cell surface molecule; regulates cell adhesion and trafficking, unregulated during cytokine stimulation |
| 35 | IFI16 | Gamma interferon inducible protein 16 | Cell signaling and activation | Transcriptional repressor |
| 36 | IFNA2 | Interferon, alpha 2 | Cytokines/Chemokines/Growth Factors | interferon produced by macrophages with antiviral effects |
| 37 | IFNG | Interferon, Gamma | Cytokines/Chemokines/Growth Factors | Pro- and anti-inflammatory activity; TH1 cytokine; nonspecific inflammatory mediator; produced by activated T-cells. |
| 38 | IL10 | Interleukin 10 | Cytokines/Chemokines/Growth Factors | Anti-inflammatory; TH2; suppresses production of proinflammatory cytokines |
| 39 | IL12B | Interleukin 12 p40 | Cytokines/Chemokines/Growth Factors | Proinflammatory; mediator of innate immunity, TH1 cytokine, requires co-stimulation with IL-18 to induce IFN-g |
| 40 | IL13 | Interleukin 13 | Cytokines/Chemokines/Growth Factors | Inhibits inflammatory cytokine production |
| 41 | IL18 | Interleukin 18 | Cytokines/Chemokines/Growth Factors | Proinflammatory, TH1, innate and acquired immunity, promotes apoptosis, requires co-stimulation with IL-1 or IL-2 to induce TH1 cytokines in T- and NK-cells |
| 42 | IL18RI | Interleukin 18 receptor 1 | Membrane protein | Receptor for interleukin 18; binding the agonist leads to activation of NFKB-B; belongs to IL1 family but does not bind IL1A or IL1B. |
| 43 | IL1A | Interleukin 1, alpha | Cytokines-chemokines-growth factors | Proinflammatory; constitutively and inducibly expressed in variety of cells. Generally cytosolic and released only during severe inflammatory disease |

TABLE 1-continued

Rheumatoid Arthritis or Inflammatory Conditions Related to Rheumatoid Arthritis Gene Expression Panel

| | Symbol | Name | Classification | Description |
|---|---|---|---|---|
| 44 | IL1B | Interleukin 1, beta | Cytokines/ Chemokines/ Growth Factors | Proinflammatory; constitutively and inducibly expressed by many cell types, secreted |
| 45 | IL1R1 | Interleukin 1 receptor, type I | Cell signaling and activation | AKA: CD12 or IL1R1RA; Binds all three forms of interleukin-1 (IL1A, IL1B and IL1RA). Binding of agonist leads to NFKB activation |
| 46 | IL1RN | Interleukin 1 Receptor Antagonist | Cytokines/ Chemokines/ Growth Factors | IL1 receptor antagonist; Anti-inflammatory; inhibits binding of IL-1 to IL-1 receptor by binding to receptor without stimulating IL-1-like activity |
| 47 | IL2 | Interleukin 2 | Cytokines/ Chemokines/ Growth Factors | T-cell growth factor, expressed by activated T-cells, regulates lymphocyte activation and differentiation; inhibits apoptosis, TH1 cytokine |
| 48 | IL4 | Interleukin 4 | Cytokines/ Chemokines/ Growth Factors | Anti-inflammatory; TH2; suppresses proinflammatory cytokines, increases expression of IL-1RN, regulates lymphocyte activation |
| 49 | IL5 | Interleukin 5 | Cytokines/ Chemokines/ Growth Factors | Eosinophil stimulatory factor; stimulates late B cell differentiation to secretion of Ig |
| 50 | IL6 | Interleukin 6 (interferon, beta 2) | Cytokines-chemokines-growth factors | Pro- and anti-inflammatory activity, TH2 cytokine, regulates hematopoietic system and activation of innate response |
| 51 | IL8 | Interleukin 8 | Cytokines-chemokines-growth factors | Proinflammatory, major secondary inflammatory mediator, cell adhesion, signal transduction, cell-cell signaling, angiogenesis, synthesized by a wide variety of cell types |
| 52 | IRF7 | Interferon regulatory factor 7 | Transcription Factor | Regulates transcription of interferon genes through DNA sequence-specific binding. Diverse roles include virus-mediated activation of interferon, and modulation of cell growth, differentiation, apoptosis, and immune system activity. |
| 53 | LTA | Lymphotoxin alpha (TNF superfamily, member 1) | Cytokine | Cytokine secreted by lymphocytes and cytotoxic for a range of tumor cells; active in vitro and in vivo |
| 54 | LTB | Lymphotoxin beta (TNFSF3) | Cytokine | Inducer of inflammatory response and normal lymphoid tissue development |
| 55 | JUN | v-jun avian sarcoma virus 17 oncogene homolog | Transcription factor-DNA binding | Proto-oncoprotein; component of transcription factor AP-1 that interacts directly with target DNA sequences to regulate gene expression |
| 56 | MEF2C | MADS box transcription enhancer factor 2, polypeptide C (myocyte enhancer factor 2C) | Transcription factor-DNA binding | Ttranscription activator which binds specifically to the mef2 element present in the regulatory regions of many muscle-specific genes |
| 57 | MIF | Macrophage migration inhibitory factor | Cell signaling and growth factor | AKA; GIF; lymphokine, regulators macrophage functions through suppression of anti- |

TABLE 1-continued

Rheumatoid Arthritis or Inflammatory Conditions Related to Rheumatoid Arthritis Gene Expression Panel

| | Symbol | Name | Classification | Description |
|---|---|---|---|---|
| 58 | MMP9 | Matrix metalloproteinase 9 | Proteinase/ Proteinase Inhibitor | inflammatory effects of glucocorticoids AKA gelatinase B; degrades extracellular matrix molecules, secreted by IL-8-stimulated neutrophils |
| 59 | N33 | tumor suppressor candidate 3 | Tumor Suppressor | Integral membrane protein. Associated with homozygous deletion in metastatic prostate cancer. |
| 60 | NFKB1 | Nuclear factor of kappa light polypeptide gene enhancer in B-cells 1 (p105) | Transcription Factor | p105 is the precursor of the p50 subunit of the nuclear factor NFKB, which binds to the kappa-b consensus sequence located in the enhancer region of genes involved in immune response and acute phase reactions; the precursor does not bind DNA itself |
| 61 | NFKBIB | Nuclear factor of kappa light polypeptide gene enhancer in B-cells inhibitor, beta | Transcription Regulator | Inhibits/regulates NFKB complex activity by trapping NFKB in the cytoplasm. Phosphorylated serine residues mark the NFKBIB protein for destruction thereby allowing activation of the NFKB complex. |
| 62 | PF4 | Platelet Factor 4 (SCYB4) | Chemokine | PF4 is released during platelet aggregation and is chemotactic for neutrophils and monocytes. PF4's major physiologic role appears to be neutralization of heparin-like molecules on the endothelial surface of blood vessels, thereby inhibiting local antithrombin III activity and promoting coagulation. |
| 63 | PI3 | Proteinase inhibitor 3 skin derived | Proteinase inhibitor-protein binding extracellular matrix | aka SKALP; Proteinase inhibitor found in epidermis of several inflammatory skin diseases; it's expression can be used as a marker of skin irritancy |
| 64 | PLA2G7 | Phospholipase A2, group VII (platelet activating factor acetylhydrolase, plasma) | Enzyme/Redox | Platelet activating factor |
| 65 | LTA | lymphotoxin alpha (TNF superfamily, member 1) | Cytokines/ Chemokines/ Growth Factors | LTA mediates a large variety of inflammatory, immunostimulatory, and antiviral responses. LTA is also plays a role in apoptosis |
| 66 | PTGS2 | Prostaglandin-endoperoxide synthase 2 | Enzyme | Cytokine secreted by lymphocytes and cytotoxic for a range of tumor cells; active in vitro and in vivo |
| 67 | PTX3 | Pentaxin-related gene, rapidly induced by IL-1 beta | Acute Phase Protein | Inducer of inflammatory response and normal lymphoid tissue development |
| 68 | RAD52 | RAD52 (S. cerevisiae) homolog | DNA binding proteinsor | Involved in DNA double stranded break repair and meiotic/mitotic recombination |
| 69 | SERPINE1 | Serine (or cysteine) protease inhibitor, clade B (ovalbumin), member 1 | Proteinase/ Proteinase Inhibitor | Plasminogen activator inhibitor-1/PAI-1 |
| 70 | SLC7A1 | Solute carrier family 7, member 1 | Membrane protein; permease | High affinity, low capacity permease invovled in the transport of positively charged amino acids |

TABLE 1-continued

Rheumatoid Arthritis or Inflammatory Conditions Related to Rheumatoid Arthritis Gene Expression Panel

| | Symbol | Name | Classification | Description |
|---|---|---|---|---|
| 71 | STAT3 | Signal transduction and activator of transcription 3 | Transcription factor | AKA APRF: Transcription factor for acute phase response genes; rapidly activated in response to certain cytokines and growth factors; binds to IL6 response elements |
| 72 | TGFB1 | Transforming growth factor, beta 1 | Cytokines/ Chemokines/ Growth Factors | Pro- and antiinflammatory activity, anti-apoptotic; cell-cell signaling, can either inhibit or stimulate cell growth |
| 73 | TGFBR2 | Transforming growth factor, beta receptor II | Membrane protein | AKA: TGFR2; membrane protein involved in cell signaling and activation, ser/thr protease; binds to DAXX. |
| 74 | TIMP1 | Tissue inhibitor of metalloproteinase 1 | Proteinase/ Proteinase Inhibitor | Irreversibly binds and inhibits metalloproteinases, such as collagenase |
| 75 | TLR2 | Toll-like receptor 2 | Cell signaling and activation | mediator of petidoglycan and lipotechoic acid induced signalling |
| 76 | TNF | Tumor necrosis factor | Cytokine/tumor necrosis factor receptor ligand | Negative regulation of insulin action. Produced in excess by adipose tissue of obese individuals - increases IRS-1 phosphorylation and decreases insulin receptor kinase activity. |
| 77 | TNFRSF7 | Tumor necrosis factor receptor superfamily, member 7 | Membrane protein; receptor | Receptor for CD27L; may play a role in activation of T cells |
| 78 | TNFSF13B | Tumor necrosis factor (ligand) superfamily, member 13b | Cytokines/ Chemokines/ Growth Factors | B cell activating factor, TNF family |
| 79 | TNFRSF13B | Tumor necrosis factor receptor superfamily, member 13, subunit beta | Cytokines/ Chemokines/ Growth Factors | B cell activating factor, TNF family |
| 80 | TNFSF5 | Tumor necrosis factor (ligand) superfamily, member 5 | Cytokines/ Chemokines/ Growth Factors | Ligand for CD40; expressed on the surface of T cells. It regulates B cell function by engaging CD40 on the B cell surface. |
| 81 | TNFSF6 | Tumor necrosis factor (ligand) superfamily, member 6 | Cytokines/ Chemokines/ Growth Factors | AKA FasL; Ligand for FAS antigen; transduces apoptotic signals into cells |

TABLE 2

Inflammation Gene Expression Panel

| | Symbol | Name | Classification | Description |
|---|---|---|---|---|
| 1 | ADAM 17 | a disintegrin and metalloproteinase domain 17 (tumor necrosis factor, alpha, converting enzyme) | Membrane protein, cell signaling | Tumor necrosis factor-alpha converting enzyme |
| 2 | ALOX5 | arachidonate 5-lipoxygenase | Inflammatoy Response | Synthesizes leukotrienes from arachidonic acid; member of lipoxygenase gene family |
| 3 | ANXA11 | annexin A11 | Immune response, Calcium ion binding | 56-kD antigen recognized by sera from patients with various autoimmune diseases; member of annexin family (calcium-dependent phospholipid-binding proteins) |

TABLE 2-continued

Inflammation Gene Expression Panel

| | Symbol | Name | Classification | Description |
|---|---|---|---|---|
| 4 | APAF1 | apoptotic Protease Activating Factor 1 | Protease activating peptide | Cytochrome c binds to APAF1, triggering activation of CASP3, leading to apoptosis. May also facilitate procaspase 9 autoactivation. |
| 5 | BAX | BCL2-associated X protein | Cell cycle regulation, apoptosis induction | Forms a heterodimer with BCL2 and functions as an apoptotic activator; protein is reported to interact with, and increase the opening of, the mitochondrial voltage-dependent anion channel (VDAC), which leads to the loss in membrane potential and the release of cytochrome c; member of BCL2 protein family |
| 6 | C1QA | Complement component 1, q subcomponent, alpha polypeptide | Proteinase/ Proteinase Inhibitor | encodes the A-chain polypeptide of human complement subcomponent C1q |
| 7 | CASP1 | caspase 1, apoptosis-related cysteine peptidase (interleukin 1, beta, convertase) | Proteinase | Proteolytically cleaves and activates the inactive precursor of interleukin-1; induces cell apoptosis; member of the cysteine-aspartic acid protease (caspase) family |
| 8 | CASP3 | caspase 3, apoptosis-related cysteine peptidase | Proteinase | Cleaves and activates caspases 6, 7 and 9. It is the predominant caspase involved in the cleavage of amyloid-beta 4A precursor protein; member of the cysteine-aspartic acid protease (caspase) family |
| 9 | CCL2 | chemokine (C-C motif) ligand 2 | Cytokines/ Chemokines/ Growth Factors | Displays chemotactic activity for monocytes and basophils but not for neutrophils or eosinophils; binds to chemokine receptors CCR2 and CCR4, member of cytokine family (involved in immunoregulatory and inflammatory processes) |
| 10 | CCL3 | chemokine (C-C motif) ligand 3 | Cytokines/ Chemokines/ Growth Factors | Monokine involved in the acute inflammatory state in the recruitment and activation of polymorphonuclear leukocytes |
| 11 | CCL5 | chemokine (C-C motif) ligand 5 | Cytokines/ Chemokines/ Growth Factors | Chemoattractant for blood monocytes, memory T helper cells and eosinophils; causes the release of histamine from basophils and activates eosinophils; one of the major HIV-suppressive factors produced by CD8+ cells; functions as one of the natural ligands for the chemokine receptor CCR5 and it suppresses in vitro replication of the R5 strains of HIV-1, which use CCR5 as a coreceptor |
| 12 | CCR3 | chemokine (C-C motif) receptor 3 | Chemokine receptor | Binds and responds to a variety of chemokines, including eotaxin (CCL11), eotaxin-3 (CCL26), MCP-3 (CCL7), MCP-4 (CCL13), and RANTES (CCL5); highly expressed in eosinophils and basophils, and detected in TH1&TH2 cells and airway epithelial cells; may contribute to the |

TABLE 2-continued

Inflammation Gene Expression Panel

| | Symbol | Name | Classification | Description |
|---|---|---|---|---|
| | | | | accumulation and activation of eosinophils and other inflammatory cells in the allergic airway; also known to be an entry co-receptor for HILV-1; member of family 1 of the G protein-coupled receptors |
| 13 | CCR5 | chemokine (C-C motif) receptor 5 | Chemokine receptor | Expressed by T cells and macrophages - important co-receptor for macrophage-tropic virus, including HIV, to enter host cells; expression also detected in a promyeloblastic cell line, suggesting its role in granulocyte lineage proliferation and differentiation; member of the beta chemokine receptor family |
| 14 | CRP | C-reactive protein, pentraxin-related | Inflammatory Response, acute phase protein | Promotes agglutination, bacterial capsular swelling, phagocytosi and complement fixation through its calcium-dependent binding to phosphorylcholine; can interact with DNA and histones and may scavenge nuclear material released from damaged circulating cells |
| 15 | CTLA4 | cytotoxic T-lymphocyte-associated protein 4 | Membrane protein, Immune response | Costimulatory molecule expressed by activated T cells; binds to B7-1 (CD80; MIM 112203) and B7-2 (CD86; MIM 601020) on antigen-presenting cells and transmits an inhibitory signal to T cells; member of the immunoglobulin superfamily |
| 16 | CXCL10 | chemokine (C-X-C moif) ligand 10 | cytokines-chemokines-growth factors | Ligand for CXCR3; binding causes stimulation of monocytes, NK cells; induces T cell migration |
| 17 | CXCL3 | chemokine (C-X-C motif) ligand 3 | cytokines-chemokines-growth factors | Chemotactic pro-inflammatory activation-inducible cytokine, acting primarily upon hemopoietic cells in immunoregulatory processes |
| 18 | CXCL5 | chemokine (C-X-C motif) ligand 5 | cytokines-chemokines-growth factors | Inflammatory chemokine that belongs to the CXC chemokine family; produced concomitantly with interleukin-8 (IL8) in response to stimulation with either interleukin-1 (IL1) or tumor necrosis factor-alpha (TNFA); involved in neutrophil activation |
| 19 | CXCR3 | chemokine (C-X-C motif) receptor 3 | Chemokine receptor | Binding of chemokines to CXCR3 induces cellular responses that are involved in leukocyte traffic, most notably integrin activation, cytoskeletal changes and chemotactic migration; may participate in the recruitment of inflammatory cells |
| 20 | DPP4 | Dipeptidylpeptidase 4 | Membrane protein; exopeptidase | Removes dipeptides from unmodified, n-terminus prolines; has role in T cell activation |
| 21 | EGR1 | early growth response-1 | Tumor Suppressor | Displays FOS-like induction kinetics in fibroblasts, |

TABLE 2-continued

Inflammation Gene Expression Panel

| | Symbol | Name | Classification | Description |
|---|---|---|---|---|
| | | | | epithelial cells, and lymphocytes, following mitogenic stimulation; coordinated regulation of TGFB1 and fibronectin |
| 22 | ELA2 | elastase 2, neutrophil | Protease | Modifies the functions of NK cells, moncytes and granulocytes |
| 23 | FAIM3 | Fas apoptotic inhibitory molecule 3 | Cellualr defense, apoptosis inhibitor | Novel regulator of Fas-mediated apoptosis; regulator of cell fate in T cells and other hematopoietic lineages |
| 24 | GCLC | glutamate-cysteine ligase, catalytic subunit | Enzyme-cysteine, glutamate metabolism | First rate limiting enzyme of glutathione synthesis; deficiency of gamma-glutamylcysteine synthetase in humans is associated with enzymopathic hemolytic anemia |
| 25 | GZMB | granzyme B (granzyme 2, cytotoxic T-lymphocyte-associated serine esterase 1) | Apoptosis, Cytolysis | Crucial for the rapid induction of target cell apoptosis by CTL in cell-mediated immune response |
| 26 | HLA-DRA | major histocompatibility complex, class II, DR alpha | Membrane protein; antigen processing | Anchored heterodimeric molecule; cell-surface antigen presenting complex |
| 27 | HMGB1 | high-mobility group box 1 | DNA repair, Signal transduction | Binds with high affinity to specific DNA structures such as bent or kinked DNA; considered to be a structural protein of chromatin |
| 28 | ICOS | inducible T-cell co-stimulator | Immune response | Plays role in cell-cell signaling, immune responses, and regulation of cell proliferation; member of CD28 and CTLA-4 cell-surface receptor family |
| 29 | IFI16 | interferon inducible protein 16, gamma | Cell signaling and activation | Transcriptional repressor |
| 30 | IRF1 | interferon regulatory factor 1 | Transcription factor | Activator of interferons alpha and beta transcription; transcription activator of genes induced by interferons alpha, beta, and gamma; regulates apoptosis and tumor-suppressoion; member of interferon regulatory transcription factor (IRF) family |
| 31 | IL1R1 | interleukin 1 receptor, type I | Cell signaling and activation | Receptor for interleukin alpha (IL1A), interleukin beta (IL1B), and interleukin 1 receptor, type I(IL1R1/IL1RA); mediator in cytokine induced immune and inflammatory responses; member of interleukin 1 receptor family |
| 32 | IL23A | interleukin 23, alpha subunit p19 | cytokines-chemokines-growth factors | Activate the transcription activator STAT4, and stimulate the production of interferon-gamma (IFNG); acts on memory CD4(+) T cells |
| 33 | IL32 | interleukin 32 | cytokines-chemokines-growth factors | Induces the production of TNFalpha from macrophage cells; member of cytokine family |
| 34 | LTA | lymphotoxin alpha (TNF superfamily, member 1) | Cytokine | Cytokine secreted by lymphocytes and cytotoxic for a range of tumor cells; active in vitro and in vivo |

TABLE 2-continued

Inflammation Gene Expression Panel

| | Symbol | Name | Classification | Description |
|---|---|---|---|---|
| 35 | MAP3K1 | mitogen-activated protein kinase kinase kinase 1 | Protein serine/threonine kinase | Integrates cellular responses to a number of mitogenic and metabolic stimuli, including insulin and many growth factors |
| 36 | MAPK14 | mitogen-activated protein kinase 14 | Protein serine/threonine kinase | Binds to TRAF2 and stimulates NF-kappaB activity |
| 37 | MHC2TA | class II, major histocompatibility complex, transactivator | Transcription factor, Immune response | AKA CIITA; Positive regulator of class II major histocompatibility complex gene transcription in the nucleus |
| 38 | MIF | macrophage migration inhibitory factor (glycosylation-inhibiting factor) | Cell signaling and growth factor | AKA; GIF; lymphokine, regulators macrophage functions through suppression of anti-inflammatory effects of glucocorticoids |
| 39 | MMP12 | matrix metallopeptidase 12 (macrophage elastase) | Proteinase/Proteinase Inhibitor | Involved in the breakdown of extracellular matrix in normal physiological processes and in disease processes - specifically the degradation of soluble and insoluble elastin |
| 40 | MMP8 | matrix metallopeptidase 8 (neutrophil collagenase) | Proteinase/Proteinase Inhibitor | Involved in the breakdown of extracellular matrix in normal physiological processes and in disease processes - specifically the degradation of type I, II and III collagens |
| 41 | MNDA | myeloid cell nuclear differentiation antigen | Transcription factor, Cellular defense respnse | Detected only in nuclei of cellls of the granulocyte-monocyte lineage; participates in blood cell-specific responses to interferons |
| 42 | MPO | myeloperoxidase | Enzyme, Apoptosis inhibitor | Part of the host defense system of human polymorphonuclear leukocytes, responsible for microbicidal activity against a wide range of organisms |
| 43 | MYC | v-myc myelocytomatosis viral oncogene homolog (avian) | Transcription factor, Cell proliferation | Promotes cell proliferation and transformation by activating growth-promoting genes; activates of telomerase; activates transcription as part of a heteromeric complex with MAX |
| 44 | NFKB1 | nuclear factor of kappa light polypeptide gene enhancer in B-cells 1 (p105) | Transcription factor | Encodes a 105 kD protein which can undergo cotranslational processing by the 26S proteasome to produce a 50 kD protein. The 105 kD protein is a Rel protein-specific transcription inhibitor and the 50 kD protein is a DNA binding subunit of the NF-kappa-B (NFKB) protein complex; activated NFKB translocates into the nucleus and stimulates the expression of genes involved in a wide variety of biological functions |
| 45 | PLA2G2A | phospholipase A2, group IIA (platelets, synovial fluid) | Enzyme-lipid catabolism | Regulates phospholipid metabolism in biomembranes, including eicosanoid biosynthesis; catalyzes the calcium-dependent hydrolysis of the 2-acyl groups in 3-sn-phosphoglycerides. |
| 46 | PLAUR | plasminogen activator, | Signal transduction, | Localizes and promoes plasmin formation; binds |

TABLE 2-continued

Inflammation Gene Expression Panel

| | Symbol | Name | Classification | Description |
|---|---|---|---|---|
| | | urokinase receptor | chemotaxis | urokinase plasminogen activator and permits the activation of the receptor-bound pro-enzyme by plasmin |
| 47 | PRTN3 | proteinase 3 (serine proteinase, neutrophil, Wegener granulomatosis autoantigen) | Regulation of cell proliferation, collagen catabolism | Cleaves elastin; key protease for factor-independent growth of hematopoietic cells |
| 48 | PTX3 | pentraxin-related gene, rapidly induced by IL-1 beta | Acute Phase Protein | Novel marker of inflammatory reactions; IL1b-TNF inducible protein found in endothelial cells |
| 49 | SERPINA3 | serine (or cysteine) proteinase inhibitor, clade A (alpha-1 antiproteinase, antitrypsin), member 1 | Acute phase response, Inflammatory response | Plasma protease inhibitor and member of the serine protease inhibitor class; tissue specific polymorphisms that influence protease targeting |
| 50 | SSI-3 | suppressor of cytokine signaling 3 | Protein kinase inhibitor, apoptosis inhibitor, signal transduction | Cytokine-inducible negative regulators of cytokine signaling; member of the STAT-induced STAT inhibitor (SSI) family, also known as suppressor of cytokine signaling (SOCS) family |
| 51 | TLR2 | toll-like receptor 2 | Cell Signaling and Activation | Mediator of petidoglycan and lipotechoic acid induced signaling |
| 52 | TLR4 | toll-like receptor 4 | Cell Signaling and Activation | Member of the Toll-like receptor (TLR) family which plays a fundamental role in pathogen recognition and activation of innate immunity; recognizes pathogen-associated molecular patterns (PAMPs) that are expressed on infectious agents, and mediates the production of cytokines necessary for the development of effective immunity |
| 53 | TNFRSF17 | tumor necrosis factor receptor superfamily, member 17 | Cytokines/ Chemokines/ Growth Factors | Important for B cell development and autoimmune response; specifically binds to tumor necrosis factor (ligand) superfamily, member 13b (TNFSF13B/TALL-1/BAFF); leads to NF-kappaB and MAPK8/JNK activation; binds to various TRAF family members - may transduce signals for cell survival and proliferation; member of the TNF-receptor superfamily |
| 54 | TNFRSF1A | tumor necrosis factor receptor superfamily, member 1A | Cytokines/ Chemokines/ Growth Factors | Major receptor for the tumor necrosis factor-alpha - activates NF-kappaB, mediates apoptosis, and functions as a regulator of inflammation; member of the TNF-receptor superfamily |
| 55 | TXNRD1 | thioredoxin reductase | Enzyme/ Redox, Signal transduction | Reduces thioredoxins as well as other substrates; involved in selenium metabolism and protection against oxidative stress; member of a family of pyridine nucleotide oxidoreductases |

TABLE 2-continued

Inflammation Gene Expression Panel

| | Symbol | Name | Classification | Description |
|---|---|---|---|---|
| 56 | IL1A | Interleukin 1, alpha | Cytokines/Chemokines/Growth Factors | Proinflammatory; constitutively and inducibly expressed in variety of cells. Generally cytosolic and released only during severe inflammatory disease |
| 57 | IL1B | Interleukin 1, beta | Cytokines/Chemokines/Growth Factors | Proinflammatory; constitutively and inducibly expressed by many cell types, secreted |
| 58 | TNF | Tumor necrosis factor, alpha | Cytokines/Chemokines/Growth Factors | Proinflammatory, TH1, mediates host response to bacterial stimulus, regulates cell growth & differentiation |
| 59 | IL6 | Interleukin 6 (interferon, beta 2) | Cytokines/Chemokines/Growth Factors | Pro- and antiinflammatory activity, TH2 cytokine, regulates hemotopoietic system and activation of innate response |
| 60 | IL8 | Interleukin 8 | Cytokines/Chemokines/Growth Factors | Proinflammatory, major secondary inflammatory mediator, cell adhesion, signal transduction, cell-cell signaling, angiogenesis, synthesized by a wide variety of cell types |
| 61 | IFNG | Interferon gamma | Cytokines/Chemokines/Growth Factors | Pro- and antiinflammatory activity, TH1 cytokine, nonspecific inflammatory mediator, produced by activated T-cells |
| 62 | IL2 | Interleukin 2 | Cytokines/Chemokines/Growth Factors | T-cell growth factor, expressed by activated T cells, regulates lymphocyte activation and differentiation; inhibits apoptosis, TH1 cytokine |
| 63 | IL12B | Interleukin 12 p40 | Cytokines/Chemokines/Growth Factors | Proinflammatory; mediator of innate immunity, TH1 cytokine, requires co-stimulation with IL-18 to induce IFN-g |
| 64 | IL15 | Interleukin 15 | Cytokines/Chemokines/Growth Factors | Proinflammatory; mediates T-cell activation, inhibits apoptosis, synergizes with IL-2 to induce IFN-g and TNF-a |
| 65 | IL18 | Interleukin 18 | Cytokines/Chemokines/Growth Factors | Proinflammatory, TH1, innate and aquired immunity, promotes apoptosis, requires co-stimulation with IL-1 or IL-2 to induce TH1 cytokines in T- and NK-cells |
| 66 | IL4 | Interleukin 4 | Cytokines/Chemokines/Growth Factors | Antiinflammatory; TH2; suppresses proinflammatory cytokines, increases expression of IL-1RN, regulates lymphocyte activation |
| 67 | IL5 | Interleukin 5 | Cytokines/Chemokines/Growth Factors | Eosinophil stimulatory factor; stimulates late B cell differentiation to secretion of Ig |
| 68 | IL10 | Interleukin 10 | Cytokines/Chemokines/Growth Factors | Antiinflammatory; TH2; suppresses production of proinflammatory cytokines |
| 69 | IL13 | Interleukin 13 | Cytokines/Chemokines/Growth Factors | Inhibits inflammatory cytokine production |
| 70 | IL1RN | Interleukin 1 receptor antagonist | Cytokines/Chemokines/Growth Factors | IL1 receptor antagonist; Antiinflammatory; inhibits binding of IL-1 to IL-1 receptor by binding to receptor without stimulating IL-1-like activity |
| 71 | IL18BP | IL-18 Binding Protein | Cytokines/Chemokines/Growth Factors | Implicated in inhibition of early TH1 cytokine responses |

TABLE 2-continued

Inflammation Gene Expression Panel

| | Symbol | Name | Classification | Description |
|---|---|---|---|---|
| 72 | TGFB1 | Transforming growth factor, beta 1 | Cytokines/Chemokines/Growth Factors | Pro- and antiinflammatory activity, anti-apoptotic; cell-cell signaling, can either inhibit or stimulate cell growth |
| 73 | IFNA2 | Interferon, alpha 2 | Cytokines/Chemokines/Growth Factors | interferon produced by macrophages with antiviral effects |
| 74 | CXCL1 | Chemokine (C-X-C motif) Ligand 1 (melanoma growth stimulating activity, alpha) | Cytokines/Chemokines/Growth Factors | Chemotactic for neutrophils, also play a fundamental roles in the development, homeostasis, and function of the immune system |
| 75 | CXCL2 | Chemokine (C-X-C motif) Ligand 2 | Cytokines/Chemokines/Growth Factors | AKA MIP2, SCYB2; Macrophage inflammatory protein produced by moncytes and neutrophils |
| 76 | TNFSF5 | Tumor necrosis factor (ligand) superfamily, member 5 | Cytokines/Chemokines/Growth Factors | ligand for CD40; expressed on the surface of T cells. It regulates B cell function by engaging CD40 on the B cell surface |
| 77 | TNFSF6 | Tumor necrosis factor (ligand) superfamily, member 6 | Cytokines/Chemokines/Growth Factors | AKA FasL; Ligand for FAS antigen; transduces apoptotic signals into cells |
| 78 | CSF3 | Colony stimulating factor 3 (granulocyte) | Cytokines/Chemokines/Growth Factors | AKA GCSF; cytokine that stimulates granulocyte development |
| 79 | CD86 | CD86 molecule | Cell signaling and activation | This gene encodes a type I membrane protein that is a member of the immunoglobulin superfamily. This protein is expressed by antigen-presenting cells, and it is the ligand for two proteins at the cell surface of T cells, CD28 antigen and cytotoxic T-lymphocyte-associated protein 4 |
| 80 | CSF2 | Granulocyte-monocyte colony stimulating factor | Cytokines/Chemokines/Growth Factors | AKA GM-CSF; Hematopoietic growth factor; stimulates growth and differentiation of hematopoietic precursor cells from various lineages, including granulocytes, macrophages, eosinophils, and erythrocytes |
| 81 | TNFSF13B | Tumor necrosis factor (ligand) superfamily, member 13b | Cytokines/Chemokines/Growth Factors | B cell activating factor, TNF family |
| 82 | TNFRSF13B | tumor necrosis factor receptor superfamily, member 13B | Cytokines/Chemokines/Growth Factors | The protein induces activation of the transcription factors NFAT, AP1, and NF-kappa-B and plays a crucial role in humoral immunity by interacting with a TNF ligand |
| 83 | VEGF | vascular endothelial growth factor | Cytokines/Chemokines/Growth Factors | Produced by monocytes |
| 84 | ICAM1 | Intercellular adhesion molecule 1 | Cell Adhesion/Matrix Protein | Endothelial cell surface molecule; regulates cell adhesion and trafficking, upregulated during cytokine stimulation |
| 85 | PTGS2 | Prostaglandin-endoperoxide synthase 2 | Enzyme/Redox | AKA COX2; Proinflammatory, member of arachidonic acid to prostanoid conversion pathway; induced by proinflammatory cytokines |

TABLE 2-continued

Inflammation Gene Expression Panel

| | Symbol | Name | Classification | Description |
|---|---|---|---|---|
| 86 | NOS2A | Nitric oxide synthase 2A | Enzyme/Redox | AKA iNOS; produces NO which is bacteriocidal/tumoricidal |
| 87 | PLA2G7 | Phospholipase A2, group VII (platelet activating factor acetylhydrolase, plasma) | Enzyme/Redox | Platelet activating factor |
| 88 | HMOX1 | Heme oxygenase (decycling) 1 | Enzyme/Redox | Endotoxin inducible |
| 89 | F3 | F3 | Enzyme/Redox | AKA thromboplastin, Coagulation Factor 3; cell surface glycoprotein responsible for coagulation catalysis |
| 90 | CD3Z | CD3 antigen, zeta polypeptide | Cell Marker | T-cell surface glycoprotein |
| 91 | PTPRC | Protein tyrosine phosphatase, receptor type, C | Cell Marker | AKA CD45; mediates T-cell activation |
| 92 | CD14 | CD14 antigen | Cell Marker | LPS receptor used as marker for monocytes |
| 93 | CD4 | CD4 antigen (p55) | Cell Marker | Helper T-cell marker |
| 94 | CD8A | CD8 antigen, alpha polypeptide | Cell Marker | Suppressor T cell marker |
| 95 | CD19 | CD19 antigen | Cell Marker | AKA Leu 12; B cell growth factor |
| 96 | HSPA1A | Heat shock protein 70 | Cell Signaling and activation | heat shock protein 70 kDa |
| 97 | MMP3 | Matrix metalloproteinase 3 | Proteinase/Proteinase Inhibitor | AKA stromelysin; degrades fibronectin, laminin and gelatin |
| 98 | MMP9 | Matrix metalloproteinase 9 | Proteinase/Proteinase Inhibitor | AKA gelatinase B; degrades extracellular matrix molecules, secreted by IL-8-stimulated neutrophils |
| 99 | PLAU | Plasminogen activator, urokinase | Proteinase/Proteinase Inhibitor | AKA uPA; cleaves plasminogen to plasmin (a protease responsible for nonspecific extracellular matrix degradation) |
| 100 | SERPINE1 | Serine (or cysteine) protease inhibitor, clade B (ovalbumin), member 1 | Proteinase/Proteinase Inhibitor | Plasminogen activator inhibitor-1/PAI-1 |
| 101 | TIMP1 | Tissue inhibitor of metalloproteinase 1 | Proteinase/Proteinase Inhibitor | Irreversibly binds and inhibits metalloproteinases, such as collagenase |
| 102 | C1QA | Complement component 1, q subcomponent, alpha polypeptide | Proteinase/Proteinase Inhibitor | Serum complement system; forms C1 complex with the proenzymes c1r and c1s |
| 103 | HLA-DRB1 | Major histocompatibility complex, class II, DR beta 1 | Histocompatibility | Binds antigen for presentation to CD4+ cells |

TABLE 3

Ranking of genes from most to least significant

| | | Normals | | | RAs | | | Tests for significance | |
|---|---|---|---|---|---|---|---|---|---|
| gene id# | gene | N | 0 Mean | Std. Dev. | N | 1 Mean | Std. Dev. | F | 1-way ANOVA p-value | Logit Model p-value |
| 45 | TLR2 | 133 | 16.1 | 0.6 | 22 | 14.6 | 0.6 | 99.3 | 2.5E−18 | 1.0E−16 |
| 31 | MMP9 | 131 | 16.0 | 1.3 | 22 | 13.5 | 1.2 | 70.3 | 3.3E−14 | 1.5E−14 |
| 20 | IFI16 | 133 | 16.8 | 0.8 | 22 | 15.3 | 0.7 | 65.1 | 1.9E−13 | 2.4E−14 |
| 43 | TGFB1 | 133 | 13.2 | 0.6 | 22 | 12.3 | 0.5 | 42.3 | 1.0E−09 | 1.3E−12 |

TABLE 3-continued

Ranking of genes from most to least significant

| | | Normals | | | RAs | | | Tests for significance | |
|---|---|---|---|---|---|---|---|---|---|
| gene id# | gene | N | 0 Mean | Std. Dev. | N | 1 Mean | Std. Dev. | F | 1-way ANOVA p-value | Logit Model p-value |
| 35 | NFKB1 | 134 | 17.4 | 0.7 | 22 | 16.5 | 0.4 | 41.0 | 1.8E−09 | 8.1E−12 |
| 44 | TIMP1 | 134 | 15.0 | 0.6 | 22 | 14.0 | 0.6 | 58.8 | 1.8E−12 | 1.5E−11 |
| 26 | IL1R1 | 133 | 21.1 | 1.0 | 22 | 19.4 | 0.9 | 54.9 | 8.1E−12 | 2.2E−11 |
| 42 | SERPING1 | 133 | 19.2 | 1.2 | 21 | 17.0 | 1.4 | 60.8 | 9.3E−13 | 3.9E−11 |
| 40 | SERPINA1 | 134 | 13.3 | 0.8 | 20 | 12.2 | 0.5 | 35.4 | 1.8E−08 | 4.4E−10 |
| 13 | EGR1 | 133 | 20.4 | 0.6 | 22 | 19.6 | 0.5 | 42.4 | 1.0E−09 | 1.0E−09 |
| 34 | MYC | 133 | 17.3 | 0.7 | 22 | 16.3 | 0.6 | 34.3 | 2.8E−08 | 1.3E−09 |
| 27 | IL1RN | 132 | 16.9 | 0.7 | 22 | 16.0 | 0.5 | 28.5 | 3.3E−07 | 1.2E−08 |
| 10 | CXCL1 | 134 | 20.0 | 0.6 | 22 | 19.2 | 0.5 | 31.6 | 8.5E−08 | 2.9E−08 |
| 37 | PLAUR | 134 | 15.1 | 0.6 | 22 | 14.4 | 0.4 | 28.6 | 3.2E−07 | 3.5E−08 |
| 41 | SERPINE1 | 133 | 22.3 | 0.9 | 22 | 21.1 | 0.8 | 39.0 | 4.1E−09 | 4.7E−08 |
| 33 | MPO | 134 | 21.1 | 0.9 | 22 | 19.6 | 1.5 | 45.1 | 3.4E−10 | 8.1E−08 |
| 5 | CD14 | 132 | 13.9 | 0.7 | 20 | 13.2 | 0.5 | 24.5 | 1.9E−06 | 2.0E−06 |
| 25 | IL1B | 133 | 16.7 | 0.8 | 22 | 15.9 | 0.4 | 23.3 | 3.3E−06 | 2.0E−06 |
| 2 | APAF1 | 134 | 16.5 | 0.5 | 22 | 15.8 | 0.7 | 26.0 | 9.7E−07 | 2.2E−06 |
| 16 | HMGB1 | 133 | 16.3 | 0.7 | 22 | 17.0 | 0.6 | 23.3 | 3.3E−06 | 3.9E−06 |
| 6 | CD19 | 133 | 18.2 | 0.8 | 22 | 19.1 | 1.0 | 25.0 | 1.5E−06 | 5.0E−06 |
| 23 | IL18 | 133 | 20.0 | 0.6 | 22 | 19.3 | 0.6 | 23.0 | 3.8E−06 | 1.9E−05 |
| 11 | CYBB | 133 | 14.0 | 0.6 | 22 | 13.4 | 0.6 | 17.4 | 5.0E−05 | 4.6E−05 |
| 21 | IL10 | 133 | 22.8 | 0.6 | 22 | 22.1 | 0.9 | 18.9 | 2.6E−05 | 8.6E−05 |
| 19 | ICAM1 | 134 | 17.7 | 0.6 | 22 | 17.2 | 0.4 | 12.9 | 4.3E−04 | 1.1E−04 |
| 1 | ADAM17 | 131 | 18.6 | 0.6 | 22 | 18.0 | 0.8 | 15.7 | 1.1E−04 | 1.2E−04 |
| 9 | CD8A | 133 | 15.8 | 0.7 | 22 | 16.5 | 1.0 | 17.2 | 5.4E−05 | 1.3E−04 |
| 39 | PTPRC | 130 | 11.9 | 0.5 | 21 | 11.5 | 0.5 | 11.4 | 9.4E−04 | 0.001 |
| 14 | ELA2 | 131 | 19.9 | 1.3 | 22 | 18.7 | 2.0 | 11.6 | 8.6E−04 | 0.001 |
| 18 | HSPA1A | 132 | 13.9 | 0.9 | 21 | 13.3 | 0.5 | 8.5 | 0.004 | 0.002 |
| 24 | IL18BP | 134 | 16.8 | 0.6 | 22 | 17.2 | 0.7 | 10.7 | 0.001 | 0.003 |
| 30 | LTA | 115 | 20.1 | 0.6 | 19 | 19.7 | 0.8 | 7.6 | 0.007 | 0.007 |
| 48 | TNFSF6 | 130 | 20.4 | 0.7 | 21 | 20.9 | 0.9 | 7.1 | 0.009 | 0.010 |
| 46 | TNF | 132 | 20.7 | 0.9 | 22 | 20.2 | 0.5 | 5.5 | 0.021 | 0.012 |
| 32 | MNDA | 133 | 12.6 | 0.7 | 22 | 12.2 | 0.6 | 5.5 | 0.020 | 0.017 |
| 3 | C1QA | 133 | 20.2 | 1.0 | 22 | 20.7 | 0.8 | 5.3 | 0.023 | 0.018 |
| 17 | HMOX1 | 134 | 16.5 | 0.7 | 22 | 16.1 | 0.7 | 5.3 | 0.023 | 0.019 |
| 7 | CD4 | 134 | 14.8 | 0.5 | 22 | 15.1 | 0.7 | 4.7 | 0.032 | 0.035 |
| 15 | GCLC | 131 | 18.9 | 0.6 | 21 | 18.7 | 0.7 | 1.9 | 0.165 | 0.170 |
| 8 | CD86 | 131 | 17.6 | 0.5 | 21 | 17.8 | 0.7 | 1.8 | 0.185 | 0.180 |
| 28 | IL6 | 134 | 23.5 | 0.3 | 22 | 23.5 | 0.3 | 0.4 | 0.513 | 0.510 |
| 36 | PLA2G7 | 129 | 19.3 | 0.6 | 22 | 19.2 | 1.0 | 0.4 | 0.514 | 0.510 |
| 12 | DPP4 | 134 | 18.4 | 0.6 | 22 | 18.4 | 0.7 | 0.2 | 0.642 | 0.640 |
| 38 | PTGS2 | 128 | 16.7 | 0.6 | 21 | 16.7 | 0.4 | 0.2 | 0.642 | 0.640 |
| 47 | TNFSF5 | 134 | 17.7 | 0.6 | 21 | 17.6 | 0.8 | 0.2 | 0.657 | 0.650 |
| 29 | IL8 | 116 | 21.0 | 1.4 | 21 | 21.0 | 1.4 | 0.0 | 0.880 | 0.880 |
| 22 | IL15 | 133 | 21.5 | 0.6 | 22 | 21.4 | 0.8 | 0.0 | 0.967 | 0.970 |

TABLE 4

Latent class modeling-ranking of p-values form most to least significant
1-gene model estimating RA v. Normal discrimination
(RA, N = 22, Normal N = 134)

| gene 1 | p-value | R-SQ |
|---|---|---|
| TLR2 | 1.00E−16 | 0.535 |
| MMP9 | 1.50E−14 | 0.504 |
| IFI16 | 2.40E−14 | 0.457 |
| TGFB1 | 1.30E−12 | 0.377 |
| NFKB1 | 8.10E−12 | 0.312 |
| TIMP1 | 1.50E−11 | 0.370 |
| IL1R1 | 2.20E−11 | |
| SERPING1 | 3.90E−11 | |
| SERPINA1 | 4.40E−10 | |
| EGR1 | 1.00E−09 | |
| MYC | 1.30E−09 | |
| IL1RN | 1.20E−08 | |
| CXCL1 | 2.90E−08 | |
| PLAUR | 3.50E−08 | |
| SERPINE1 | 4.70E−08 | |
| MPO | 8.10E−08 | |
| CD14 | 2.00E−06 | |
| IL1B | 2.00E−06 | |
| APAF1 | 2.20E−06 | |
| HMGB1 | 3.90E−06 | |
| CD19 | 5.00E−06 | |
| IL18 | 1.90E−05 | |
| CYBB | 4.60E−05 | |
| IL10 | 8.60E−05 | |
| ICAM1 | 0.00011 | |
| ADAM17 | 0.00012 | |
| CD8A | 0.00013 | |
| PTPRC | 0.001 | |
| ELA2 | 0.0012 | |
| HSPA1A | 0.0019 | |
| IL18BP | 0.0031 | |
| LTA | 0.0066 | |
| TNFSF6 | 0.01 | |
| TNF | 0.012 | |
| MNDA | 0.017 | |
| C1QA | 0.018 | |

TABLE 4-continued

Latent class modeling-ranking of p-values form most to least significant 1-gene model estimating RA v. Normal discrimination (RA, N = 22, Normal N = 134)

| gene 1 | p-value | R-SQ |
|---|---|---|
| HMOX1 | 0.019 | |
| CD4 | 0.035 | |
| GCLC | 0.17 | |
| CD86 | 0.18 | |
| IL6 | 0.51 | |
| PLA2G7 | 0.51 | |
| PTGS2 | 0.64 | |
| DPP4 | 0.64 | |
| TNFSF5 | 0.65 | |
| IL8 | 0.88 | |
| IL15 | 0.97 | |

TABLE 5

Latent class modeling-estimating RA v. Normal discrimination using a 2-gene model (RA, N = 22, Normal N = 134)

| gene 1 | gene 2 | Gene 2 Incremental P-Value | % RA | % normal | R-SQ | Gene 1 Incremental P-Value |
|---|---|---|---|---|---|---|
| TLR2 | CD4 | 0.00055 | 91% | 98% | 0.758 | 1.2E−04 |
| TLR2 | PTGS2 | 0.00100 | 77% | 99% | 0.704 | 8.5E−06 |
| TLR2 | IL18BP | 0.00019 | 77% | 99% | 0.680 | 1.8E−05 |
| TLR2 | HSPA1A | 0.00160 | 82% | 99% | 0.685 | 2.9E−05 |
| TLR2 | HMGB1 | 0.00140 | 77% | 99% | 0.706 | 3.2E−06 |
| TLR2 | C1QA | 0.00077 | 100% | 96% | 0.630 | 4.6E−06 |
| TLR2 | MNDA | 0.00180 | 82% | 99% | 0.673 | 8.1E−07 |
| TLR2 | CD19 | 0.00500 | 86% | 96% | 0.636 | 2.2E−05 |
| TLR2 | CD86 | 0.00850 | 77% | 99% | 0.649 | 5.4E−06 |
| TLR2 | SERPING1 | 0.00570 | 73% | 99% | 0.623 | 2.4E−05 |
| TLR2 | CD8A | 0.00740 | 73% | 99% | 0.623 | 2.1E−06 |
| TLR2 | PTPRC | 0.01500 | 77% | 97% | 0.601 | 4.0E−06 |
| TLR2 | MYC | 0.01400 | 77% | 98% | 0.603 | 2.0E−05 |
| MMP9 | SERPING1 | 0.00025 | 82% | 97% | 0.632 | 0.00001 |
| MMP9 | PTGS2 | 0.00062 | 82% | 98% | 0.648 | 5.5E−07 |
| MMP9 | IFI16 | 0.00075 | 77% | 97% | 0.602 | 0.00035 |
| MMP9 | HSPA1A | 0.00130 | 73% | 97% | 0.615 | 4.5E−07 |
| IFI16 | HMGB1 | 0.00017 | 86% | 97% | 0.650 | 3.90E−06 |
| IFI16 | SERPINE1 | 0.00013 | 77% | 99% | 0.628 | 5.50E−06 |
| IFI16 | CD19 | 0.00053 | 77% | 98% | 0.618 | 4.10E−06 |
| TGFB1 | CD4 | 5.30E−05 | 91% | 97% | 0.728 | 3.80E−06 |
| TGFB1 | IL18BP | 0.00011 | 68% | 99% | 0.628 | 2.10E−06 |
| TGFB1 | PTGS2 | 9.80E−05 | 73% | 99% | 0.621 | 1.20E−06 |
| NFKB1 | CD4 | 0.00024 | 82% | 100% | 0.789 | 2.60E−05 |
| NFKB1 | IL18BP | 0.00015 | 82% | 99% | 0.746 | 2.20E−05 |
| TIMP1 | CD4 | 7.30E−05 | 82% | 97% | 0.679 | 5.00E−06 |

TABLE 6

Latent class modeling-estimating RA v. Normal discrimination in a dataset using a 3-gene model (RA, N = 22, Normal N = 134)

| gene 1 | gene 2 | gene 3 | Gene 3 Inc. P-Value | % RA | % normal | R-SQ | Gene 1 Inc. P-Value | Gene 2 Inc. P-Value | Gene 3 Inc. p-value Latent Gold |
|---|---|---|---|---|---|---|---|---|---|
| TLR2 | CD4 | NFKB1 | 0.0230 | 100% | 100% | 0.993 | 0.0320 | 0.0110 | |
| TLR2 | CD4 | MYC | 0.0370 | 96% | 99% | 0.933 | 0.0110 | 0.0120 | |
| TLR2 | CD4 | TNFSF5 | 0.0170 | 96% | 99% | 0.891 | 0.0020 | 0.0045 | |
| TLR2 | CD4 | LTA | 0.0110 | 91% | 100% | 0.860 | 0.0024 | 0.0028 | |
| TLR2 | CD4 | TGFB1 | 0.0079 | 91% | 99% | 0.846 | 0.0210 | 7.6E−04 | |
| TLR2 | CD4 | C1QA | 0.0140 | 96% | 99% | 0.831 | 1.7E−04 | 0.0021 | |
| TLR2 | CD4 | DPP4 | 0.0220 | 91% | 99% | 0.821 | 9.3E−04 | 0.0020 | |
| TLR2 | CD4 | HMGB1 | 0.0180 | 82% | 100% | 0.817 | 0.0010 | 0.0050 | |
| TLR2 | CD4 | EGR1 | 0.0020 | 82% | 100% | 0.812 | 0.0042 | 0.0098 | |
| TLR2 | CD4 | IL1R1 | 0.0370 | 86% | 99% | 0.786 | 0.0010 | 0.0065 | |
| TLR2 | CD4 | SERPINE1 | 0.0370 | 77% | 100% | 0.798 | 9.3E−04 | 0.0012 | |
| TLR2 | PTGS2 | NFKB1 | 0.0088 | 91% | 99% | 0.830 | 8.6E−04 | 0.0230 | |
| TLR2 | PTGS2 | IL1R1 | 0.0210 | 86% | 99% | 0.771 | 2.0E−04 | 0.0010 | |

TABLE 6-continued

Latent class modeling-estimating RA v. Normal
discrimination in a dataset using a 3-gene model (RA, N = 22, Normal N = 134)

| gene 1 | gene 2 | gene 3 | | % RA | % normal | LG Analysis R-SQ | Gene 1 Inc. P-Value | Gene 2 Inc. P-Value | Gene 3 Inc. p-value Latent Gold |
|---|---|---|---|---|---|---|---|---|---|
| TLR2 | PTGS2 | C1QA | 0.0045 | 91% | 99% | 0.835 | 6.2E−04 | 0.0059 | |
| TLR2 | PTGS2 | MYC | 0.0110 | 82% | 100% | 0.788 | 2.3E−04 | 0.0017 | |
| TLR2 | PTGS2 | TGFB1 | 0.0110 | 91% | 99% | 0.814 | 0.0036 | 0.0015 | |
| TLR2 | PTGS2 | ICAM1 | 0.0360 | 86% | 100% | 0.741 | 5.3E−05 | 4.7E−04 | |
| TLR2 | PTGS2 | HMGB1 | 0.0130 | 86% | 99% | 0.778 | 7.1E−05 | 0.0085 | |
| TLR2 | PTGS2 | IL1RN | 0.0250 | 77% | 99% | 0.770 | 6.5E−05 | 9.3E−04 | |
| TLR2 | PTGS2 | SERPINE1 | 0.0450 | 82% | 99% | 0.739 | 9.7E−05 | 0.0020 | |
| TLR2 | PTGS2 | LTA | 0.0420 | 91% | 98% | 0.760 | 4.6E−05 | 8.6E−04 | |
| TLR2 | PTGS2 | TIMP1 | 0.0320 | 77% | 99% | 0.749 | 4.0E−04 | 0.0013 | |
| TLR2 | PTGS2 | IFI16 | 0.0470 | 73% | 100% | 0.752 | 6.0E−04 | 0.0024 | |
| TLR2 | PTGS2 | IL18BP | 0.0290 | 82% | 99% | 0.749 | 3.8E−05 | 0.0140 | |
| TLR2 | PTGS2 | CD19 | 0.0420 | 82% | 99% | 0.741 | 5.3E−05 | 0.0056 | |
| TLR2 | IL18BP | MYC | 0.0058 | 82% | 100% | 0.811 | 0.0024 | 0.0012 | |
| TLR2 | IL18BP | NFKB1 | 0.0062 | 96% | 99% | 0.802 | 0.0250 | 8.8E−04 | |
| TLR2 | IL18BP | C1QA | 0.0058 | 96% | 98% | 0.783 | 5.8E−05 | 0.0012 | |
| TLR2 | IL18BP | HMGB1 | 0.0076 | 86% | 99% | 0.779 | 1.0E−04 | 0.0020 | |
| TLR2 | IL18BP | TNFSF5 | 0.0130 | 86% | 99% | 0.754 | 1.3E−04 | 2.0E−04 | |
| TLR2 | IL18BP | HSPA1A | 0.0130 | 82% | 99% | 0.763 | 2.1E−04 | 0.0100 | |
| TLR2 | IL18BP | SERPING1 | 0.0260 | 82% | 99% | 0.759 | 1.9E−04 | 0.0092 | |
| TLR2 | IL18BP | IL1R1 | 0.0250 | 82% | 98% | 0.723 | 5.0E−04 | 1.9E−04 | |
| TLR2 | IL18BP | LTA | 0.0250 | 77% | 99% | 0.714 | 1.3E−04 | 2.1E−04 | |
| TLR2 | IL18BP | IFI16 | 0.0310 | 86% | 99% | 0.759 | 0.0027 | 4.8E−04 | |
| TLR2 | IL18BP | TGFB1 | 0.0310 | 77% | 99% | 0.714 | 0.0030 | 5.9E−04 | |
| TLR2 | IL18BP | SERPINE1 | 0.0340 | 91% | 97% | 0.711 | 2.1E−04 | 4.5E−04 | |
| TLR2 | IL18BP | MNDA | 0.0360 | 91% | 98% | 0.736 | 5.7E−06 | 0.0029 | |
| TLR2 | HSPA1A | NFKB1 | 0.0065 | 82% | 99% | 0.772 | 4.9E−04 | 2.8E−04 | |
| TLR2 | HSPA1A | ICAM1 | 0.0150 | 86% | 99% | 0.760 | 1.2E−04 | 0.0043 | |
| TLR2 | HSPA1A | MMP9 | 0.0120 | 82% | 99% | 0.778 | 0.0024 | 5.8E−04 | |
| TLR2 | HSPA1A | C1QA | 0.0042 | 100% | 98% | 0.790 | 1.1E−04 | 0.0057 | |
| TLR2 | HSPA1A | TNFSF6 | 0.0150 | 91% | 98% | 0.745 | 5.7E−05 | 0.0020 | |
| TLR2 | HSPA1A | IL1R1 | 0.0066 | 82% | 99% | 0.744 | 1.5E−04 | 6.8E−04 | |
| TLR2 | HSPA1A | EGR1 | 0.0093 | 96% | 99% | 0.787 | 5.6E−04 | 5.8E−04 | |
| TLR2 | HSPA1A | IL1B | 0.0150 | 91% | 97% | 0.748 | 1.0E−04 | 5.3E−04 | |
| TLR2 | HSPA1A | IL1RN | 0.0220 | 82% | 99% | 0.743 | 1.0E−04 | 4.3E−04 | |
| TLR2 | HSPA1A | MYC | 0.0210 | 82% | 99% | 0.739 | 1.6E−04 | 8.0E−04 | |
| TLR2 | HSPA1A | IFI16 | 0.0130 | 96% | 97% | 0.732 | 7.1E−04 | 0.0030 | |
| TLR2 | HSPA1A | TGFB1 | 0.0160 | 82% | 99% | 0.762 | 6.1E−04 | 4.5E−04 | |
| TLR2 | HSPA1A | CD19 | 0.0210 | 91% | 99% | 0.780 | 1.2E−04 | 0.0045 | |
| TLR2 | HSPA1A | SERPINE1 | 0.0100 | 86% | 99% | 0.755 | 2.6E−04 | 0.0014 | |
| TLR2 | HSPA1A | TIMP1 | 0.0190 | 82% | 99% | 0.734 | 3.1E−04 | 6.7E−04 | |
| TLR2 | HSPA1A | HMGB1 | 0.0180 | 91% | 99% | 0.783 | 2.4E−04 | 0.0200 | |
| TLR2 | HSPA1A | SERPING1 | 0.0260 | 86% | 98% | 0.722 | 2.4E−04 | 0.0060 | |
| TLR2 | HSPA1A | MPO | 0.0330 | 77% | 99% | 0.724 | 1.2E−04 | 0.0018 | |
| TLR2 | HMGB1 | C1QA | 0.0061 | 91% | 99% | 0.794 | 2.6E−05 | 0.0054 | |
| TLR2 | HMGB1 | IFI16 | 0.0083 | 77% | 99% | 0.741 | 0.0130 | 0.0016 | |
| TLR2 | HMGB1 | TNFSF6 | 0.0130 | 86% | 99% | 0.764 | 1.8E−05 | 0.0023 | |
| TLR2 | HMGB1 | CD8A | 0.0370 | 86% | 99% | 0.766 | 1.2E−05 | 0.0032 | |
| TLR2 | HMGB1 | GCLC | 0.0290 | 96% | 98% | 0.734 | 1.6E−05 | 7.5E−04 | |
| TLR2 | HMGB1 | IL1R1 | 0.0470 | 96% | 96% | 0.730 | 6.2E−04 | 0.0012 | |
| TLR2 | C1QA | CD4 | 0.0021 | 96% | 99% | 0.831 | 1.7E−04 | 0.0140 | |
| TLR2 | C1QA | HSPA1A | 0.0057 | 100% | 98% | 0.790 | 1.1E−04 | 0.0042 | |
| TLR2 | C1QA | CD19 | 0.0070 | 96% | 98% | 0.786 | 4.6E−05 | 0.0015 | |
| TLR2 | C1QA | HMGB1 | 0.0054 | 91% | 99% | 0.794 | 2.6E−05 | 0.0061 | |
| TLR2 | C1QA | APAF1 | 0.0097 | 86% | 98% | 0.736 | 1.8E−04 | 0.0019 | |
| TLR2 | C1QA | CD8A | 0.0230 | 96% | 97% | 0.715 | 1.3E−04 | 0.0025 | |
| TLR2 | MNDA | SERPING1 | 0.0180 | 82% | 99% | 0.724 | 4.8E−05 | 0.0057 | |
| TLR2 | MNDA | CD19 | 0.0220 | 91% | 99% | 0.767 | 4.8E−06 | 0.0093 | |
| TLR2 | MNDA | C1QA | 0.0120 | 86% | 98% | 0.704 | 3.9E−06 | 0.0310 | |
| TLR2 | MNDA | NFKB1 | 0.0270 | 91% | 98% | 0.716 | 8.0E−05 | 0.0007 | |
| TLR2 | MNDA | SERPINE1 | 0.0240 | 86% | 99% | 0.729 | 6.3E−06 | 0.0017 | |
| TLR2 | MNDA | IFI16 | 0.0290 | 86% | 98% | 0.688 | 3.7E−04 | 0.0026 | |
| TLR2 | MNDA | CD8A | 0.0430 | 86% | 98% | 0.706 | 7.2E−06 | 0.0079 | |
| TLR2 | MNDA | MYC | 0.0450 | 82% | 99% | 0.709 | 1.6E−05 | 0.0045 | |
| TLR2 | MNDA | IL1R1 | 0.0280 | 86% | 98% | 0.699 | 1.8E−05 | 8.1E−04 | |
| TLR2 | MNDA | MMP9 | 0.0440 | 91% | 97% | 0.707 | 0.0012 | 0.0011 | |
| TLR2 | CD19 | IFI16 | 0.0069 | 86% | 99% | 0.734 | 0.0054 | 0.0020 | |
| TLR2 | CD19 | SERPING1 | 0.0130 | 86% | 99% | 0.740 | 0.0019 | 0.0069 | |
| TLR2 | CD19 | MYC | 0.0130 | 82% | 99% | 0.724 | 0.0015 | 0.0050 | |
| TLR2 | CD19 | CD86 | 0.0420 | 91% | 98% | 0.707 | 1.6E−05 | 0.0280 | |
| TLR2 | CD19 | APAF1 | 0.0400 | 82% | 98% | 0.677 | 1.4E−04 | 0.0220 | |
| TLR2 | CD19 | NFKB1 | 0.0360 | 96% | 96% | 0.673 | 0.0050 | 0.0036 | |
| TLR2 | CD86 | MYC | 0.0140 | 86% | 99% | 0.746 | 2.1E−04 | 0.0100 | |

TABLE 6-continued

Latent class modeling-estimating RA v. Normal discrimination in a dataset using a 3-gene model (RA, N = 22, Normal N = 134)

| gene 1 | gene 2 | gene 3 | | % RA | % normal | R-SQ | LG Analysis Gene 1 Inc. P-Value | Gene 2 Inc. P-Value | Gene 3 Inc. p-value Latent Gold |
|---|---|---|---|---|---|---|---|---|---|
| TLR2 | CD86 | NFKB1 | 0.0210 | 91% | 99% | 0.722 | 0.0010 | 0.0035 | |
| TLR2 | CD86 | SERPING1 | 0.0190 | 91% | 97% | 0.697 | 8.0E−05 | 0.0260 | |
| TLR2 | CD86 | SERPINE1 | 0.0150 | 86% | 99% | 0.712 | 5.3E−05 | 0.0043 | |
| TLR2 | CD86 | MPO | 0.0390 | 86% | 98% | 0.671 | 6.1E−05 | 0.0053 | |
| TLR2 | CD86 | IFI16 | 0.0440 | 77% | 98% | 0.654 | 0.0010 | 0.0160 | |
| TLR2 | CD86 | TIMP1 | 0.0290 | 86% | 98% | 0.703 | 0.0010 | 0.0018 | |
| TLR2 | SERPING1 | C1QA | 0.0016 | 100% | 96% | 0.717 | 1.3E−04 | 0.0092 | |
| TLR2 | SERPING1 | IL15 | 0.0200 | 82% | 97% | 0.669 | 4.8E−05 | 0.0084 | |
| TLR2 | SERPING1 | MYC | 0.0170 | 86% | 98% | 0.689 | 5.0E−04 | 0.0084 | |
| TLR2 | SERPING1 | APAF1 | 0.0270 | 77% | 99% | 0.664 | 0.0020 | 0.0200 | |
| TLR2 | SERPING1 | TNFSF6 | 0.0170 | 77% | 99% | 0.660 | 5.3E−05 | 0.0096 | |
| TLR2 | SERPING1 | SERPINE1 | 0.0230 | 82% | 99% | 0.665 | 4.0E−04 | 0.0045 | |
| TLR2 | SERPING1 | IL1R1 | 0.0460 | 73% | 99% | 0.638 | 0.0028 | 0.0033 | |
| TLR2 | SERPING1 | PTPRC | 0.0400 | 77% | 99% | 0.669 | 4.7E−05 | 0.0160 | |
| TLR2 | CD8A | MYC | 0.0100 | 91% | 98% | 0.730 | 0.0001 | 0.0061 | |
| TLR2 | CD8A | APAF1 | 0.0250 | 82% | 98% | 0.651 | 0.0002 | 0.0300 | |
| TLR2 | CD8A | NFKB1 | 0.0290 | 73% | 99% | 0.686 | 0.0016 | 0.0028 | |
| TLR2 | PTPRC | NFKB1 | 0.0018 | 100% | 97% | 0.755 | 0.0014 | 0.0010 | |
| TLR2 | PTPRC | MYC | 0.0020 | 82% | 99% | 0.758 | 2.4E−05 | 0.0035 | |
| TLR2 | PTPRC | C1QA | 0.0020 | 100% | 97% | 0.365 | 1.6E−05 | 0.0410 | |
| TLR2 | PTPRC | IFI16 | 0.0160 | 73% | 99% | 0.657 | 5.4E−05 | 0.0120 | |
| TLR2 | PTPRC | TNFSF6 | 0.0220 | 82% | 97% | 0.632 | 7.2E−06 | 0.0290 | |
| TLR2 | PTPRC | TNFSF5 | 0.0330 | 77% | 99% | 0.669 | 1.1E−05 | 0.0028 | |
| TLR2 | MYC | APAF1 | 0.0062 | 86% | 97% | 0.683 | 8.9E−05 | 0.0140 | |
| TLR2 | MYC | C1QA | 0.0022 | 86% | 98% | 0.691 | 1.4E−04 | 0.0370 | |
| TLR2 | MYC | CD8A | 0.0061 | 91% | 98% | 0.730 | 1.1E−04 | 0.0100 | |
| TLR2 | MYC | DPP4 | 0.0140 | 77% | 98% | 0.676 | 7.9E−04 | 0.0020 | |
| TLR2 | MYC | PLA2G7 | 0.0170 | 86% | 99% | 0.677 | 3.8E−04 | 0.0046 | |
| TLR2 | MYC | IFI16 | 0.0170 | 73% | 99% | 0.635 | 0.0110 | 0.0130 | |
| TLR2 | MYC | CYBB | 0.0270 | 86% | 98% | 0.660 | 1.9E−04 | 0.0073 | |
| TLR2 | MYC | CD14 | 0.0280 | 82% | 98% | 0.660 | 9.5E−05 | 0.0096 | |
| TLR2 | MYC | SERPINE1 | 0.0490 | 73% | 98% | 0.622 | 1.1E−04 | 0.0170 | |
| MMP9 | SERPING1 | HSPA1A | 0.0011 | 91% | 99% | 0.821 | 2.0E−04 | 6.0E−04 | |
| MMP9 | SERPING1 | PTGS2 | 0.0029 | 96% | 98% | 0.789 | 7.4E−05 | 8.2E−04 | |
| MMP9 | SERPING1 | CD4 | 0.0026 | 77% | 100% | 0.757 | 3.6E−05 | 6.9E−04 | |
| MMP9 | SERPING1 | C1QA | 0.0069 | 100% | 97% | 0.713 | 7.5E−05 | 2.9E−04 | |
| MMP9 | SERPING1 | MNDA | 0.0066 | 91% | 98% | 0.713 | 1.1E−05 | 2.4E−04 | |
| MMP9 | SERPING1 | IL18BP | 0.0081 | 86% | 99% | 0.721 | 7.7E−05 | 2.8E−04 | |
| MMP9 | SERPING1 | IL1R1 | 0.0200 | 73% | 99% | 0.665 | 0.0010 | 3.4E−04 | |
| MMP9 | SERPING1 | MYC | 0.0280 | 86% | 98% | 0.676 | 2.2E−04 | 7.5E−04 | |
| MMP9 | SERPING1 | APAF1 | 0.0340 | 82% | 98% | 0.679 | 8.2E−05 | 6.1E−04 | |
| MMP9 | SERPING1 | CD86 | 0.0290 | 86% | 97% | 0.678 | 5.5E−05 | 3.7E−04 | |
| MMP9 | SERPING1 | CD19 | 0.0400 | 82% | 99% | 0.682 | 6.5E−05 | 1.9E−04 | |
| MMP9 | SERPING1 | SERPINE1 | 0.0250 | 82% | 99% | 0.678 | 1.8E−04 | 2.0E−04 | |
| MMP9 | SERPING1 | HMGB1 | 0.0330 | 86% | 99% | 0.684 | 5.5E−05 | 7.5E−04 | |
| MMP9 | SERPING1 | MPO | 0.0340 | 91% | 97% | 0.669 | 1.5E−04 | 3.1E−04 | |
| MMP9 | PTGS2 | NFKB1 | 0.0020 | 96% | 99% | 0.801 | 4.1E−04 | 8.6E−04 | |
| MMP9 | PTGS2 | MYC | 0.0023 | 82% | 99% | 0.756 | 6.2E−05 | 7.9E−04 | |
| MMP9 | PTGS2 | TGFB1 | 0.0023 | 82% | 99% | 0.757 | 0.0019 | 8.4E−04 | |
| MMP9 | PTGS2 | IL1R1 | 0.0039 | 82% | 99% | 0.741 | 5.8E−04 | 3.5E−04 | |
| MMP9 | PTGS2 | IFI16 | 0.0019 | 82% | 99% | 0.754 | 1.4E−04 | 0.0029 | |
| MMP9 | PTGS2 | MPO | 0.0079 | 91% | 96% | 0.684 | 6.1E−06 | 5.9E−04 | |
| MMP9 | PTGS2 | EGR1 | 0.0110 | 77% | 99% | 0.677 | 1.4E−05 | 0.0011 | |
| MMP9 | PTGS2 | PLAUR | 0.0230 | 77% | 99% | 0.701 | 3.0E−04 | 1.5E−04 | |
| MMP9 | PTGS2 | C1QA | 0.0081 | 86% | 98% | 0.708 | 2.1E−06 | 0.0014 | |
| MMP9 | PTGS2 | TNFSF5 | 0.0450 | 77% | 99% | 0.716 | 1.5E−06 | 3.9E−04 | |
| MMP9 | PTGS2 | SERPINA1 | 0.0400 | 86% | 99% | 0.696 | 3.4E−04 | 2.2E−04 | |
| MMP9 | PTGS2 | LTA | 0.0210 | 82% | 99% | 0.695 | 1.1E−06 | 4.2E−04 | |
| MMP9 | PTGS2 | TIMP1 | 0.0170 | 77% | 99% | 0.696 | 1.3E−04 | 4.8E−04 | |
| MMP9 | PTGS2 | ICAM1 | 0.0430 | 86% | 99% | 0.693 | 2.0E−06 | 2.2E−04 | |
| MMP9 | PTGS2 | TNF | 0.0430 | 77% | 99% | 0.702 | 3.6E−06 | 8.3E−04 | |
| MMP9 | PTGS2 | SERPINE1 | 0.0300 | 82% | 99% | 0.680 | 9.8E−06 | 0.0012 | |
| MMP9 | HSPA1A | IFI16 | 0.0001 | 86% | 99% | 0.808 | 2.5E−04 | 5.3E−04 | |
| MMP9 | HSPA1A | TLR2 | 0.0024 | 82% | 99% | 0.778 | 0.0120 | 5.8E−04 | |
| MMP9 | HSPA1A | NFKB1 | 0.0009 | 86% | 99% | 0.763 | 3.7E−05 | 2.6E−05 | |
| MMP9 | HSPA1A | EGR1 | 0.0015 | 86% | 99% | 0.760 | 5.2E−05 | 3.9E−04 | |
| MMP9 | HSPA1A | MYC | 0.0031 | 86% | 99% | 0.723 | 9.6E−05 | 1.8E−04 | |
| MMP9 | HSPA1A | IL1R1 | 0.0016 | 77% | 98% | 0.683 | 1.6E−05 | 6.4E−04 | |
| MMP9 | HSPA1A | IL1B | 0.0045 | 77% | 99% | 0.701 | 1.3E−05 | 2.2E−04 | |
| MMP9 | HSPA1A | SERPINA1 | 0.0110 | 73% | 99% | 0.686 | 2.1E−05 | 5.3E−05 | |
| MMP9 | HSPA1A | MPO | 0.0035 | 82% | 98% | 0.675 | 2.8E−06 | 7.3E−04 | |
| MMP9 | HSPA1A | PTGS2 | 0.0056 | 87% | 99% | 0.704 | 6.9E−06 | 0.0290 | |

TABLE 6-continued

Latent class modeling-estimating RA v. Normal discrimination in a dataset using a 3-gene model (RA, N = 22, Normal N = 134)

| | | | | | | LG Analysis | | | Gene 3 Inc. p-value Latent Gold |
|---|---|---|---|---|---|---|---|---|---|
| gene 1 | gene 2 | gene 3 | | % RA | % normal | R-SQ | Gene 1 Inc. P-Value | Gene 2 Inc. P-Value | |
| MMP9 | HSPA1A | ICAM1 | 0.0260 | 82% | 99% | 0.681 | 8.8E−07 | 1.2E−04 | |
| MMP9 | HSPA1A | TGFB1 | 0.0100 | 82% | 99% | 0.684 | 2.8E−04 | 1.6E−04 | |
| MMP9 | HSPA1A | C1QA | 0.0093 | 86% | 99% | 0.695 | 1.5E−06 | 0.0079 | |
| MMP9 | HSPA1A | SERPINE1 | 0.0090 | 77% | 99% | 0.690 | 4.3E−06 | 8.2E−04 | |
| MMP9 | HSPA1A | TIMP1 | 0.0190 | 73% | 99% | 0.695 | 5.9E−06 | 2.0E−04 | |
| MMP9 | HSPA1A | IL1RN | 0.0400 | 68% | 100% | 0.656 | 6.0E−06 | 3.5E−04 | |
| MMP9 | HSPA1A | IL18 | 0.0470 | 68% | 100% | 0.644 | 1.5E−06 | 5.8E−04 | |
| MMP9 | IFI16 | HMGB1 | 0.0027 | 96% | 99% | 0.746 | 0.0056 | 5.1E−04 | |
| MMP9 | IFI16 | CD4 | 0.0026 | 91% | 99% | 0.761 | 3.0E−04 | 7.4E−04 | |
| MMP9 | IFI16 | MNDA | 0.0040 | 77% | 99% | 0.702 | 1.0E−04 | 2.8E−04 | |
| MMP9 | IFI16 | APAF1 | 0.0058 | 77% | 100% | 0.752 | 1.2E−04 | 0.0034 | |
| MMP9 | IFI16 | IL18BP | 0.0053 | 91% | 99% | 0.734 | 0.0019 | 0.0048 | |
| MMP9 | IFI16 | CD19 | 0.0068 | 77% | 99% | 0.707 | 0.0043 | 0.0026 | |
| MMP9 | IFI16 | C1QA | 0.0055 | 68% | 99% | 0.668 | 0.0006 | 0.0019 | |
| MMP9 | IFI16 | CD86 | 0.0130 | 82% | 97% | 0.656 | 2.1E−04 | 4.6E−04 | |
| MMP9 | IFI16 | SERPINE1 | 0.0095 | 73% | 99% | 0.672 | 0.0230 | 6.2E−04 | |
| MMP9 | IFI16 | MYC | 0.0180 | 73% | 98% | 0.644 | 0.0039 | 0.0022 | |
| MMP9 | IFI16 | ADAM17 | 0.0200 | 73% | 100% | 0.676 | 1.5E−04 | 3.2E−04 | |
| MMP9 | IFI16 | PTPRC | 0.0220 | 77% | 99% | 0.685 | 6.5E−05 | 3.1E−04 | |
| MMP9 | IFI16 | CD14 | 0.0170 | 73% | 99% | 0.680 | 1.8E−04 | 3.1E−04 | |
| MMP9 | IFI16 | HMOX1 | 0.0320 | 86% | 97% | 0.659 | 2.2E−04 | 0.0004 | |
| MMP9 | IFI16 | MPO | 0.0330 | 73% | 99% | 0.626 | 0.0053 | 9.0E−04 | |
| MMP9 | IFI16 | CD8A | 0.0400 | 73% | 98% | 0.647 | 2.7E−04 | 2.4E−03 | |
| MMP9 | IFI16 | PLAUR | 0.0490 | 82% | 99% | 0.683 | 1.5E−04 | 4.5E−04 | |
| IFI16 | HMGB1 | IL1R1 | 0.0042 | 91% | 98% | 0.775 | 3.5E−04 | 2.8E−04 | |
| IFI16 | HMGB1 | NFKB1 | 0.0066 | 91% | 99% | 0.777 | 6.3E−04 | 3.9E−04 | |
| IFI16 | HMGB1 | MPO | 0.0096 | 77% | 99% | 0.729 | 8.8E−05 | 5.5E−04 | |
| IFI16 | HMGB1 | MYC | 0.0160 | 100% | 97% | 0.740 | 6.3E−05 | 9.1E−04 | |
| IFI16 | HMGB1 | TIMP1 | 0.0077 | 96% | 96% | 0.727 | 1.5E−04 | 0.0010 | |
| IFI16 | HMGB1 | IL18BP | 0.0100 | 77% | 99% | 0.736 | 1.8E−04 | 0.0015 | |
| IFI16 | HMGB1 | SERPINE1 | 0.0095 | 96% | 96% | 0.721 | 2.0E−05 | 0.0036 | |
| IFI16 | HMGB1 | CD19 | 0.0120 | 86% | 98% | 0.714 | 1.8E−05 | 0.0016 | |
| IFI16 | HMGB1 | ELA2 | 0.0280 | 82% | 99% | 0.702 | 1.4E−05 | 1.3E−04 | |
| IFI16 | HMGB1 | TGFB1 | 0.0220 | 82% | 98% | 0.707 | 1.8E−04 | 0.0015 | |
| IFI16 | HMGB1 | IL10 | 0.0240 | 73% | 99% | 0.702 | 3.9E−05 | 3.6E−04 | |
| IFI16 | HMGB1 | C1QA | 0.0280 | 77% | 99% | 0.725 | 8.8E−06 | 6.1E−04 | |
| IFI16 | HMGB1 | PTGS2 | 0.0270 | 82% | 99% | 0.721 | 1.1E−05 | 4.0E−04 | |
| IFI16 | HMGB1 | ADAM17 | 0.0430 | 77% | 99% | 0.683 | 1.4E−04 | 4.8E−05 | |
| IFI16 | HMGB1 | IL18 | 0.0041 | 77% | 99% | 0.725 | 6.8E−05 | 2.2E−04 | |
| IFI16 | SERPINE1 | C1QA | 0.0022 | 86% | 99% | 0.757 | 2.1E−04 | 3.9E−04 | |
| IFI16 | SERPINE1 | PTGS2 | 0.0039 | 82% | 100% | 0.798 | 1.2E−05 | 4.1E−05 | |
| IFI16 | SERPINE1 | IL18BP | 0.0009 | 86% | 98% | 0.771 | 2.7E−05 | 0.0012 | |
| IFI16 | SERPINE1 | CD4 | 0.0041 | 91% | 98% | 0.768 | 4.4E−05 | 7.3E−05 | |
| IFI16 | SERPINE1 | HMOX1 | 0.0047 | 86% | 98% | 0.731 | 9.0E−06 | 1.1E−04 | |
| IFI16 | SERPINE1 | CD86 | 0.0088 | 77% | 99% | 0.693 | 1.7E−05 | 1.0E−04 | |
| IFI16 | SERPINE1 | MYC | 0.0130 | 77% | 99% | 0.675 | 6.2E−05 | 0.0024 | |
| IFI16 | SERPINE1 | HSPA1A | 0.0060 | 73% | 99% | 0.711 | 7.5E−06 | 6.6E−05 | |
| IFI16 | SERPINE1 | CD19 | 0.0230 | 73% | 100% | 0.686 | 1.5E−05 | 0.0082 | |
| IFI16 | SERPINE1 | MNDA | 0.0330 | 82% | 97% | 0.666 | 2.5E−06 | 7.8E−05 | |
| IFI16 | SERPINE1 | TLR2 | 0.0390 | 73% | 99% | 0.663 | 0.0036 | 0.0062 | |
| IFI16 | SERPINE1 | MMP9 | 0.0230 | 73% | 99% | 0.672 | 0.0006 | 0.0095 | |
| | | | GoldMine | | | | | | |
| IFI16 | CD19 | NFKB1 | 1.4E−04 | 82% | 99% | 0.718 | 4.9E−04 | 0.0013 | 0.0023 |
| IFI16 | CD19 | MYC | 1.7E−04 | 82% | 99% | 0.718 | 1.6E−04 | 0.0018 | 0.0037 |
| IFI16 | CD19 | MMP9 | 6.4E−04 | 77% | 99% | 0.707 | 2.6E−04 | 0.0068 | 0.0043 |
| IFI16 | CD19 | C1QA | 1.0E−03 | 82% | 96% | 0.670 | 1.4E−05 | 0.0009 | 0.0034 |
| TGFB1 | CD4 | NFKB1 | 3.0E−05 | 86% | 100% | 0.855 | 0.0230 | 0.0017 | 0.0078 |
| TGFB1 | CD4 | TLR2 | 1.1E−04 | 91% | 99% | 0.846 | 0.0079 | 7.6E−04 | 0.021 |
| TGFB1 | CD4 | IFI16 | 1.9E−04 | 91% | 99% | 0.823 | 0.0004 | 0.0028 | 0.0064 |
| TGFB1 | CD4 | IL1R1 | 2.4E−04 | 100% | 97% | 0.821 | 3.0E−04 | 8.3E−04 | 0.0028 |
| TGFB1 | CD4 | IL10 | 3.6E−04 | 96% | 99% | 0.842 | 1.2E−04 | 7.2E−04 | 0.0099 |
| TGFB1 | CD4 | SERPINA1 | 8.4E−04 | 86% | 99% | 0.800 | 3.1E−04 | 6.3E−04 | 0.014 |
| TGFB1 | IL18BP | IFI16 | 8.6E−06 | 73% | 100% | 0.740 | 0.0014 | 0.0016 | 0.00072 |
| TGFB1 | IL18BP | SERPING1 | 2.9E−05 | 86% | 99% | 0.722 | 2.4E−04 | 0.0019 | 0.0021 |
| TGFB1 | IL18BP | TLR2 | 6.4E−05 | 77% | 99% | 0.714 | 0.0310 | 5.9E−04 | 0.003 |
| TGFB1 | IL18BP | PTGS2 | 1.9E−04 | 86% | 99% | 0.754 | 8.7E−06 | 0.0023 | 0.0024 |
| TGFB1 | IL18BP | IL1R1 | 2.0E−04 | 82% | 99% | 0.727 | 8.5E−04 | 4.9E−04 | 0.0044 |
| TGFB1 | PTGS2 | IL1R1 | 1.0E−07 | 86% | 99% | 0.760 | 5.3E−04 | 6.5E−04 | 0.0025 |
| TGFB1 | PTGS2 | IFI16 | 1.2E−07 | 77% | 100% | 0.806 | 0.0027 | 0.0021 | 0.0019 |
| TGFB1 | PTGS2 | TLR2 | 6.5E−07 | 91% | 99% | 0.814 | 0.0110 | 0.0015 | 0.0036 |
| TGFB1 | PTGS2 | CD4 | 1.8E−06 | 91% | 99% | 0.814 | 1.7E−05 | 0.0170 | 0.0016 |

TABLE 6-continued

Latent class modeling-estimating RA v. Normal discrimination in a dataset using a 3-gene model (RA, N = 22, Normal N = 134)

| gene 1 | gene 2 | gene 3 | | % RA | % normal | R-SQ | LG Analysis Gene 1 Inc. P-Value | Gene 2 Inc. P-Value | Gene 3 Inc. p-value Latent Gold |
|---|---|---|---|---|---|---|---|---|---|
| TGFB1 | PTGS2 | SERPINA1 | 2.1E−06 | 96% | 99% | 0.775 | 4.5E−04 | 0.0010 | 0.0034 |
| TGFB1 | PTGS2 | MMP9 | 4.2E−06 | 82% | 99% | 0.757 | 0.0023 | 8.4E−04 | 0.0019 |
| TGFB1 | PTGS2 | SERPING1 | 4.0E−05 | 82% | 99% | 0.739 | 2.6E−04 | 0.0010 | 0.002 |
| TGFB1 | PTGS2 | IL18BP | 1.2E−04 | 86% | 99% | 0.754 | 8.7E−06 | 0.0024 | 0.0023 |
| TGFB1 | PTGS2 | IL1B | 1.5E−04 | 73% | 100% | 0.723 | 7.7E−05 | 9.7E−05 | 0.0028 |
| TGFB1 | PTGS2 | NFKB1 | 1.8E−04 | 82% | 99% | 0.711 | 0.0011 | 0.0041 | 0.0037 |
| NFKB1 | CD4 | TLR2 | 1.7E−06 | 100% | 100% | 0.993 | 0.0230 | 0.0110 | 0.032 |
| NFKB1 | CD4 | MMP9 | 3.9E−05 | 96% | 100% | 0.941 | 0.0190 | 0.0110 | 0.021 |
| NFKB1 | CD4 | IL10 | 6.5E−05 | 96% | 100% | 0.917 | 0.0090 | 0.0080 | 0.016 |
| NFKB1 | CD4 | IFI16 | 1.1E−04 | 96% | 99% | 0.906 | 0.0013 | 0.0022 | 0.0075 |
| NFKB1 | CD4 | TIMP1 | 4.7E−04 | 96% | 99% | 0.876 | 0.0038 | 0.0015 | 0.0091 |
| NFKB1 | CD4 | CD14 | 9.1E−04 | 96% | 99% | 0.852 | 8.6E−04 | 8.6E−04 | 0.018 |
| NFKB1 | CD4 | IL1R1 | 0.0010 | 96% | 99% | 0.861 | 0.0079 | 0.0082 | 0.012 |
| NFKB1 | CD4 | CYBB | 0.0010 | 91% | 99% | 0.863 | 4.3E−04 | 7.8E−04 | 0.015 |
| NFKB1 | IL18BP | CD4 | 1.3E−04 | 91% | 99% | 0.845 | 0.0060 | 0.0250 | 0.014 |
| NFKB1 | IL18BP | SERPING1 | 1.7E−04 | 82% | 100% | 0.822 | 1.7E−04 | 9.2E−04 | 0.013 |
| NFKB1 | IL18BP | PTGS2 | 4.8E−04 | 91% | 99% | 0.822 | 5.6E−05 | 7.0E−04 | 0.017 |
| NFKB1 | IL18BP | IFI16 | 4.8E−04 | 82% | 100% | 0.820 | 8.2E−04 | 9.4E−04 | 0.0079 |
| TIMP1 | CD4 | MYC | 0.0000 | 91% | 100% | 0.858 | 5.8E−04 | 6.7E−04 | 0.0064 |
| TIMP1 | CD4 | SERPING1 | 8.2E−05 | 91% | 99% | 0.804 | 1.3E−04 | 0.0011 | 0.0039 |
| TIMP1 | CD4 | IFI16 | 1.2E−04 | 91% | 99% | 0.775 | 3.7E−04 | 0.0016 | 0.0037 |
| TIMP1 | CD4 | SERPINA1 | 3.5E−04 | 91% | 98% | 0.749 | 4.5E−04 | 4.3E−04 | 0.0048 |
| TIMP1 | CD4 | EGR1 | 6.0E−04 | 100% | 96% | 0.725 | 4.6E−04 | 1.8E−04 | 0.0098 |
| TIMP1 | CD4 | TNFSF5 | 9.1E−04 | 86% | 99% | 0.754 | 2.4E−05 | 4.4E−05 | 0.0051 |

TABLE 7

Latent class modeling-ranking of p-values form most to least significant 1-gene model estimating RA v. Normal discrimination (RA, N = 20, Normal N = 32)

| Gene 1 | Incremental P-Value | R-SQ |
|---|---|---|
| ICAM1 | 3.70E−06 | 0.344 |
| STAT3 | 5.50E−06 | 0.365 |
| TGFB1 | 7.50E−06 | 0.353 |
| CSPG2 | 9.50E−06 | 0.314 |
| TLR2 | 3.30E−05 | 0.295 |
| HLADRA | 5.20E−05 | 0.288 |
| IL1B | 0.00053 | |
| CASP9 | 0.00088 | |
| ITGAL | 0.0056 | |
| NFKBIB | 0.0075 | |
| EGR1 | 0.0079 | |
| SERPINE1 | 0.013 | |
| TSC22D3 | 0.014 | |
| NFKB1 | 0.015 | |
| TGFBR2 | 0.031 | |
| CD4 | 0.044 | |
| CASP3 | 0.063 | |
| MMP9 | 0.087 | |
| IL1RN | 0.098 | |
| CD14 | 0.17 | |
| BCL2 | 0.19 | |
| MEF2C | 0.28 | |
| HSPA1A | 0.52 | |
| IL18 | 0.56 | |

TABLE 8

Latent class modeling-estimating RA v. Normal discrimination in a dataset using a 2-gene model (RA, N = 20, Normal N = 32)

| gene 1 | gene 2 | Gene 2 Inc p-value | % normals | % RA | R-SQ | Gene 1 Inc P-Value |
|---|---|---|---|---|---|---|
| ICAM1 | HLADRA | 0.0020 | 91% | 90% | 0.677 | 0.0020 |
| ICAM1 | HSPA1A | 0.0100 | 72% | 100% | 0.466 | 0.0003 |
| ICAM1 | CD14 | 0.0160 | 91% | 70% | 0.457 | 0.0010 |
| ICAM1 | TGFBR2 | 0.0310 | 72% | 95% | 0.433 | 0.0008 |
| STAT3 | HSPA1A | 0.0029 | 91% | 95% | 0.703 | 0.0006 |
| STAT3 | HLADRA | 0.0029 | 94% | 90% | 0.608 | 0.0011 |
| STAT3 | CD14 | 0.0077 | 94% | 80% | 0.550 | 0.0007 |
| STAT3 | TGFBR2 | 0.0280 | 88% | 85% | 0.469 | 0.0010 |
| TGFB1 | HLADRA | 0.0012 | 94% | 90% | 0.675 | 0.0011 |
| TGFB1 | HSPA1A | 0.0055 | 97% | 85% | 0.615 | 0.0004 |
| CSPG2 | HLADRA | 0.0012 | 94% | 85% | 0.626 | 0.0014 |

TABLE 8-continued

Latent class modeling-estimating RA v. Normal
discrimination in a dataset using a 2-gene model (RA, N = 20, Normal N = 32)

| gene 1 | gene 2 | Gene 2 Inc p-value | % normals | % RA | R-SQ | Gene 1 Inc P-Value |
|---|---|---|---|---|---|---|
| CSPG2 | IL18 | 0.0052 | 75% | 95% | 0.478 | 0.0003 |
| CSPG2 | CD14 | 0.0370 | 88% | 75% | 0.409 | 0.0006 |
| TLR2 | HLADRA | 0.0020 | 91% | 85% | 0.562 | 0.0016 |
| HLADRA | CASP9 | 0.0015 | 88% | 90% | 0.542 | 0.0005 |
| HLADRA | MEF2C | 0.0017 | 91% | 85% | 0.552 | 0.0003 |
| HLADRA | ITGAL | 0.0029 | 91% | 80% | 0.507 | 0.0004 |
| HLADRA | IL1B | 0.0063 | 88% | 75% | 0.452 | 0.0016 |
| HLADRA | NFKBIB | 0.0036 | 94% | 70% | 0.460 | 0.0009 |
| HLADRA | CD4 | 0.0047 | 97% | 65% | 0.448 | 0.0004 |
| HLADRA | NFKB1 | 0.0077 | 97% | 65% | 0.430 | 0.0005 |
| HLADRA | TGFBR2 | 0.0083 | 91% | 80% | 0.463 | 0.0004 |
| HLADRA | SERPINE1 | 0.0130 | 75% | 90% | 0.403 | 0.0011 |
| HLADRA | CD14 | 0.0430 | 90.60% | 70.00% | 0.390 | 0.0008 |

TABLE 9

Latent class modeling-estimating RA v. Normal
discrimination in a dataset using a 3-gene model (RA, N = 20, Normal N = 32)

| gene 1 | gene 2 | gene 3 | Gene 3 Inc p-value | % normals | % RA | LG R-SQ | Gene 1 Inc P-Value | Gene 2 Inc P-Value |
|---|---|---|---|---|---|---|---|---|
| ICAM1 | HLADRA | HSPA1A | 0.0270 | 97% | 95% | 0.827 | 0.0055 | 0.0110 |
| ICAM1 | HLADRA | MMP9 | 0.0320 | 97% | 90% | 0.794 | 0.0030 | 0.0130 |
| ICAM1 | HSPA1A | TGFB1 | 0.0100 | 97% | 85% | 0.695 | 0.0320 | 0.0043 |
| ICAM1 | HSPA1A | CSPG2 | 0.0430 | 88% | 90% | 0.551 | 0.0081 | 0.0084 |
| ICAM1 | CD14 | CSPG2 | 0.0092 | 100% | 70% | 0.625 | 0.0180 | 0.0100 |
| ICAM1 | CD14 | TGFBR2 | 0.0470 | 94% | 75% | 0.535 | 0.0018 | 0.0260 |
| ICAM1 | TGFBR2 | STAT3 | 0.0220 | 88% | 90% | 0.570 | 0.0250 | 0.0100 |
| ICAM1 | TGFBR2 | TGFB1 | 0.0280 | 88% | 90% | 0.566 | 0.0100 | 0.0100 |
| ICAM1 | TGFBR2 | CSPG2 | 0.0390 | 91% | 90% | 0.565 | 0.0084 | 0.0180 |
| STAT3 | HSPA1A | TGFB1 | 0.0340 | 97% | 95% | 0.807 | 0.0068 | 0.0061 |
| STAT3 | HLADRA | MMP9 | 0.0290 | 94% | 90% | 0.677 | 0.0009 | 0.0037 |
| STAT3 | CD14 | CSPG2 | 0.0170 | 91% | 85% | 0.640 | 0.0035 | 0.0051 |
| STAT3 | TGFBR2 | ICAM1 | 0.0250 | 88% | 90% | 0.570 | 0.0220 | 0.0100 |
| TGFB1 | HLADRA | HSPA1A | 0.0170 | 97% | 95% | 0.792 | 0.0014 | 0.0020 |
| TGFB1 | HSPA1A | MMP9 | 0.0370 | 97% | 85% | 0.699 | 0.0002 | 0.0025 |
| CSPG2 | HLADRA | CD14 | 0.0370 | 97% | 90% | 0.708 | 0.0024 | 0.0035 |
| CSPG2 | IL18 | CD14 | 0.0210 | 81% | 100% | 0.620 | 0.0013 | 0.0027 |
| CSPG2 | IL18 | HSPA1A | 0.0490 | 88% | 85% | 0.552 | 0.0002 | 0.0040 |
| CSPG2 | CD14 | IL1B | 0.0100 | 88% | 90% | 0.564 | 0.0009 | 0.0046 |
| CSPG2 | CD14 | EGR1 | 0.0085 | 97% | 75% | 0.563 | 0.0010 | 0.0048 |
| CSPG2 | CD14 | TGFB1 | 0.0260 | 100% | 70% | 0.532 | 0.0180 | 0.0140 |
| CSPG2 | CD14 | CASP9 | 0.0310 | 91% | 80% | 0.509 | 0.0026 | 0.0083 |
| TLR2 | HLADRA | MEF2C | 0.0260 | 97% | 95% | 0.671 | 0.0140 | 0.0012 |
| TLR2 | HLADRA | MMP9 | 0.0430 | 97% | 80% | 0.617 | 0.0008 | 0.0028 |
| HLADRA | CASP9 | HSPA1A | 0.0240 | 91% | 95% | 0.643 | 0.0024 | 0.0047 |
| HLADRA | IL1B | CD4 | 0.0490 | 81% | 95% | 0.537 | 0.0008 | 0.0380 |

TABLE 10

Latent class modeling-estimating RA v. Normal
discrimination in a dataset using a 4-gene model (RA, N = 20, Normal N = 32)

| gene 1 | gene 2 | gene 3 | gene 4 | Gene 4 Inc p-value | % normals | % RA | R-Sq | Gene 1 Inc P-Value | Gene 2 Inc P-Value | Gene 3 Inc P-Value |
|---|---|---|---|---|---|---|---|---|---|---|
| ICAM1 | HLADRA | HSPA1A | TGFB1 | 0.037 | 100% | 100% | 97% | 0.049 | 0.012 | 0.029 |
| ICAM1 | HSPA1A | TGFB1 | MEF2C | 0.035 | 90% | 100% | 0.7551 | 0.018 | 0.0046 | 0.0045 |
| ICAM1 | HSPA1A | CSPG2 | IL18 | 0.043 | 70% | 100% | 0.6233 | 0.049 | 0.014 | 0.0084 |
| ICAM1 | HSPA1A | CSPG2 | CD4 | 0.048 | 90% | 91% | 0.6477 | 0.0046 | 0.009 | 0.0096 |
| ICAM1 | HSPA1A | CSPG2 | MEF2C | 0.046 | 100% | 84% | 0.6204 | 0.0085 | 0.011 | 0.022 |
| ICAM1 | CD14 | CSPG2 | TGFBR2 | 0.036 | 100% | 91% | 0.7388 | 0.012 | 0.014 | 0.011 |
| ICAM1 | CD14 | CSPG2 | NFKBIB | 0.041 | 85% | 97% | 0.7137 | 0.013 | 0.014 | 0.0071 |

TABLE 10-continued

Latent class modeling-estimating RA v. Normal discrimination in a dataset using a 4-gene model (RA, N = 20, Normal N = 32)

| gene 1 | gene 2 | gene 3 | gene 4 | Gene 4 Inc p-value | % normals | % RA | R-Sq | Gene 1 Inc P-Value | Gene 2 Inc P-Value | Gene 3 Inc P-Value |
|---|---|---|---|---|---|---|---|---|---|---|
| ICAM1 | CD14 | TGFBR2 | CSPG2 | 0.011 | 100% | 91% | 0.7388 | 0.012 | 0.014 | 0.036 |
| ICAM1 | CD14 | TGFBR2 | TGFB1 | 0.029 | 75% | 100% | 0.6232 | 0.02 | 0.036 | 0.025 |
| STAT3 | HLADRA | MMP9 | CSPG2 | 0.018 | 90% | 97% | 0.7763 | 0.035 | 0.0087 | 0.025 |
| STAT3 | HLADRA | MMP9 | EGR1 | 0.023 | 90% | 97% | 0.7668 | 0.0044 | 0.0077 | 0.019 |
| TGFB1 | HLADRA | HSPA1A | ICAM1 | 0.049 | 100% | 100% | 0.9662 | 0.037 | 0.012 | 0.029 |
| CSPG2 | HLADRA | CD14 | ITGAL | 0.03 | 100% | 100% | 0.9281 | 0.014 | 0.02 | 0.015 |
| CSPG2 | HLADRA | CD14 | TGFB1 | 0.043 | 95% | 97% | 0.8883 | 0.024 | 0.013 | 0.019 |
| CSPG2 | HLADRA | CD14 | STAT3 | 0.027 | 95% | 100% | 0.8679 | 0.023 | 0.018 | 0.019 |
| CSPG2 | HLADRA | CD14 | CASP9 | 0.026 | 90% | 100% | 0.827 | 0.0057 | 0.011 | 0.017 |
| CSPG2 | IL18 | CD14 | CASP9 | 0.028 | 95% | 91% | 0.7401 | 0.0077 | 0.0085 | 0.012 |
| CSPG2 | IL18 | CD14 | IL1B | 0.029 | 95% | 91% | 0.7367 | 0.0049 | 0.012 | 0.069 |
| CSPG2 | IL18 | CD14 | EGR1 | 0.047 | 85% | 97% | 0.7193 | 0.0054 | 0.014 | 0.013 |
| CSPG2 | IL18 | HSPA1A | TGFB1 | 0.028 | 90% | 94% | 0.7179 | 0.013 | 0.024 | 0.013 |
| CSPG2 | IL18 | HSPA1A | ICAM1 | 0.049 | 70% | 100% | 0.623 | 0.008 | 0.043 | 0.014 |
| CSPG2 | CD14 | IL1B | IL18 | 0.012 | 95% | 91% | 0.7367 | 0.0049 | 0.0069 | 0.029 |
| CSPG2 | CD14 | IL1B | EGR1 | 0.031 | 90% | 91% | 0.655 | 0.003 | 0.0027 | 0.024 |
| CSPG2 | CD14 | EGR1 | IL18 | 0.014 | 85% | 97% | 0.7193 | 0.0054 | 0.013 | 0.047 |
| CSPG2 | CD14 | EGR1 | CD4 | 0.033 | 85% | 88% | 0.6498 | 0.0033 | 0.006 | 0.007 |
| CSPG2 | CD14 | TGFB1 | HLADRA | 0.013 | 95% | 97% | 0.8883 | 0.024 | 0.019 | 0.043 |
| CSPG2 | CD14 | TGFB1 | CD4 | 0.033 | 90% | 88% | 0.5939 | 0.008 | 0.013 | 0.015 |
| CSPG2 | CD14 | TGFB1 | MEF2C | 0.045 | 75% | 94% | 0.5822 | 0.012 | 0.02 | 0.017 |
| CSPG2 | CD14 | CASP9 | HLADRA | 0.011 | 90% | 100% | 0.827 | 0.0057 | 0.017 | 0.026 |
| CSPG2 | CD14 | CASP9 | IL18 | 0.0085 | 95% | 91% | 0.7401 | 0.0077 | 0.012 | 0.028 |
| CSPG2 | CD14 | CASP9 | MEF2C | 0.045 | 80% | 94% | 0.5717 | 0.0023 | 0.014 | 0.014 |
| TLR2 | HLADRA | MEF2C | HSPA1A | 0.034 | 95% | 94% | 0.7467 | 0.0063 | 0.003 | 0.032 |
| TLR2 | HLADRA | MEF2C | MMP9 | 0.038 | 90% | 100% | 0.7412 | 0.0041 | 0.0019 | 0.021 |
| TLR2 | HLADRA | MMP9 | CASP9 | 0.025 | 90% | 94% | 0.7223 | 0.013 | 0.0035 | 0.013 |
| TLR2 | HLADRA | MMP9 | MEF2C | 0.021 | 90% | 100% | 0.7412 | 0.0041 | 0.0019 | 0.038 |
| TLR2 | HLADRA | MMP9 | IL1B | 0.045 | 85% | 97% | 0.6899 | 0.0033 | 0.0029 | 0.014 |
| HLADRA | CASP9 | HSPA1A | TLR2 | 0.029 | 100% | 97% | 0.8174 | 0.0045 | 0.017 | 0.014 |

TABLE 11

Results from estimating 4 models specifying different numbers of latent classes. The 2 class model is preferred according to the BIC criterion.

| | BIC(LL) |
|---|---|
| 1-Class | 828.3 |
| 2-Class | 800.4 |
| 3-Class | 809.3 |
| 4-Class | 831.4 |

TABLE 12

Estimated posterior membership probabilities for Normals

| Group | id# | tPn | CD4 | Latent Class1 | Latent Class2 | Assigned to Modal class |
|---|---|---|---|---|---|---|
| N | 1 | 34.41 | 15.03 | 1.0000 | 0.0000 | 1 |
| N | 2 | 34.48 | 15.28 | 1.0000 | 0.0000 | 1 |
| N | 3 | 33.66 | 14.87 | 0.9991 | 0.0009 | 1 |
| N | 4 | 33.51 | 14.76 | 0.9985 | 0.0015 | 1 |
| N | 5 | 34.57 | 15.3 | 1.0000 | 0.0000 | 1 |
| N | 6 | 34.46 | 15.57 | 0.9999 | 0.0001 | 1 |
| N | 7 | 33.48 | 15.46 | 0.9820 | 0.0180 | 1 |
| N | 8 | 33.73 | 15.65 | 0.9856 | 0.0144 | 1 |
| N | 9 | 33.95 | 14.8 | 0.9997 | 0.0003 | 1 |
| N | 10 | 34.65 | 15.29 | 1.0000 | 0.0000 | 1 |
| N | 11 | 35.15 | 14.73 | 1.0000 | 0.0000 | 1 |
| N | 12 | 33.63 | 15.07 | 0.9984 | 0.0016 | 1 |
| N | 13 | 34.14 | 15.31 | 0.9997 | 0.0003 | 1 |
| N | 14 | 33.66 | 14.3 | 0.9986 | 0.0014 | 1 |
| N | 15 | 35.03 | 14.97 | 1.0000 | 0.0000 | 1 |
| N | 16 | 32.32 | 14.67 | 0.9230 | 0.0770 | 1 |
| N | 17 | 32.07 | 14.48 | 0.8999 | 0.1001 | 1 |
| N | 18 | 33.81 | 14.89 | 0.9995 | 0.0005 | 1 |
| N | 19 | 33.06 | 14.15 | 0.9911 | 0.0089 | 1 |
| N | 20 | 32.91 | 14.11 | 0.9866 | 0.0134 | 1 |
| N | 21 | 31.75 | 14.65 | 0.6621 | 0.3379 | 1 |
| N | 22 | 33.54 | 14.82 | 0.9986 | 0.0014 | 1 |
| N | 23 | 33.56 | 15.22 | 0.9963 | 0.0037 | 1 |
| N | 24 | 32.16 | 14.5 | 0.9181 | 0.0819 | 1 |
| N | 25 | 33.29 | 14.08 | 0.9934 | 0.0066 | 1 |
| N | 26 | 32.8 | 14.18 | 0.9851 | 0.0149 | 1 |
| N | 27 | 33.67 | 15.26 | 0.9974 | 0.0026 | 1 |
| N | 28 | 31.49 | 13.83 | 0.8031 | 0.1969 | 1 |
| N | 29 | 35.89 | 16.05 | 1.0000 | 0.0000 | 1 |
| N | 30 | 34.22 | 14.91 | 0.9999 | 0.0001 | 1 |
| N | 31 | 33.58 | 14.67 | 0.9989 | 0.0011 | 1 |
| N | 32 | 34.57 | 14.67 | 1.0000 | 0.0000 | 1 |
| N | 33 | 34.16 | 15.1 | 0.9998 | 0.0002 | 1 |
| N | 34 | 35.02 | 15.48 | 1.0000 | 0.0000 | 1 |
| N | 35 | 33.79 | 14.9 | 0.9994 | 0.0006 | 1 |
| N | 36 | 34.45 | 15.06 | 1.0000 | 0.0000 | 1 |
| N | 37 | 34.79 | 15.36 | 1.0000 | 0.0000 | 1 |
| N | 38 | 33.35 | 15.02 | 0.9952 | 0.0048 | 1 |
| N | 39 | 34.59 | 15.3 | 1.0000 | 0.0000 | 1 |
| N | 40 | 33.48 | 14.73 | 0.9984 | 0.0016 | 1 |
| N | 41 | 34.43 | 15.4 | 0.9999 | 0.0001 | 1 |
| N | 42 | 35.06 | 15.23 | 1.0000 | 0.0000 | 1 |
| N | 43 | 33.82 | 14.71 | 0.9995 | 0.0005 | 1 |
| N | 44 | 33.87 | 14.9 | 0.9996 | 0.0004 | 1 |
| N | 45 | 33.82 | 15.16 | 0.9991 | 0.0009 | 1 |
| N | 46 | 34.78 | 15.05 | 1.0000 | 0.0000 | 1 |
| N | 47 | 33.79 | 14.94 | 0.9994 | 0.0006 | 1 |
| N | 48 | 34.37 | 15.67 | 0.9996 | 0.0004 | 1 |
| N | 49 | 32.28 | 14.47 | 0.9442 | 0.0558 | 1 |
| N | 50 | 32.34 | 14.85 | 0.8674 | 0.1326 | 1 |

TABLE 12-continued

Estimated posterior membership probabilities for Normals

| Group | id# | tPn | CD4 | Latent Class1 | Latent Class2 | Assigned to Modal class |
|---|---|---|---|---|---|---|
| N | 51 | 32.85 | 15.08 | 0.9506 | 0.0494 | 1 |
| N | 52 | 32.31 | 14.71 | 0.9099 | 0.0901 | 1 |
| N | 53 | 34.56 | 15.39 | 1.0000 | 0.0000 | 1 |
| N | 54 | 34.28 | 15 | 0.9999 | 0.0001 | 1 |
| N | 56 | 34.34 | 15.19 | 0.9999 | 0.0001 | 1 |
| N | 57 | 30.89 | 13.93 | 0.6329 | 0.3671 | 1 |
| N | 58 | 32.66 | 14.84 | 0.9598 | 0.0402 | 1 |
| N | 59 | 31.4 | 14.22 | 0.7389 | 0.2611 | 1 |
| N | 60 | 32.38 | 14.33 | 0.9625 | 0.0375 | 1 |
| N | 61 | 32.29 | 14.53 | 0.9402 | 0.0598 | 1 |
| N | 62 | 32.61 | 13.94 | 0.9638 | 0.0362 | 1 |
| N | 63 | 33.13 | 14.37 | 0.9949 | 0.0051 | 1 |
| N | 64 | 33.81 | 14.76 | 0.9995 | 0.0005 | 1 |
| N | 65 | 33.08 | 14.73 | 0.9931 | 0.0069 | 1 |
| N | 66 | 33.91 | 14.96 | 0.9996 | 0.0004 | 1 |
| N | 67 | 33.44 | 14.54 | 0.9982 | 0.0018 | 1 |
| N | 68 | 34.07 | 15.03 | 0.9998 | 0.0002 | 1 |
| N | 69 | 35.18 | 15.18 | 1.0000 | 0.0000 | 1 |
| N | 70 | 33.88 | 14.86 | 0.9996 | 0.0004 | 1 |
| N | 71 | 32.03 | 14.74 | 0.7698 | 0.2302 | 1 |
| N | 72 | 34.05 | 15.32 | 0.9995 | 0.0005 | 1 |
| N | 73 | 34.19 | 14.79 | 0.9999 | 0.0001 | 1 |
| N | 74 | 34.77 | 15.06 | 1.0000 | 0.0000 | 1 |
| N | 75 | 31.99 | 13.93 | 0.9048 | 0.0952 | 1 |
| N | 76 | 33.56 | 14.68 | 0.9988 | 0.0012 | 1 |
| N | 77 | 33.84 | 14.89 | 0.9995 | 0.0005 | 1 |
| N | 78 | 30.86 | 13.88 | 0.6323 | 0.3677 | 1 |
| N | 79 | 33.23 | 15.14 | 0.9878 | 0.0122 | 1 |
| N | 80 | 34.05 | 14.88 | 0.9998 | 0.0002 | 1 |
| N | 81 | 35.2 | 15.73 | 1.0000 | 0.0000 | 1 |
| N | 82 | 33.27 | 14.66 | 0.9968 | 0.0032 | 1 |
| N | 83 | 34.29 | 15.34 | 0.9998 | 0.0002 | 1 |
| N | 84 | 33.1 | 14.04 | 0.9891 | 0.0109 | 1 |
| N | 85 | 33.92 | 14.64 | 0.9997 | 0.0003 | 1 |
| N | 86 | 32.29 | 14.17 | 0.9547 | 0.0453 | 1 |
| N | 87 | 33.78 | 15.12 | 0.9991 | 0.0009 | 1 |
| N | 88 | 32.8 | 15.2 | 0.8895 | 0.1105 | 1 |
| N | 89 | 34.62 | 15.37 | 1.0000 | 0.0000 | 1 |
| N | 90 | 30.66 | 13.63 | 0.5947 | 0.4053 | 1 |
| N | 91 | 32.75 | 14.99 | 0.9474 | 0.0526 | 1 |
| N | 92 | 33.62 | 14.28 | 0.9983 | 0.0017 | 1 |
| N | 93 | 31.47 | 13.97 | 0.8066 | 0.1934 | 1 |
| N | 94 | 33.55 | 14.92 | 0.9984 | 0.0016 | 1 |
| N | 95 | 32.69 | 13.74 | 0.9373 | 0.0627 | 1 |
| N | 96 | 34.59 | 14.56 | 1.0000 | 0.0000 | 1 |
| N | 97 | 32.34 | 14.46 | 0.9542 | 0.0458 | 1 |
| N | 98 | 33.64 | 14.43 | 0.9989 | 0.0011 | 1 |
| N | 99 | 34.56 | 14.89 | 1.0000 | 0.0000 | 1 |
| N | 100 | 32.9 | 14.78 | 0.9854 | 0.0146 | 1 |
| N | 101 | 32.93 | 14.73 | 0.9885 | 0.0115 | 1 |
| N | 102 | 32.74 | 14.75 | 0.9758 | 0.0242 | 1 |
| N | 103 | 32.67 | 14.74 | 0.9703 | 0.0297 | 1 |
| N | 104 | 32.48 | 14.54 | 0.9654 | 0.0346 | 1 |
| N | 105 | 32.93 | 14.99 | 0.9753 | 0.0247 | 1 |
| N | 106 | 33.71 | 14.26 | 0.9986 | 0.0014 | 1 |
| N | 107 | 33.72 | 14.43 | 0.9991 | 0.0009 | 1 |
| N | 108 | 33.25 | 14.75 | 0.9962 | 0.0038 | 1 |
| N | 109 | 35.38 | 16.17 | 1.0000 | 0.0000 | 1 |
| N | 110 | 31.79 | 14.12 | 0.8796 | 0.1204 | 1 |
| N | 111 | 31.36 | 13.69 | 0.7446 | 0.2554 | 1 |
| N | 112 | 39.54 | 16.75 | 1.0000 | 0.0000 | 1 |
| N | 113 | 34.28 | 14.68 | 0.9999 | 0.0001 | 1 |
| N | 114 | 31.66 | 14.01 | 0.8523 | 0.1477 | 1 |
| N | 115 | 31.92 | 14.44 | 0.8674 | 0.1326 | 1 |
| N | 116 | 32.94 | 15.07 | 0.9680 | 0.0320 | 1 |
| N | 117 | 33.17 | 14.3 | 0.9950 | 0.0050 | 1 |
| N | 118 | 33.15 | 15 | 0.9897 | 0.0103 | 1 |
| N | 119 | 34.91 | 15.13 | 1.0000 | 0.0000 | 1 |
| N | 120 | 33.68 | 14.76 | 0.9992 | 0.0008 | 1 |
| N | 121 | 33.7 | 15.14 | 0.9985 | 0.0015 | 1 |
| N | 122 | 32.22 | 14.16 | 0.9474 | 0.0526 | 1 |
| N | 123 | 33.48 | 14.96 | 0.9977 | 0.0023 | 1 |
| N | 124 | 34.15 | 14.65 | 0.9998 | 0.0002 | 1 |
| N | 125 | 32.67 | 14.65 | 0.9767 | 0.0233 | 1 |
| N | 126 | 32.75 | 14.38 | 0.9855 | 0.0145 | 1 |
| N | 127 | 33.52 | 15.04 | 0.9976 | 0.0024 | 1 |
| N | 128 | 33.77 | 14.79 | 0.9994 | 0.0006 | 1 |
| N | 129 | 33.54 | 15.15 | 0.9969 | 0.0031 | 1 |
| N | 130 | 32.77 | 14.88 | 0.9693 | 0.0307 | 1 |
| N | 131 | 34.32 | 14.95 | 0.9999 | 0.0001 | 1 |
| N | 132 | 34.38 | 15.58 | 0.9998 | 0.0002 | 1 |
| N | 133 | 32.54 | 15.16 | 0.7576 | 0.2424 | 1 |
| N | 134 | 32.59 | 14.8 | 0.9545 | 0.0455 | 1 |

TABLE 13

Estimated posterior membership probabilities for RA subjects

| Group | id# | tPn | CD4 | Latent Class1 | Latent Class2 | Assigned to Modal class |
|---|---|---|---|---|---|---|
| RA | 1 | 30.44 | 16.7 | 0.0000 | 1.0000 | 2 |
| RA | 2 | 32.55 | 15.68 | 0.0521 | 0.9479 | 2 |
| RA | 3 | 30.26 | 14.66 | 0.0135 | 0.9865 | 2 |
| RA | 4 | 31.69 | 15.36 | 0.0120 | 0.9880 | 2 |
| RA | 5 | 32.56 | 15.41 | 0.3758 | 0.6242 | 2 |
| RA | 6 | 31.35 | 15.05 | 0.0354 | 0.9646 | 2 |
| RA | 7 | 31.3 | 14.77 | 0.1764 | 0.8236 | 2 |
| RA | 8 | 30.91 | 15.21 | 0.0012 | 0.9988 | 2 |
| RA | 9 | 32.13 | 15.6 | 0.0113 | 0.9887 | 2 |
| RA | 10 | 31.48 | 16.37 | 0.0000 | 1.0000 | 2 |
| RA | 11 | 31.39 | 14.73 | 0.2747 | 0.7253 | 2 |
| RA | 12 | 31.91 | 14.96 | 0.4034 | 0.5966 | 2 |
| RA | 13 | 30.15 | 13.81 | 0.4312 | 0.5688 | 2 |
| RA | 14 | 31.43 | 15.22 | 0.0123 | 0.9877 | 2 |
| RA | 15 | 30.65 | 14.28 | 0.2956 | 0.7044 | 2 |
| RA | 16 | 30.51 | 14.59 | 0.0496 | 0.9504 | 2 |
| RA | 17 | 30.47 | 14.42 | 0.1194 | 0.8806 | 2 |
| RA | 18 | 30.13 | 15.05 | 0.0002 | 0.9998 | 2 |
| RA | 19 | 30.76 | 15.79 | 0.0000 | 1.0000 | 2 |
| RA | 20 | 31.95 | 15.49 | 0.0123 | 0.9877 | 2 |
| RA | 21 | 30.22 | 14.22 | 0.1714 | 0.8286 | 2 |
| RA | 22 | 30.81 | 14.52 | 0.1678 | 0.8322 | 2 |

TABLE 14

Estimated posterior membership probabilities for MS subjects

| Group | id# | tPn | CD4 | Latent Class1 | Latent Class2 | Assigned to Modal class |
|---|---|---|---|---|---|---|
| MS | ms1 | 31.91 | 14.2 | 0.8998 | 0.1002 | 1 |
| MS | ms10 | 32.47 | 14.51 | 0.9655 | 0.0345 | 1 |
| MS | ms11 | 30.84 | 14.33 | 0.3490 | 0.6510 | 2 |
| MS | ms2 | 30.59 | 14.61 | 0.0550 | 0.9450 | 2 |
| MS | ms3 | 32.93 | 14.44 | 0.9913 | 0.0087 | 1 |
| MS | ms4 | 32.47 | 14.8 | 0.9309 | 0.0691 | 1 |
| MS | ms5 | 32.08 | 14.52 | 0.8938 | 0.1062 | 1 |
| MS | ms6 | 34.26 | 14.62 | 0.9999 | 0.0001 | 1 |
| MS | ms7 | 33.24 | 14.95 | 0.9940 | 0.0060 | 1 |
| MS | ms8 | 32.08 | 15.87 | 0.0004 | 0.9996 | 2 |
| MS | ms9 | 33.14 | 14.72 | 0.9947 | 0.0053 | 1 |

TABLE 15

Relationship between the Clinical Outcomes at baseline and gene expressions for the 22 washed-out RAs.
Genes found to be significantly related to each of 10 clinical outcomes*

| Predictor | $R^2$ | gene1 | p-value | gene2 | p-value |
|---|---|---|---|---|---|
| W-CRP | 0.748 | IL8 | 0.0002 | MMP9 | 0.0002 |
| W-DAS | 0.525 | IL1R1 | 0.0039 | IL8 | 0.0042 |

TABLE 15-continued

Relationship between the Clinical Outcomes at baseline and gene expressions for the 22 washed-out RAs.
Genes found to be significantly related to each of 10 clinical outcomes*

| Predictor | $R^2$ | gene1 | p-value | gene2 | p-value |
|---|---|---|---|---|---|
| W-ESR | 0.818 | TNFSF6 | 5.5E−06 | CD14 | 0.0011 |
| W-HAQ | 0.000 | | | | |
| PHYSassessDisease | 0.433 | IL10 | 0.0100 | | |
| SubAssessDisease | 0.473 | TLR2 | 0.00015 | IL18 | 0.0390 |
| SubAssessPain | 0.224 | GCLC | 0.0250 | | |
| SwollJoints | 0.570 | IL8 | 0.00044 | TLR2 | 0.0150 |
| TenderJoints | 0.500 | IL1R1 | 0.00063 | CXCL1 | 0.0060 |
| SharpScore | 0.000 | | | | |

*The stepwise ordinal logit modeling procedure entered the most significant (labeled 'gene1') and up to one additional predictor (labeled 'gene2') in the model

TABLE 16

Average % CD Standard

| sample | | (s/x̄) | | | |
|---|---|---|---|---|---|
| | mean | s = .2 | s = .5 | s = 1.0 | s = 2.0 |
| TLR2 | 15.87 | 1.26% | 3.15% | 6.30% | 12.60% |
| CD4 | 14.86 | 0.08% | 0.21% | 0.42% | 0.85% |
| NFKB1 | 17.29 | 0.00% | 0.01% | 0.02% | 0.05% |

TABLE 17

Expected Percentage of Variance of Y Reproduced by Y'

| | Squared Correlation (Y, Y') | | | |
|---|---|---|---|---|
| | s = .2 | s = .5 | s = 1.0 | s = 2.0 |
| TLR2 | 94% | 72% | 39% | 14% |
| CD4 | 88% | 54% | 23% | 7% |
| NFKB1 | 93% | 67% | 33% | 11% |

TABLE 18

Observed Percentage of Variance of Y Reproduced by Y' using the generated data

| | Observed Squared Correlation (Y, Y') | | | |
|---|---|---|---|---|
| | s = .2 | s = .5 | s = 1.0 | s = 2.0 |
| TLR2 | 93% | 76% | 38% | 20% |
| CD4 | 90% | 57% | 31% | 13% |
| NFKB1 | 91% | 67% | 40% | 16% |

TABLE 19

Summary of results from simulation including the discrimination $R^2$ based on 2 models.

Adding no error - original data — Logit model $R^2 = 1$ — LC model $R^2 = .73$

| | N | Minimum | Maximum | Mean | Std. Deviation | # misclassified |
|---|---|---|---|---|---|---|
| TLR2 | 155 | 13.49 | 17.60 | 15.87 | 0.79 | none |
| CD4 | 156 | 13.63 | 16.76 | 14.86 | 0.54 | |
| NFKB1 | 156 | 15.70 | 21.94 | 17.29 | 0.71 | |

Adding small amount of error - s = 0.2 — $R^2 = .87$ — $R^2 = .56$

| | N | Minimum | Maximum | Mean | Std. Deviation | # misclassified |
|---|---|---|---|---|---|---|
| tP2lr | 155 | 13.41 | 17.68 | 15.89 | 0.83 | 2 RAs + 2 Norms |
| cP2d | 156 | 13.37 | 16.91 | 14.86 | 0.59 | |
| nP2fk | 156 | 15.35 | 21.74 | 17.29 | 0.74 | |

Adding moderate amount of error - s = 0.5 — $R^2 = .55$ — $R^2 = .53$

| | N | Minimum | Maximum | Mean | Std. Deviation | # misclassified |
|---|---|---|---|---|---|---|
| tl5r | 155 | 13.17 | 17.93 | 15.91 | 0.90 | 4 RAs + 8 Norms |
| c5d | 156 | 12.78 | 16.83 | 14.88 | 0.76 | |
| n5fk | 156 | 15.15 | 21.80 | 17.32 | 0.89 | |

Adding large amount of error - s = 1 — $R^2 = .33$ — $R^2 = .33$

| | N | Minimum | Maximum | Mean | Std. Deviation | # misclassified |
|---|---|---|---|---|---|---|
| tlr | 155 | 12.80 | 19.08 | 15.80 | 1.25 | 4 RAs + 38 Norms |
| cd | 156 | 12.41 | 17.51 | 15.04 | 1.17 | |
| nfk | 156 | 14.22 | 23.06 | 17.23 | 1.20 | |

Adding very large amount of error - s = 2 — $R^2 = .23$ — $R^2 = .28$

| | N | Minimum | Maximum | Mean | Std. Deviation | # misclassified |
|---|---|---|---|---|---|---|
| tl2r | 155 | 10.41 | 20.50 | 16.00 | 1.93 | 5 RAs + 42 Norms |
| c2d | 156 | 8.13 | 20.23 | 14.91 | 2.21 | |
| n2fk | 156 | 11.42 | 23.63 | 17.09 | 2.11 | |

What is claimed is:

1. A method of determining whether a human subject is suffering from or is at risk of developing rheumatoid arthritis, based on a blood sample from the subject, the sample providing a source of RNAs, the method comprising:

using quantitative amplification to obtain a quantitative measure of the amount of at least 2 constituents as distinct RNA constituents in the subject sample, wherein the first constituent is selected from the group consisting of TLR2, MMP9 and TGFB1, and the second constituent is selected from the group consisting of CD4, PTGS2 and HSPA1A, wherein the constituents are selected so as to distinguish from a normal and a rheumatoid arthritis-diagnosed subject with at least 75% accuracy, and wherein such measure for each constituent is obtained under measurement conditions that are (i) within a degree of repeatability of better than five percent; and (ii) the efficiencies of amplification are within two percent for each constituent, to arrive at a subject profile data set of a plurality of members;

assessing the subject profile data set; and comparing the subject profile data set to a baseline profile data set, wherein the baseline profile data set is derived from one or more subjects known not to be suffering from rheumatoid arthritis;

wherein a change in the expression pattern of the subject profile data set as compared to the baseline profile data set indicates that the subject is suffering from or is at risk of developing rheumatoid arthritis.

2. The method of claim 1, wherein said rheumatoid arthritis-diagnosed subject is washed out from therapy.

3. A method of claim 1, wherein the constituents are selected as to permit characterizing the severity of rheumatoid arthritis in relation to a normal subject over time so as to track movement toward normal as a result of successful therapy and away from normal in response to symptomatic flare.

4. The method of claim 1, wherein the at least the first constituent includes TRL2.

5. A method according to claim 1, further comprising obtaining quantitative measure of one or more constituents selected from the group consisting of IL18BP, HMBG1, C1QA, SERPING1, MYC, NFKB1, TNFSF5, LTA, TGFB1, DPP4, EGR1, IL1R1, ICAM1, IL1RN, TIMP1, MPO, MMP9, TNFSF6, IL1B, IFI16, and SERPINE1.

6. The method of claim 1, wherein the at least the first constituent includes MMP9.

7. A method according to claim 1, further comprising obtaining quantitative measure of one or more constituents selected from the group consisting of PTGS2, IFI16, C1QA, IL1R1, MYC, SERPINE1, MPO, NFKB1, TGFB1, EGR1, PLAUR, TNFSF5, SERPINA1, LTA, TIMP1, ICAM1, TNF, TLR2, and IL1B.

8. The method of claim 1, wherein the measurement conditions that are substantially repeatable are within a degree of repeatability of better than three percent.

9. The method of claim 1, wherein the efficiency of amplification for all constituents is less than one percent.

* * * * *